(12) United States Patent
Carroll et al.

(10) Patent No.: US 11,473,131 B2
(45) Date of Patent: Oct. 18, 2022

(54) METHODS FOR DETECTING GENOMIC DNA METHYLATION

(71) Applicant: THE TRUSTEES OF THE UNIVERSITY OF PENNSYLVANIA, Philadelphia, PA (US)

(72) Inventors: Martin Carroll, Philadelphia, PA (US); Stephen Master, Philadelphia, PA (US); Gerald Wertheim, Philadelphia, PA (US); Marlise Luskin, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 174 days.

(21) Appl. No.: 15/504,061

(22) PCT Filed: Aug. 21, 2015

(86) PCT No.: PCT/US2015/046247
§ 371 (c)(1),
(2) Date: Feb. 15, 2017

(87) PCT Pub. No.: WO2016/029088
PCT Pub. Date: Feb. 25, 2016

(65) Prior Publication Data
US 2017/0275686 A1 Sep. 28, 2017

Related U.S. Application Data

(60) Provisional application No. 62/198,433, filed on Jul. 29, 2015, provisional application No. 62/040,821, filed on Aug. 22, 2014.

(51) Int. Cl.
*C12Q 1/6855* (2018.01)
*C12Q 1/6827* (2018.01)
*C12Q 1/6876* (2018.01)
*C07H 21/04* (2006.01)
*C12P 19/34* (2006.01)

(52) U.S. Cl.
CPC ........... *C12Q 1/6855* (2013.01); *C07H 21/04* (2013.01); *C12P 19/34* (2013.01); *C12Q 1/6827* (2013.01); *C12Q 1/6876* (2013.01); *C12Q 2521/331* (2013.01)

(58) Field of Classification Search
CPC ........... C12Q 2523/125; C12Q 1/6855; C12Q 2521/331; C12Q 1/6827; C12Q 1/6876; C07H 21/04; C12P 19/34
See application file for complete search history.

(56) References Cited

U.S. PATENT DOCUMENTS

| 2007/0269801 A1 | 11/2007 | Fan |
| 2009/0047666 A1 | 2/2009 | Lofton-Day et al. |
| 2009/0317801 A1 | 12/2009 | Van Den Boom et al. |
| 2013/0309668 A1 | 11/2013 | Makarov et al. |

OTHER PUBLICATIONS

Khulan et al., "Comparative isoschizomer profiling of cytosine methylation: The HELP assay," Genomie Research vol. 16, pp. 1046-1055. (Year: 2006).*
Wertheim et al., "Microsphere-Based Multiplex Analysis of DNA Methylation in Acute Myeloid Leukemia," The Journal of Molecular Diagnostics, March, vol. 16, No. 2, pp. 207-215. (Year: 2014).*
Figueroa et al., "DNA Methylation Signatures Identify Biologically Distinct Subtypes in Acute Myeloid Leukemia," Cancer Cell, Jan. 19, vol. 17, pp. 13-27. (Year: 2010).*
Kanel et al., "Quantitative 1-Step DNA Methylation Analysis with Native Genomic DNA as Template," Clinical Chemistry, vol. 56, No. 7, pp. 1098-1106. (Year: 2010).*
Yang et al., "Analysis of DNA Methylation in Various Swine Tissues," PLoS One, January, vol. 6, No. 1, e16229, pp. 1-9. (Year: 2011).*
Kellar et al., "Multiplexed microsphere-based flow cytometric assays," Experimental Hematology, vol. 30, pp. 1227-1237. (Year: 2002).*
Moller et al., "Detection of Neisseria meningitidis in Cerebrospinal Fluid Using a Multiplex PCR and the Luminex Detection Technology," Methods in Molecular Biology, Chapter 3, vol. 799, pp. 37-53. (Year: 2012).*
Wertheim et al., "Microsphere-Based Multiplex Analysis of DNA Methylation in Acute Myeloid Leukemia," The Journal of Molecular Diagnostics, vol. 16, No. 2, pp. 207-215. (Year: 2014).*
Figueroa et al., "Genome-Wide Determination of DNA Methylation by Hpall Tiny Fragment Enrichment by Ligation-Mediated PCR (HELP) for the Study of Acute Leukemias," Leukemia, pp. 395-407. (Year: 2009).*
Akalin et al., "Base-Pair Resolution DNA Methylation Sequencing Reveals Profoundly Divergent Epigenetic Landscapes in Acute Myeloid Leukemia," PLoS Genet 8(6):e1002781 (2012).
Alvarez et al., "DNA Methylation Profiles and Their Relationship with Cytogenetic Status in Adult Acute Myeloid Leukemia," PLoS ONE 5(8):e12197 (2010).
Bair et al., "Prediction by Supervised Principal Components," Journal of the American Statistical Association 101(473): 119-137 (2006).

(Continued)

*Primary Examiner* — Young J Kim
(74) *Attorney, Agent, or Firm* — Baker Botts L.L.P.

(57) ABSTRACT

The presently disclosed subject matter provides high-throughput methods for performing genomic DNA methylation assessments. The presently disclosed subject matter further provides methods for diagnosing a subject with a disease and/or disorder, and for determining the prognosis of a subject that has a disease and/or disorder. In certain embodiments, the present disclosure provides a diagnostic method that includes obtaining a biological sample from the subject; determining the methylation status of one or more genomic DNA loci in one or more cells of the biological sample; and diagnosing a disease and/or disorder in the subject, wherein the methylation status of the one or more genomic DNA loci indicates the presence of the disease and/or disorder in the subject.

5 Claims, 25 Drawing Sheets

Specification includes a Sequence Listing.

(56) References Cited

OTHER PUBLICATIONS

Baylin et al., "A decade of exploring the cancer epigenome—biological and translational implications," Nat Rev Cancer 11:726-734 (2011).
Bertoli et al., "Time from diagnosis to intensive chemotherapy initiation does not adversely impact the outcome of patients with acute myeloid leukemia," Blood 121(14):2618-2626 (2013).
Borssen et al., "Promoter DNA Methylation Pattern Identifies Prognostic Subgroups in Childhood T-Cell Acute Lymphoblastic Leukemia," PLoS ONE 8(6):e65373 (2013).
Bullinger et al., "Quantitative DNA methylation predicts survival in adult acute myeloid leukemia," Blood 115(3):636-642 (2010).
Chen et al., "Relation of Clinical Response and Minimal Residual Disease and Their Prognostic Impact on Outcome in Acute Myeloid Leukemia," J Clin Oncol 33:1258-1264 (2015).
Cheson et al., "Revised Recommendations of the International Working Group for Diagnosis, Standardization of Response Criteria, Treatment Outcomes, and Reporting Standards for Therapeutic Trials in Acute Myeloid Leukemia," J Clin Oncol 21:4642-4649 (2003).
Deneberg et al., "Gene-specific and global methylation patterns predict outcome in patients with acute myeloid leukemia," Leukemia 24:932-941 (2010).
Fernandez et al., "Anthracycline Dose Intensification in Acute Myeloid Leukemia," N Engl J Med 361:1249-1259 (2009).
Figueroa et al., "DNA Methylation Signatures Identify Biologically Distinct Subtypes in Acute Myeloid Leukemia," Cancer Cell 17:13-27 (2010).
Figueroa et al., "Genome-Wide Determination of DNA Methylation by *Hpa* II Tiny Fragment Enrichment by Ligation-Mediated PCR (HELP) for the Study of Acute Leukemias," C.W.E. So (ed.), Leukemia, Methods in Molecular Biology 538:395-407 (2009).
Grimwade et al., "Refinement of cytogenetic classification in acute myeloid leukemia: determination of prognostic significance of rare recurring chromosomal abnormalities among 5876 younger adult patients treated in the United Kingdom Medical Research Council trials," Blood 116(3):354-365 (2010).
Hanahan et al., "Hallmarks of Cancer: The Next Generation," Cell 144:646-674 (2011).
Hapfelmeier et al., "A new variable selection approach using Random Forests," Computational Statistics & Data Analysis 60:50-69 (2013).
Hastie et al., "The Elements of Statistical Learning. Data Mining, Inference, and Prediction," 2nd edition, Springer; 2009, Table of Contents.
International Search Report dated Jan. 28, 2016 in International Application No. PCT/US15/046247.
Jiang et al., "The Diagnostic Value of DNA Methylation in Leukemia: A Systematic Review and Meta-Analysis," PLoS ONE 9(5):e96822 (2014).
King et al., "A Comparative Analysis of Molecular Genetic and Conventional Cytogenetic Detection of Diagnostically Important Translocations in More Than 400 Cases of Acute Leukemia, Highlighting the Frequency of False-Negative Conventional Cytogenetics," Am J Clin Pathol 135:921-928 (2011).
Krug et al., "Complete remission and early death after intensive chemotherapy in patients aged 60 years or older with acute myeloid leukaemia: a web-based application for prediction of outcomes," Lancet 376:2000-2008 (2010).
Ligges et al., "Scatterplot3d—an R Package for Visualizing Multivariate Data," Journal of Statistical Software 8(11): 1-20 (2003).
Ishwaran et al., "Random Survival Forests," The Annals of Applied Statistics 2(3):841-860(2008).
Man et al., "Sorafenib treatment of FLT3-ITD(+) acute myeloid leukemia: favorable initial outcome and mechanisms of subsequent nonresponsiveness associated with the emergence of aD835 mutation," Blood 119(22):5133-5143 (2012).
Marcucci et al., "Epigenetics Meets Genetics in Acute Myeloid Leukemia: Clinical Impact of a Novel Seven-Gene Score," J Clin Oncol 32(6):548-556 (2014).
Nordlund et al., "Genome-wide signatures of differential DNA methylation in pediatric acute lymphoblastic leukemia," Genome Biology 14:r105 (2013).
Noushmehr et al., "Identification of a CpG Island Methylator Phenotype that Defines a Distinct Subgroup of Glioma," Cancer Cell 17:510-522 (2010).
Pedersen et al., "High recovery of cell-free methylated DNA based on a rapid bisulfite-treatment protocol," BMC Mol. Biol. 13:12 (2012).
Pemmaraju et al., "Investigational FMS-Like Tyrosine Kinase 3 (FLT3) Inhibitors in Treatment of Acute Myeloid Leukemia," Expert Opin Investig Drugs 23(7):943-954 (2014).
Raess et al., "Automated screening for myelodysplastic syndromes through analysis of complete blood count and cell population data parameters," Am. J. Hematol. 89:369-374 (2014).
Sandoval et al., "A Prognostic DNA Methylation Signature for Stage I Non-Small-Cell Lung Cancer," J Clin Oncol 31:4140-4147 (2013).
Schoofs et al., "Origins of aberrant DNA methylation in acute myeloid leukemia," Leukemia 28:1-14 (2014).
Sigalotti et al., "Whole genome methylation profiles as independent markers of survival in stage IIIc melanoma patients," J Transl Med. 10:185 (2012).
Stein et al., "AG-221, an Oral, Selective, First-in-Class, Potent Inhibitor of the IDH2 Mutant Metabolic Enzyme, Induces Durable Remissions in a Phase I Study in Patients with IDH2 Mutation Positive Advanced Hematologic Malignancies," Blood 124:115 (2014).
Vogelstein et al., "The multistep nature of cancer," Trends Genet. 9:138-41 (1993).
Walter et al., "Resistance prediction in AML: analysis of 4601 patients from MRC/NCRI, HOVON/SAKK, SWOG and MD Anderson Cancer Center," Leukemia 29:312-320 (2015).
Walter et al., "Effect of genetic profiling on prediction of therapeutic resistance and survival in adult acute myeloid leukemia," Leukemia 29:2104-2107 (2015).
Watson et al., "Emerging patterns of somatic mutations in cancer," Nat Rev Genet 14:703-718 (2013).
Wei et al., "Prognostic DNA Methylation Biomarkers in Ovarian Cancer," Clin Cancer Res. 12(9):2788-2794 (2006).
Wertheim et al., "Microsphere-Based Multiplex Analysis of DNA Methylation in Acute Myeloid Leukemia," J Mol Diagn. 16(2):207-215 (2014).
Wertheim et al., "Validation of DNA Methylation to Predict Outcome in Acute Myeloid Leukemia by Use of xMELP," Clin. Chem. 61:249-258 (2015).

\* cited by examiner

SEQUENCE LISTING

```
<160> NUMBER OF SEQ ID NOS: 4

<210> SEQ ID NO 1
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cggctgttca tg                                                            12

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgacgtcgac tatccatgaa cagc                                               24
```

```
<210> SEQ ID NO 3
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgcctgttca tg                                                           12

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgacgtcgac tatccatgaa cagg                                              24
```

METHODS FOR DETECTING GENOMIC DNA METHYLATION

CROSS-REFERENCE TO RELATED APPLICATIONS

This application is a U.S. National Stage Patent Application under 35 U.S.C. § 371 of International Application No. PCT/US2015/046247, filed on Aug. 21, 2015, which claims priority under 35 U.S.C. § 119 to U.S. Provisional Application No. 62/040,821, filed Aug. 22, 2014 and U.S. Provisional Application No. 62/198,433, filed Jul. 29, 2015. The contents of each of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jun. 15, 2022, is named 081406_0287 SL.txt and is 1,291 bytes in size.

BACKGROUND

Cancer is classically thought of as a disease caused by multiple genetic mutations that confer a proliferative and survival advantage to neoplastic cells (1, 2). Extensive investigations have explored the role of DNA sequence alterations in the pathogenesis of an oncogenic phenotype. Clinically, mutational assessment of pathologic tissue allows for definitive diagnosis of multiple tumor types, and specific mutations that have previously been shown to correlate with patient prognosis can inform therapeutic decisions (3).

Although the mutational profile of tumor cells is central to tumor pathogenesis and the clinical assessment of patients, it does not encompass the entire biologic dysregulation that occurs in tumor cells. Previous studies have demonstrated that cancer is not only driven by alterations in DNA sequence but also can be driven by epigenetic events or disrupted chromatin structure (4). The epigenetic changes of cancer cells can occur at multiple levels, including DNA methylation and histone modifications. Not surprisingly, large-scale analyses of epigenetic phenomena in various cancer types have shown clear correlations between patterns of epigenetic dysregulation and patient outcome. For example, results from The Cancer Genome Atlas (TCGA) project indicated that at least two types of glioblastoma could be identified simply from their level of DNA methylation and that these subcategories were significantly distinct in terms of patient outcome (5). This correlation between DNA methylation and clinical prognosis has been observed for numerous other cancers including acute myeloid leukemia (AML), T-cell and B-cell lymphoblastic leukemia, non-small cell lung carcinoma, ovarian carcinoma and melanoma (6-13).

Despite the clear relationship between DNA methylation and prognosis, assays that assess patterns of DNA methylation are not commonly used in clinical practice. The reasons underlying this paucity of methylation assays likely involve both the techniques and instrumentation required for DNA methylation analysis. Methods for analyzing DNA methylation typically utilize bisulfite treatment of DNA, which is not standard in a clinical molecular pathology laboratory and can readily result in sample degradation (14). Multilocus analysis DNA methylation usually involves platforms such as custom-made arrays or high-throughput sequencing, thereby substantially raising the cost of clinical implementation. Therefore, there exists a need in the art for DNA methylation assays that utilize techniques and equipment that are commonplace in clinical laboratories.

SUMMARY

The presently disclosed subject matter provides high-throughput methods for performing genomic DNA methylation assessments. The presently disclosed subject matter further provides methods for diagnosing a subject with a disease and/or disorder and for determining the prognosis of a subject that has a disease and/or disorder.

In certain embodiments, a method for determining the methylation status of one or more genomic DNA loci includes obtaining a biological sample from a subject; isolating genomic DNA from the biological sample; digesting a first sample of the genomic DNA with a methylation-insensitive restriction enzyme to form a first sample of genomic DNA fragments; amplifying the first sample of genomic DNA fragments to generate a first sample of amplified DNA fragments; hybridizing a genomic DNA locus-specific probe to the amplified DNA fragments of the first sample; and quantifying the amplified DNA fragments of the first sample hybridized to the locus-specific probe.

In certain embodiments, the method can further include digesting a second sample of the genomic DNA with a methylation-sensitive restriction enzyme to form a second sample of genomic DNA fragments; amplifying the second sample of genomic DNA fragments to generate a second sample of amplified DNA fragments; hybridizing a genomic DNA locus-specific probe to the amplified DNA fragments of the second sample; and quantifying the amplified DNA fragments of the second sample hybridized to the locus-specific probe.

In certain embodiments, the method can further include the ligation of linkers to the DNA fragments generated by the digestion of the genomic DNA prior to the amplification of the DNA fragments. In certain embodiments, the digestion of the genomic DNA and the ligation of the linkers to the DNA fragments can occur in a single reaction.

In certain embodiments, the method can include comparing the amount of amplified DNA fragments in the second sample hybridized to the locus-specific probe to the amount of amplified DNA fragments in the first sample hybridized to the locus-specific probe to determine the methylation status of the genomic DNA locus that corresponds to the locus-specific probe. In certain embodiments, the quantifying of amplified DNA fragments can be performed by flow cytometry. In certain embodiments, the comparison of the first and second samples can be normalized using the methylation status of one or more control genomic DNA loci.

The presently disclosed subject matter further provides for diagnostic methods. In certain embodiments, a diagnostic method of the present disclosure can include obtaining a biological sample from the subject; determining the methylation status of one or more genomic DNA loci in one or more cells of the biological sample; and diagnosing the disease and/or disorder in the subject, wherein the methylation status of the one or more genomic DNA loci indicates the presence of the disease and/or disorder in the subject.

In certain embodiments, a method for diagnosing acute myeloid leukemia (AML) in a subject can include obtaining a biological sample from the subject; determining the methylation status of one or more genomic DNA loci in one or more cells of the biological sample; and diagnosing AML in the subject, wherein the methylation status of the one or more genomic DNA loci indicates the presence of AML in the subject. In certain embodiments, the one or more genomic DNA loci can include, but are not limited to, Chr 17: 2208021 to 2208391 (MSPI0406S00783415); Chr 3: 129274773 to 129275235 (MSPI0406S00196536); Chr 1: 11723172 to 11723834 (MSPI0406S00011246); Chr 19: 1924052 to 1924259 (MSP10406S00861109); Chr 6: 108615428 to 108615973 (MSP10406S00333894); Chr 16: 30538940 to 30539797 (MSP10406S00754805); Chr 12: 53661106 to 53661621 (MSP10406S00613804); Chr 15: 65810129 to 65810776 (MSPI0406S00715593); Chr 14: 106354882 to 106355276 (MSPI0406S00698115); Chr 12: 6233715 to 6234255 (MSPI0406S00600078); Chr 20: 11899205 to 11899843 (MSP10406S00914183); Chr 15: 50838542 to 50839225 (MSPI0406S00710190); Chr 3: 8542436 to 8543339 (MSP10406S00163833); Chr 16: 68345197 to 68345691 (MSP10406S00765490); Chr 20: 11898849 to 11899205 (MSPI0406S00914182); Chr 20: 11898555 to 11898849 (MSPI0406S00914181); Chr 2: 158114266 to 158115184 (MSPI0406S00136939); or combinations thereof.

The presently disclosed subject matter further provides for prognostic methods. In certain embodiments, a prognostic method of the present disclosure can include obtaining a biological sample from the subject that has a disease and/or disorder; determining the methylation status of one or more target genomic DNA loci in one or more cells of the biological sample; and providing a disease and/or disorder prognosis based on the methylation status of the one or more genomic DNA loci in the subject.

In certain embodiments, a method for determining the prognosis of a subject that has AML includes obtaining a biological sample from the subject; determining the methylation status of one or more target genomic DNA loci in one or more cells of the biological sample; and providing an AML prognosis based on the methylation status of the one or more genomic DNA loci in the subject. In certain embodiments, the one or more genomic DNA loci can include, but are not limited to, Chr 17: 2208021 to 2208391 (MSPI0406S00783415); Chr 3: 129274773 to 129275235 (MSP10406S00196536); Chr 1: 11723172 to 11723834 (MSPI0406S00011246); Chr 19: 1924052 to 1924259 (MSPI0406S00861109); Chr 6: 108615428 to 108615973 (MSPI0406S00333894); Chr 16: 30538940 to 30539797 (MSPI0406S00754805); Chr 12: 53661106 to 53661621 (MSPI0406S00613804); Chr 15: 65810129 to 65810776 (MSPI0406S00715593); Chr 14: 106354882 to 106355276 (MSPI0406S00698115); Chr 12: 6233715 to 6234255 (MSPI0406S00600078); Chr 20: 11899205 to 11899843 (MSPI0406S00914183); Chr 15: 50838542 to 50839225 (MSPI0406S00710190); Chr 3: 8542436 to 8543339 (MSPI0406S00163833); Chr 16: 68345197 to 68345691 (MSPI0406S00765490); Chr 20: 11898849 to 11899205 (MSP10406S00914182); Chr 20: 11898555 to 11898849 (MSP10406S00914181); Chr 2: 158114266 to 158115184 (MSPI0406S00136939); or combinations thereof.

DETAILED DESCRIPTION

Figure 1A:
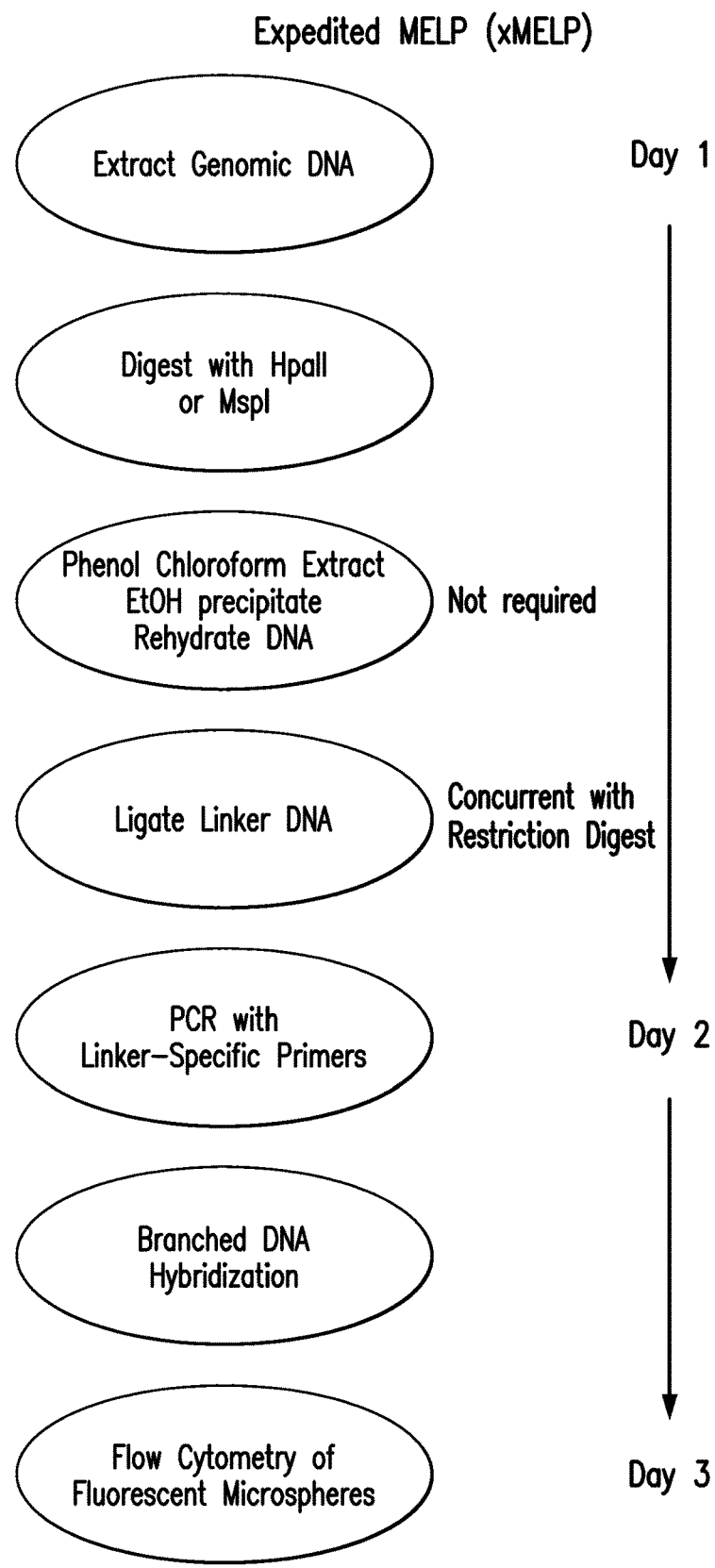
FIG. 1A-B. Comparison of the standard MELP assay to expedited MELP (xMELP). A) Schematic of standard MELP and xMELP. Alterations used in xMELP decrease both hands-on labor and turn-around time by a full day. B) Comparison of methylation levels as measured by MELP and xMELP. DNA from 10 primary AML samples was subjected to both MELP and xMELP. Methylation levels at 28 loci, measured as $\log_2([\text{HpaII}]/[\text{MspI}])$ normalized to the average methylation level at three control loci, was determined. Comparable methylation levels were obtained with the two methods at all loci examined.

The presently disclosed subject matter provides high-throughput methods for performing genomic DNA methylation assessments. The presently disclosed subject matter further provides methods for diagnosing a subject with a disease and/or disorder. In addition, the disclosed subject matter provides methods for determining the prognosis of a subject that has a disease and/or disorder.

Definitions

A "biological sample" or "sample," as used interchangeably herein, refers to a sample of biological material obtained from a subject including cells in culture, cell supernatants, cell lysates, serum, blood, plasma, bone marrow (biopsy and/or aspirate), biological fluid (e.g., blood, plasma, serum, stool, urine, lymphatic fluid, ascites, ductal lavage, nipple aspirate, saliva, broncho-alveolar lavage, tears and cerebrospinal fluid), and tissue samples. The source of the sample may be solid tissue (e.g., from a fresh, frozen, and/or preserved organ, tissue sample, biopsy or aspirate), blood or any blood constituents, bodily fluids (such as, e.g., urine, lymph, cerebral spinal fluid, amniotic fluid, peritoneal fluid, or interstitial fluid) or cells from the individual. In certain non-limiting embodiments, the biological sample is obtained from a tumor. In certain embodiments, the sample can be a "clinical sample," which is a sample derived from a patient. In certain embodiments, the biological sample can be a peripheral blood sample from a patient. In certain embodiments, the biological sample can be a bone marrow sample from a patient.

The term "patient" or "subject," as used interchangeably herein, refers to any warm-blooded animal, e.g., a human. Non-limiting examples of non-human subjects include non-human primates, dogs, cats, mice, rats, guinea pigs, rabbits, fowl, pigs, horses, cows, goats, sheep, etc.

As used herein, the terms "restriction endonucleases" and "restriction enzymes" refer to bacterial enzymes, each of which cut double-stranded DNA at or near a specific nucleotide sequence. DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring.

As used interchangeably herein, "methylation status" and "methylation level" refer to the presence, absence and/or quantity of methylation at a particular nucleotide, or nucleotides, within a DNA region, e.g., genomic DNA loci. The methylation status of a particular DNA sequence (e.g., within a genomic DNA loci) can indicate the methylation state of every base in the sequence or can indicate the methylation state of a subset of the base pairs (e.g., of cytosines) or the methylation state of one or more specific restriction enzyme recognition sequences within the sequence. In certain embodiments, the methylation status of multiple genomic loci can be used to determine a "methylation score" (M-score), as described below, for use in the prognostic and diagnostic methods of the presently disclosed subject matter.

The term "methylation," as used herein, refers to the presence of a methyl group added by the action of a DNA methyl transferase enzyme to a cytosine base or bases in a region of nucleic acid, e.g., genomic DNA.

The term "isolated" (e.g., isolated genomic DNA) refers to a biological component that has been substantially separated or purified away from other biological components in the cell of the organism in which the component naturally occurs, e.g., other chromosomal and extra-chromosomal DNA and RNA, proteins and organelles. Nucleic acids, e.g., DNA, that have been "isolated" include nucleic acids purified by standard purification methods.

DNA Methylation Detection

The presently disclosed subject matter provides for high-throughput methods for assessing the methylation status of one or more genomic DNA loci in a biological sample of a subject. In certain embodiments, the method of the present disclosure can be used to assess the methylation status of two or more, three or more, four or more, five or more, six or more, seven or more, eight or more, ten or more, twelve or more, fifteen or more, seventeen or more, twenty or more, twenty-five or more or thirty or more genomic loci. In certain embodiments, the method of the present disclosure can be used to assess the methylation status of about seventeen genomic loci.

The methods of the present disclosure include the detection of the methylation status of certain genomic DNA loci. The analyzed genomic DNA loci can include one or more genomic loci that exhibit differential methylation in a biological sample from a subject that has a disease and/or disorder compared to a reference sample. In certain embodiments, the reference sample can include a biological sample from a healthy subject or a healthy and/or unaffected biological sample from a subject that has the disease and/or disorder.

DNA Methylation Detection by Microsphere HELP (MELP)

In certain embodiments, the MELP method for determining the methylation status of a genomic DNA locus includes obtaining genomic DNA from a biological sample from a subject. The genomic DNA can be isolated from the biological sample by any method known in the art. For example, and not by way of limitation, genomic DNA can be isolated from a biological sample by using the phenol-chloroform DNA extraction method. Commercially available kits can also be conveniently used for this purpose in accordance with the instructions provided by their manufacturers, such kits are available from the following manufacturers: Invitrogen, San Diego, Calif.; Stratagene, La Jolla, Calif. In certain embodiments, genomic DNA can be isolated from a biological sample using commercially available kits (e.g., PureLink® Genomic DNA kit from Life Technologies).

The method for analyzing the methylation status of one or more genomic DNA loci can further include fragmenting the genomic DNA by digesting the DNA with one or more restriction enzymes. In certain embodiments, the genomic DNA can be digested by a methylation-insensitive and/or methylation-sensitive restriction enzyme. A methylation-sensitive restriction enzyme is a restriction enzyme that cuts DNA if its recognition sequence is unmethylated. A methylation-insensitive enzyme is a restriction enzyme that cuts DNA independent of the methylation status of its recognition sequence, i.e., the enzyme will cut the restriction site if it is methylated or unmethylated. Non-limiting examples of methylation-sensitive restriction enzymes include AatII, AcciI, AclI, Aor13HI, AgeI-HF®, AscI, AsiSI, AvaI, BspT104I, BssHII, DpnII, EagI, HaeII, HgaI, HhaI, HpaII, KasI, MluCI, NotI, NruI, Sau3AI, SalI-HF®, ScrFI, SfoI, SmaI, SnaBI and ZraI.

In certain embodiments, the methylation-insensitive and the methylation-sensitive restriction enzyme used in the disclosed method recognize the same restriction site. In certain embodiments, the restriction enzyme recognition site is 5'-CCGG-3'. For example, and not by way of limitation, the methylation-insensitive restriction enzyme can be MspI and/or the methylation-sensitive restriction enzyme can be HpaII. The presence of methylated nucleotides (e.g., cytosines) in the genome can result in the methylation-sensitive restriction enzyme generating fewer and longer fragments than the methylation-insensitive restriction enzyme, thereby allowing analysis of the methylation status of various genomic DNA loci by comparison of the quantity of the fragments received by MspI digestion to the quantity of fragments received by HpaII digestion for a particular genomic DNA loci.

The genomic DNA fragments generated by the contact of the isolated genomic DNA with a methylation-insensitive and/or methylation-sensitive restriction enzyme can be ligated to DNA linkers to allow for amplification of the genomic DNA fragments. In certain embodiments, the linkers can be oligonucleotides of sufficient length to hybridize to the DNA fragments. For example, and not by way of limitation, the length of each linker can be greater than about 10 nucleotides, greater than about 15 nucleotides, greater than about 20 nucleotides or greater than about 25 nucleotides. In certain embodiments, the linker can include a primer site for PCR amplification of the DNA fragments. In certain embodiments, the linkers for use in the present disclosure can include double stranded DNA that has 5' overhangs. In certain embodiments, the method includes purification of the DNA fragments from the restriction enzymes used in the digestion step followed by ligation of the linkers to the DNA fragments.

The methods for analyzing the methylation status of one or more genomic DNA loci can further include amplification of the DNA fragments. Amplification of the DNA fragments can be performed by any method known in the art. For example, and not by way of limitation, polymerase chain reaction (PCR) can be performed to amplify the genomic DNA fragments. PCR can include annealing nucleic acid primers to a complementary target DNA strand by nucleic acid hybridization to form a hybrid between the primer and the target DNA strand, and then extend the primer along the target DNA strand by a DNA polymerase enzyme, e.g., Taq Polymerase. Alternatively and/or additionally, the linkers ligated to the DNA fragments, as discussed above, can serve as primers for the PCR reaction. For example, the JHpaII 24 nucleic acid strand of the double-stranded linkers formed by the annealing of the JHpaII 12 primer and the JHpaII 24 primer can serve as the primer for the PCR reaction.

The primers used in the methods of the disclosure can be, for example, DNA oligonucleotides having 10 nucleotides or more in length. In certain embodiments, the primers can include DNA oligonucleotides that are about 15, about 20, about 25, about 30 or about 50 nucleotides or more in length. In certain embodiments, the primer for use in the PCR reaction can include JHpaII 24, disclosed below. The oligonucleotide primers of the invention can be prepared using any suitable method, such as conventional phosphotriester and phosphodiester methods or automated embodiments thereof. The primers can be added to the amplification method in any amount effective for amplifying the target nucleic acid present in the sample.

Non-limiting examples of primers and/or linkers that can be used in the methods of the disclosed subject matter are as follows:

```
                                          (SEQ ID NO: 1)
JHpaII 12:  5'-CGGCTGTTCATG-3'

(SEQ ID NO: 2)
JHpaII 24:  5'-CGACGTCGACTATCCATGAACAGC-3'
```

For example, the JHpaII 12 primer and the JHpaII 24 primer can be annealed to serve as the linkers described above.

The method can further include quantifying the amount of amplified DNA fragments, e.g., PCR amplicons. In certain embodiments, quantification of the PCR amplicons can include hybridizing the PCR amplicons to microspheres, fluorescently labeling the amplicons and performing flow cytometry. The methods of the disclosed subject matter do not include the use of microarrays to quantify the PCR amplicons. In certain embodiments, the microspheres can be about 5 microns in size. In certain embodiments, the microspheres can be made of polystyrene. A non-limiting example of microspheres that can be used in the presently disclosed subject matter is MicroPlex® microspheres from Luminex Corp. (Austin, Tex.). For example, and not by way of limitation, the QuantiGene Plex 2.0 Assay (Affymetrix, Santa Clara, Calif.) can be used to quantify the PCR amplicons. In certain embodiments, the PCR amplicons can be hybridized to locus-specific oligonucleotide probes to form PCR amplicon/locus-specific probe complexes followed by hybridization of the complexes to the microspheres. In certain embodiments, the locus-specific oligonucleotide probes can be conjugated to the microspheres followed by hybridization of the probe with the PCR amplicon to form PCR amplicon/locus-specific probe complexes. The nucleic acid sequence of the locus-specific probe can correspond to the sequence of the genomic locus that is being analyzed by the disclosed DNA methylation detection method.

The amplicon/locus-specific probe complexes hybridized to the microspheres can be fluorescently labeled. In certain embodiments, the locus-specific probe can be labeled directly, e.g., conjugated, or indirectly to a detectable label. Non-limiting examples of detectable labels include fluorescent labels (e.g., fluorophores), radiolabels (e.g., $^3$H, $^{125}$I, $^{35}$S, $^{14}$C, $^{32}$P or $^{33}$P), enzymes (e.g., LacZ, horseradish peroxidase, alkaline phosphatase) and nucleic acid intercalators (e.g., ethidium bromide). Non-limiting examples of fluorophores include rhodamine, fluorescein, green fluorescent protein, luciferase, Cy3, Cy5, phycoerythrin or ROX. Alternatively or additionally, fluorescent labeling of the amplicon/locus-specific probe complexes can be performed by hybridization of the complexes to a label oligonucleotide probe. For example, and not by way of limitation, the locus-specific probe can include biotinylated nucleotides that bind to a fluorophore-conjugated streptavidin compound. In certain embodiments, the fluorophore-conjugated streptavidin compound can be phycoerythrin-streptavidin.

In certain embodiments, the methylation status and/or level of an individual genomic locus can be determined by the comparing the amount of amplified DNA fragments (e.g., PCR amplicons) in the digest of the methylation-insensitive restriction enzyme for a particular locus to the amount of DNA fragments (e.g., PCR amplicons) in the digest of the methylation-sensitive restriction enzyme for the same particular locus (e.g., identified during the detection method by the use of the locus-specific probe disclosed above). The comparison can be normalized to the methylation level of one or more control genomic DNA loci. If more than one control genomic locus is used for normalization, the average methylation status of the two or more genomic loci can be used for normalization. In certain embodiments, the control genomic loci are loci that are typically unmethylated in the biological sample being used in the disclosed methods.

For example, and not by way of limitation, the methylation level can be determined using the following formula:

$$\log_2(\text{HpaII/MspI}) \qquad \text{[Formula 1]}$$

wherein, the result of Formula I can be normalized to the methylation level of the control genomic DNA loci analyzed.

In certain embodiments, the methylation levels of two or more genomic DNA loci can be represented in a methylation outcome score (M-score or MS). In certain embodiments, the M-score is determined by the following formula:

$$MS = a(L1) + b(L2) + c(L3) + d(L4) \qquad \text{[Formula 2]}$$

where L#is the methylation level (i.e., normalized HpaII/MspI ratio) at each locus, and the associated constant (a, b, c) is the weighting factor, as determined by a training algorithm (SuperPC; http://statweb.stanford.edu/wtibs/superpc).

The methods of the present disclosure include the detection of the methylation status of certain genomic DNA loci. The analyzed genomic DNA loci can include one or more genomic loci that exhibit differential methylation in a biological sample from a subject that has a disease and/or disorder compared to a reference sample. In certain embodiments, the reference sample can include a biological sample from a healthy subject or a healthy and/or unaffected biological sample from a subject that has the disease and/or disorder.

DNA Methylation Detection by Expedited MELP (xMELP)

In certain embodiments, the xMELP method for determining the methylation status of a genomic DNA locus includes obtaining genomic DNA from a biological sample from a subject, as disclosed above. The method can further include fragmenting the genomic DNA by digesting the DNA with one or more restriction enzymes. In certain embodiments, the genomic DNA can be digested by a methylation-insensitive and/or methylation-sensitive restriction enzyme, described above. In certain embodiments, the methylation-insensitive restriction enzyme can include MspI and/or the methylation-sensitive restriction enzyme can include HpaII. The genomic DNA fragments generated by the contact of the isolated genomic DNA with a methylation-insensitive and/or methylation-sensitive restriction enzyme can be ligated to nucleic acid linkers to allow amplification of the genomic DNA fragments, as disclosed above.

In certain embodiments, the linkers used in the disclosed method can be annealed pairs of nucleic acid primers. Non-limiting examples of primers and/or linkers that can be used or modified to be used in the methods of the disclosed subject matter are as follows:

```
                                          (SEQ ID NO: 3)
JHpaII 12XXXX: 5'-CGCCTGTTCATG-3'

(SEQ ID NO: 4)
JHpaII 24XXXX: 5'-CGACGTCGACTATCCATGAACAGG-3'
```

For example, the JHpaII 12XXXX primer and the JHpaII 24XXXX primer can be annealed to serve as the linkers described above.

Amplification of the DNA fragments can be performed by any method known in the art. In certain embodiments, PCR can be performed to amplify the genomic DNA fragments using nucleic acid primers described above. The primers used in the methods of the disclosure can be, for example, DNA oligonucleotides having 10 nucleotides or more in length. In certain embodiments, the primers can include DNA oligonucleotides that are about 15, about 20, about 25, about 30 or about 50 nucleotides or more in length. In certain embodiments, the primer for use in the PCR reaction can include JHpaII 24XXXX, disclosed below. Alternatively and/or additionally, the linkers ligated to the DNA fragments can serve as primers for the PCR reaction. For example, the JHpaII 24XXXX nucleic acid strand of the double-stranded linkers formed by the annealing of the JHpaII 12XXXX primer and the JHpaII 24XXXX primer can serve as the primer for the PCR reaction.

In certain embodiments, the digestion of the genomic DNA by restriction enzymes and the ligation of the DNA fragments to the linkers can be performed in a single reaction (see FIG. 1A). In comparison to the MELP DNA methylation detection method disclosed above, the nucleic acid sequences of the JHpaII 12XXXX primer and the JHpaII 24XXXX primer allows the performance of the digestion step and ligation step into a single reaction. For example, in the MELP method, the use of annealed JHpaII 12 primers and the JHpaII 24 primers, as the linkers in the MELP assay, results in the formation of a HpaII/MspI restriction site during the ligation step. The presence of this restriction site requires the purification of the genomic DNA fragments to remove the restriction enzymes used in the digestion step from the sample of DNA fragments prior to the ligating of the linkers to the DNA fragments. In contrast, the JHpaII 12XXXX primer and the JHpaII 24XXXX primer, when annealed and used as linkers, do not form a HpaII/MspI restriction site and allows the exclusion of the intermediate DNA purification step from between the digestion and ligation steps, thereby permitting the combination of the digestion step and ligation step into a single reaction.

The combination of the digestion and ligation reaction in a single reaction reduces the amount of time needed to perform the high-throughput DNA methylation assessment, and allows rapid turn-around time of the results of the DNA methylation analysis in a clinical setting. For example, and not by way of limitation, the xMELP DNA methylation assessment method disclosed herein can be performed within about 6 hours to about 48 hours or within about 12 hours to about 48 hours. The timeframe of the xMELP DNA methylation assessment method is significantly shorter than the MELP DNA methylation assessment method, disclosed above, which can take from about 60 to about 72 hours to complete.

In certain embodiments, the single digestion and ligation reaction can include genomic DNA, annealed oligonucleotide primers, ATP, DNA ligase, a restriction enzyme, e.g., MspI or HpaII, and the appropriate buffers for the ligase and restriction enzymes. In certain embodiments, the single digestion and ligation reaction can be carried out at a temperature of about 25° C. for about 12 hours.

The method can further include quantifying the amount of amplified DNA fragments, e.g., PCR amplicons. In certain embodiments, quantification of the PCR amplicons can include hybridizing the PCR amplicons to microspheres, fluorescently labeling the amplicons and performing flow cytometry, as disclosed above. In certain embodiments, the methylation status (e.g., level) of each individual genomic locus analyzed can then be determined by the comparing the amount of DNA fragments (e.g., PCR amplicons) in the digest of the methylation-insensitive restriction enzyme for a particular locus to the amount of DNA fragments in the digest of the methylation-sensitive restriction enzyme for the same particular locus (e.g., PCR amplicons), normalized to the methylation level of the control genomic DNA loci. As discussed above, the methylation level can be determined using Formula 1.

In certain embodiments, the xMELP method for assessment of genomic DNA methylation can analyze the methylation status of individual genomic DNA loci in small quantities of genomic DNA that has been isolated from a biological sample. For example, and not by way of limitation, the xMELP method can be used to perform DNA methylation assessment on samples that contain low levels of genomic DNA, such as about 2 ng of genomic DNA.

In comparison to the MELP assay disclosed above, the xMELP assay provides a more uniform quality control metric. For example, and not by way of limitation, analysis of the methylation level of multiple genomic loci allowed the determination of a quality control cutoff. In certain embodiments, the quality control cutoff can be the control loci value<100.

DNA Methylation Detection Method for Acute Myeloid Leukemia (AML)

The present disclosure provides high-throughput methods for identifying AML in a biological sample of a subject. The high-throughput method includes determining the methylation status of one or more genomic DNA loci in the biological sample using a DNA methylation detection method disclosed herein.

In certain embodiments, the one or more genomic DNA loci can include, but are not limited to, Chr 17: 2208021 to 2208391 (MSPI0406S00783415); Chr 20: 32274469 to 32275009 (MSP10406S00920592); Chr 6: 3024925 to 3025589 (MSP10406S00304798); Chr 3: 129274773 to 129275235 (MSPI0406S00196536); Chr 14: 105860849 to 105861218 (MSPI0406S00697563); Chr 1: 11723172 to 11723834 (MSPI0406S00011246); Chr 19: 1924052 to 1924259 (MSPI0406S00861109); Chr 6: 108615428 to 108615973 (MSPI0406S00333894); Chr 16: 30538940 to 30539797 (MSP10406S00754805); Chr 12: 53661106 to 53661621 (MSPI0406S00613804); Chr 3: 48601900 to 48602237 (MSPI0406S00176846); Chr 15: 65810129 to 65810776 (MSP10406S00715593); Chr 14: 106354882 to 106355276 (MSPI0406S00698115); Chr 12: 6233715 to 6234255 (MSP10406S00600078); Chr 20: 11899205 to 11899843 (MSPI0406S00914183); Chr 15: 50838542 to 50839225 (MSP10406S00710190); Chr 3: 8542436 to 8543339 (MSPI0406S00163833); Chr 16: 68345197 to 68345691 (MSPI0406S00765490); Chr 20: 11898849 to 11899205 (MSP10406S00914182); Chr 20: 11898555 to 11898849 (MSPI0406S00914181); Chr X: 48795887 to 48797005 (MSPI0406S00997890); Chr 18: 5293969 to 5294770 (MSPI0406S00838340); Chr 2: 158114266 to 158115184 (MSPI0406S00136939); Chr 14: 24867489 to 24867729 (MSPI0406S00669709); Chr 1: 32739167 to 32739750 (MSPI0406S00027418); Chr 11: 118763110 to 118763426 (MSPI0406S00589152); Chr 20: 814970 to 815202 (MSPI0406S00910305); Chr 15: 45003463 to 45004002 (MSPI0406S00708912); or combinations thereof.

In certain embodiments, the one or more genomic DNA loci can include, but are not limited to Chr 17: 2208021 to 2208391 (MSPI0406S00783415); Chr 3: 129274773 to 129275235 (MSPI0406S00196536); Chr 1: 11723172 to 11723834 (MSPI0406S00011246); Chr 19: 1924052 to 1924259 (MSPI0406S00861109); Chr 6: 108615428 to 108615973 (MSPI0406S00333894); Chr 16: 30538940 to 30539797 (MSPI0406S00754805); Chr 12: 53661106 to 53661621 (MSPI0406S00613804); Chr 15: 65810129 to 65810776 (MSPI0406S00715593); Chr 14: 106354882 to 106355276 (MSPI0406S00698115); Chr 12: 6233715 to 6234255 (MSP10406S00600078); Chr 20: 11899205 to 11899843 (MSPI0406S00914183); Chr 15: 50838542 to 50839225 (MSPI0406S00710190); Chr 3: 8542436 to 8543339 (MSPI0406S00163833); Chr 16: 68345197 to 68345691 (MSPI0406S00765490); Chr 20: 11898849 to 11899205 (MSP10406S00914182); Chr 20: 11898555 to 11898849 (MSPI0406S00914181); Chr 2: 158114266 to 158115184 (MSP10406S00136939); or combinations thereof.

In certain embodiments, the one or more genomic DNA loci can include one or more of the genomic loci listed in Tables 1 and 2.

In certain embodiments, the method can further include detecting the methylation status of one or more genomic DNA loci as a control. For example, and not by way of limitation, the one or more control genomic DNA loci can include Chr 6: 34856156 to 34857019 (MSPI0406S00318682); Chr 13: 53028642 to 53029495 (MSPI0406S00653944); Chr 19: 37958559 to 37958860 (MSPI0406S00890278); or combinations thereof.

Diagnostic, Prognostic and Therapeutic Methods

The present disclosure provides diagnostic and prognostic methods for diseases and/or disorders that are characterized by differential methylation of genomic sequences, e.g., differential methylation of cytosines (CpG dinucleotide sequences).

In certain embodiments, the present disclosure provides diagnostic methods for determining the presence of a disease and/or disorder in a subject by assessing the DNA methylation profiles characteristically associated with the disease and/or disorder. For example, and not by way of limitation, the diagnostic method can include (a) obtaining a biological sample from the subject; (b) determining the methylation status of one or more genomic DNA loci in one or more cells of the biological sample; and (c) diagnosing the disease and/or disorder in the subject, wherein the methylation status of the one or more genomic DNA loci indicates the presence of the disease and/or disorder in the subject. In certain embodiments, the diagnosis can be based on a methylation score (M-score) that is derived from the methylation status of all the target genomic DNA loci analyzed. In certain embodiments, the presently disclosed subject matter can be used for the diagnosis and/or prognosis of diseases and/or disorders such as, but not limited to, cancer, autoimmune diseases, coronary artery disease and aging.

In certain embodiments, the present disclosure provides diagnostic methods for determining the presence of cancer in a subject by assessing the DNA methylation profiles characteristically associated with the cancer. For example, and not by way of limitation, the diagnostic method can include (a) obtaining a biological sample from the subject; (b) determining the methylation status of one or more genomic DNA loci in one or more cells of the biological sample; and (c) diagnosing cancer in the subject, wherein the methylation status of the one or more genomic DNA loci indicates the presence of cancer in the subject. In certain embodiments, the presently disclosed subject matter can be used for the diagnosis and/or prognosis of cancers such as, but not limited to, melanoma, non-small cell lung cancer, glioblastoma, ovarian cancer, leukemia and lymphoblastic leukemia.

In certain embodiments, the present disclosure provides prognostic methods for determining the prognosis of a subject that has a disease and/or disorder by assessing the DNA methylation profiles characteristically associated with the disease and/or disorder. For example, and not by way of limitation, the prognostic method can include (a) obtaining a biological sample from the subject; (b) determining the methylation status of one or more target genomic DNA loci in one or more cells of the biological sample; and (c) providing a disease and/or disorder prognosis based on the methylation status of the one or more genomic DNA loci in the subject. In certain embodiments, the prognosis can be based on a methylation score (M-score) that is derived from the methylation status of all the target genomic DNA loci analyzed.

In certain embodiments, the present disclosure provides prognostic methods for determining the prognosis of a subject that has cancer by assessing the DNA methylation profiles characteristically associated with the cancer. For example, and not by way of limitation, the prognostic method can include (a) obtaining a biological sample from the subject; (b) determining the methylation status of one or more target genomic DNA loci in one or more cells of the biological sample; and (c) providing a cancer prognosis based on the methylation status of the one or more genomic DNA loci in the subject.

In certain embodiments, the methods for detection of the methylation status of one or more target genomic DNA loci can be used to monitor the response in a subject to prophylactic or therapeutic treatment (for example, chemotherapy to reduce tumor cell growth and/or metastasis). In certain non-limiting embodiments, the disclosed subject matter further provides a method of treatment including measuring the methylation status of one or more target genomic DNA loci in a biological sample of a subject at a first timepoint, administering a therapeutic agent, re-measuring the methylation status of the one or more target genomic DNA loci at a second timepoint, comparing the results of the first and second measurements and optionally modifying the treatment regimen based on the comparison.

In certain embodiments, the first timepoint is prior to an administration of the therapeutic agent, and the second timepoint is after said administration of the therapeutic agent. In certain embodiments, the first timepoint is prior to the administration of the therapeutic agent to the subject for the first time. In certain embodiments, the dose (defined as the quantity of therapeutic agent administered at any one administration) is increased or decreased in response to the comparison. In certain embodiments, the dosing interval (defined as the time between successive administrations) can be increased or decreased in response to the comparison, including total discontinuation of treatment. In addition, the method of the present disclosure can be used to determine the efficacy of the therapeutic treatment, wherein a change in the methylation status of certain genomic DNA loci in a biological sample of a subject can indicate that the therapeutic treatment regimen can be reduced or stopped.

In certain embodiments, the information provided by the methods described herein can be used by a physician in determining the most effective course of treatment (e.g., preventative or therapeutic) for the subject. A course of treatment refers to the measures taken for a patient after the prognosis or the assessment of increased risk for development of a disease and/or disorder is made. For example, when a subject is identified to have an increased risk of developing cancer, the physician can determine whether frequent monitoring for DNA methylation changes can be performed as a prophylactic measure. Also, when a subject is diagnosed with cancer (e.g., based on the presence of a DNA methylation pattern in a sample from a subject), it can be advantageous to follow such detection with a biopsy, surgical treatment, chemotherapy, radiation, immunotherapy, biological modifier therapy, gene therapy, vaccines and the like, or adjust the span of time during which the patient is treated.

The presently disclosed subject matter further provides assays and/or methods for determining the DNA methylation status of target genomic loci that correlates with the presence, absence and/or severity of a disease and/or disorder. In certain embodiments, a method can include comparing the methylation status of genomic DNA loci in a biological sample from a subject that has a disease and/or disorder to the methylation status of genomic DNA loci in a biological sample from a healthy subject to determine the methylation pattern, as disclosed above, that correlates with the presence of the disease and/or disorder. In certain embodiments, a method can include comparing the methylation status of genomic DNA loci in a biological sample from a subject that has a disease and/or disorder at an early stage to the methylation status of genomic DNA loci in a biological sample from a subject that has the disease and/or disorder at a late stage, as disclosed above, to determine the methylation pattern that correlates with the different stages of the disease and/or disorder.

Prognostic, Therapeutic and Diagnostic Methods for AML

The presently disclosed subject matter provides diagnostic and prognostic methods for AML that includes determining the methylation status of one or more genomic DNA loci in a biological sample of a subject.

In certain embodiments, a method for diagnosing AML in a subject includes (a) obtaining a biological sample from the subject; (b) determining the methylation status of one or more genomic DNA loci in one or more cells of the biological sample; and (c) diagnosing AML in the subject, wherein the methylation status of the one or more genomic DNA loci indicates the presence of AML in the subject.

In certain embodiments, a prognostic method for determining the prognosis of a subject that has AML includes (a) obtaining a biological sample from the subject; (b) determining the methylation status of one or more target genomic DNA loci in one or more cells of the biological sample; and (c) providing an AML prognosis based on the methylation status of the one or more genomic DNA loci in the subject.

In certain embodiments, the diagnosis and/or prognosis can be based on a methylation score (M-score) that is derived from the methylation status of one or more of the target genomic DNA loci analyzed. In certain embodiments, a lower M-score indicates a better AML prognosis. For example, and not by way of limitation, an M-score less than about 90, less than about 89, less than about 88, less than about 87, less than about 86, less than about 85, less than about 84, less than about 83, less than about 82, less than about 81 or less than about 80 indicates a better AML prognosis than a higher M-score. In certain embodiments, an M-score greater than about 91, greater than about 92, greater than about 93, greater than about 94, greater than about 95, greater than about 96, greater than about 97, greater than about 98, greater than about 99 or greater than about 100 indicates a worse AML prognosis than a lower M-score. In certain embodiments, an M-score less than about 90, less than about 89, less than about 88, less than about 87, less than about 86, less than about 85, less than about 84, less than about 83, less than about 82, less than about 81 or less than about 80 indicates a better AML prognosis than an M-score greater than about 91, greater than about 92, greater than about 93, greater than about 94, greater than about 95, greater than about 96, greater than about 97, greater than about 98, greater than about 99 or greater than about 100. In certain embodiments, an M-score less than about 86 indicates a better AML prognosis than an M-score greater than or equal to about 86.

In certain embodiments, an M-score less than or equal to about 86 indicates a better AML prognosis than an M-score greater than about 86. In certain embodiments, an M-score less than about 89 indicates a better AML prognosis than an M-score greater than or equal to about 89. In certain embodiments, an M-score less than or equal to about 89 indicates a better AML prognosis than an M-score greater than about 89.

In certain embodiments, the diagnosis and/or prognostic method for AML can include the analysis of the methylation status of two or more, three or more, four or more, five or more, six or more, seven or more, eight or more, ten or more, twelve or more, fifteen or more, seventeen or more, twenty or more, twenty-five or more or thirty or more genomic loci. In certain embodiments, the analysis of the methylation status of the two or more genomic loci can be performed simultaneously. In certain embodiments, the diagnosis and/or prognostic method for AML can include the analysis of the methylation status of seventeen different genomic loci.

The detection of the one or more genomic loci can be performing using the DNA methylation detection methods disclosed herein, or can be performed using any of the DNA detection methods known in the art. In certain embodiments, the diagnostic and/or prognostic methods can include determining the methylation status of one or more genomic DNA loci by the DNA methylation detection method MELP, disclosed above. In certain embodiments, the diagnostic and/or prognostic methods can include determining the methylation status of one or more genomic DNA loci by the DNA methylation detection method xMELP, disclosed above.

In certain embodiments, the one or more genomic DNA loci can include, but are not limited to, Chr 17: 2208021 to 2208391 (MSPI0406S00783415); Chr 20: 32274469 to 32275009 (MSP10406S00920592); Chr 6: 3024925 to 3025589 (MSPI0406S00304798); Chr 3: 129274773 to 129275235 (MSP10406S00196536); Chr 14: 105860849 to 105861218 (MSP10406S00697563); Chr 1: 11723172 to 11723834 (MSPI0406S00011246); Chr 19: 1924052 to 1924259 (MSP10406S00861109); Chr 6: 108615428 to 108615973 (MSPI0406S00333894); Chr 16: 30538940 to 30539797 (MSP10406S00754805); Chr 12: 53661106 to 53661621 (MSPI0406S00613804); Chr 3: 48601900 to 48602237 (MSP10406S00176846); Chr 15: 65810129 to 65810776 (MSP10406S00715593); Chr 14: 106354882 to 106355276 (MSPI0406S00698115); Chr 12: 6233715 to 6234255 (MSPI0406S00600078); Chr 20: 11899205 to 11899843 (MSP10406S00914183); Chr 15: 50838542 to 50839225 (MSPI0406S00710190); Chr 3: 8542436 to 8543339 (MSPI0406S00163833); Chr 16: 68345197 to 68345691 (MSP10406S00765490); Chr 20: 11898849 to 11899205 (MSP10406S00914182); Chr 20: 11898555 to 11898849 (MSPI0406S00914181); Chr X: 48795887 to 48797005 (MSP10406S00997890); Chr 18: 5293969 to 5294770 (MSP10406S00838340); Chr 2: 158114266 to 158115184 (MSPI0406S00136939); Chr 14: 24867489 to 24867729 (MSPI0406S00669709); Chr 1:32739167 to 32739750 (MSP10406S00027418); Chr 11: 118763110 to 118763426 (MSP10406S00589152); Chr 20: 814970 to 815202 (MSPI0406S00910305); Chr 15: 45003463 to 45004002 (MSPI0406S00708912); or combinations thereof.

In certain embodiments, the one or more genomic DNA loci can include, but are not limited to Chr 17: 2208021 to 2208391 (MSPI0406S00783415); Chr 3: 129274773 to 129275235 (MSP10406S00196536); Chr 1: 11723172 to 11723834 (MSPI0406S00011246); Chr 19: 1924052 to 1924259 (MSP10406S00861109); Chr 6: 108615428 to 108615973 (MSPI0406S00333894); Chr 16: 30538940 to 30539797 (MSP10406S00754805); Chr 12: 53661106 to 53661621 (MSPI0406S00613804); Chr 15: 65810129 to 65810776 (MSPI0406S00715593); Chr 14: 106354882 to 106355276 (MSPI0406S00698115); Chr 12: 6233715 to 6234255 (MSPI0406S00600078); Chr 20: 11899205 to 11899843 (MSP10406S00914183); Chr 15: 50838542 to 50839225 (MSP10406S00710190); Chr 3: 8542436 to 8543339 (MSPI0406S00163833); Chr 16: 68345197 to 68345691 (MSP10406S00765490); Chr 20: 11898849 to 11899205 (MSP10406S00914182); Chr 20: 11898555 to 11898849 (MSPI0406S00914181); Chr 2: 158114266 to 158115184 (MSP10406S00136939); or combinations thereof.

In certain embodiments, the one or more genomic DNA loci can include one or more of the genomic loci listed in Tables 1 and 2.

In certain embodiments, the method can further include detecting the methylation status of genomic DNA loci as a control. For example, and not by way of limitation, control genomic DNA loci can include Chr 6: 34856156 to 34857019 (MSPI0406S00318682); Chr 13: 53028642 to 53029495 (MSPI0406S00653944); Chr 19: 37958559 to 37958860 (MSPI0406S00890278); or combinations thereof.

In certain embodiments, the method can further include determining and/or evaluating additional prognostic criteria. For example, and not by way of limitation, additional prognostic criteria can include white blood cell (WBC) count, age, sex, cytogenetic risk, complete remission (CR) status, minimal residual disease (MRD) and the mutational status of genes such as DNMT3A, IDH1, FLT3-ITD and/or NPM1. Additional non-limiting examples of genes that can provide prognostic information by analysis of their mutational status include ASXL1, ATM, BRAF, CBL, DNMT3A, ETV6, EZH2, IDH1, IDH2, JAK2, KIT, KLHL6, KRAS, NRAS, PTEN, PTPN11, PHF6, RUNX1, SF3B1, TET2, TP53 and WT1. In certain embodiments, these prognostic criteria can be combined with the M-score to determine the prognosis of a subject having AML. For example, and not by way of limitation, the M-score can be combined with the cytogenetic risk of the patient to generate a multivariable prognostic model. In certain embodiments, the M-score can be combined with age and/or the mutational status of genes, disclosed herein, such as DNMT3A, IDH1, FLT3-ITD and/or NMP1 to generate a multivariable prognostic model for determining the prognosis of a subject that has AML.

In certain embodiments, the methods for detection of the methylation status of one or more target genomic DNA loci can be used to monitor the response in a subject that has AML to prophylactic or therapeutic treatment. In certain embodiments, the disclosed subject matter further provides a method of treating AML that can include measuring the methylation status of one or more target genomic DNA loci in a biological sample of a subject at a first timepoint, administering a therapeutic agent, re-measuring the methylation status of the one or more target genomic DNA loci at a second timepoint, comparing the results of the first and second measurements and optionally modifying the treatment regimen based on the comparison.

In certain embodiments, the information provided by the methods described herein can be used by a physician in determining the most effective course of treatment (e.g., preventative or therapeutic) for the subject, e.g., to produce an anti-cancer effect. An "anti-cancer effect" refers to one or more of a reduction in aggregate cancer cell mass, a reduction in cancer cell growth rate, a reduction in cancer cell proliferation, a reduction in tumor mass, a reduction in tumor volume, a reduction in tumor cell proliferation, a reduction in tumor growth rate, and/or a reduction in tumor metastasis. In certain embodiments, an anti-cancer effect can refer to remission, a complete response, a partial response, a stable disease (without progression or relapse), a response with a later relapse or progression-free survival in a patient diagnosed with cancer.

In certain embodiments, the treatment of a subject that has AML can be informed by the M-score obtained from the disclosed methods. For example, and not by way of limitation, if a subject that has AML is determined to have a high M-score (e.g., an M-score greater than about 86) by using the methods disclosed herein, high-doses of a chemotherapeutic agent (e.g., daunorubicin administered at a concentration greater than or equal to about 90 mg/m$^2$ daily (e.g., for about 3 days)) can be predicted to have superior anti-cancer effect in the subject than lower doses of a chemotherapeutic agent (e.g., daunorubicin administered at a concentration less than or equal to about 45 mg/m$^2$ daily (e.g., for about 3 days)). In certain embodiments, if a subject that has AML is determined to have a high M-score by using the methods disclosed herein, two cycles of induction chemotherapy (i.e., chemotherapy given to induce remission) will likely have an anti-cancer effect in the subject. For example, and not by way of limitation, the induction chemotherapy regimen can include anthracycline and/or cytarabine.

Reports, Programmed Computers and Systems

The results of a test (e.g., a subject's DNA methylation score and/or the methylation status of individual genomic DNA loci), based on performing the disclosed methods, and/or any other information pertaining to a test, can be referred to herein as a "report." A tangible report can optionally be generated as part of a testing process (which can be interchangeably referred to herein as "reporting," or as "providing" a report, "producing" a report or "generating" a report).

Examples of tangible reports can include, but are not limited to, reports in paper (such as computer-generated printouts of test results) or equivalent formats and reports stored on computer readable medium (such as a CD, USB flash drive or other removable storage device, computer hard drive, or computer network server, etc.). Reports, particularly those stored on computer readable medium, can be part of a database, which can optionally be accessible via the internet (such as a database of patient records or genetic information stored on a computer network server, which can be a "secure database" that has security features that limit access to the report, such as to allow only the patient and the patient's medical practitioners to view the report while preventing other unauthorized individuals from viewing the report, for example). In addition to, or as an alternative to, generating a tangible report, reports can also be displayed on a computer screen (or the display of another electronic device or instrument).

A report can include, for example, an individual's diagnosis, such as AML, or can just include a patient's DNA methylation results (for example, a report on computer readable medium such as a network server can include hyperlink(s) to one or more journal publications or websites that describe the medical/biological implications, such as the presence of a particular type of cancer, for individuals having certain DNA methylation patterns). Thus, for example, the report can include disease risk or other medical/biological significance (e.g., drug responsiveness, suggested prophylactic treatment, etc.) as well as optionally also including the DNA methylation results, or the report can just include DNA methylation information without including disease risk or other medical/biological significance (such that an individual viewing the report can use the DNA methylation results to determine the medical/biological significance from a source outside of the report itself, such as from a medical practitioner, publication, website, etc., which can optionally be linked to the report such as by a hyperlink).

A report can further be "transmitted" or "communicated" (these terms can be used herein interchangeably), such as to the individual who was tested, a medical practitioner (e.g., a doctor, nurse, clinical laboratory practitioner, genetic counselor, etc.), a healthcare organization, a clinical laboratory and/or any other party or requester intended to view or possess the report. The act of "transmitting" or "communicating" a report can be by any means known in the art, based on the format of the report. Furthermore, "transmitting" or "communicating" a report can include delivering a report ("pushing") and/or retrieving ("pulling") a report. For example, reports can be transmitted/communicated by various means, including being physically transferred between parties (such as for reports in paper format) such as by being physically delivered from one party to another, or by being transmitted electronically or in signal form (e.g., via e-mail or over the internet, by facsimile and/or by any wired or wireless communication methods known in the art) such as by being retrieved from a database stored on a computer network server, etc.

In certain embodiments, the disclosed subject matter provides computers (or other apparatus/devices such as biomedical devices or laboratory instrumentation) programmed to carry out the methods described herein. For example, in certain embodiments, the disclosed subject matter provides a computer programmed to receive (i.e., as input) the methylation level at a particular genomic locus, and provide (i.e., as output) the risk of disease or other result (e.g., disease diagnosis or prognosis, drug responsiveness, etc.) based on methylation level at certain genomic DNA loci. Such output (e.g., communication of disease risk, disease diagnosis or prognosis, drug responsiveness, etc.) can be, for example, in the form of a report on computer readable medium, printed in paper form, and/or displayed on a computer screen or other display.

Certain further embodiments of the disclosed subject matter provide a system for determining a diagnosis or prognosis. Certain exemplary systems include an integrated "loop" in which an individual (or their medical practitioner) requests a determination of such individual's cancer risk (or drug response), this determination is carried out by testing a sample from the individual, and then the results of this determination are provided back to the requester. For example, in certain systems, a sample is obtained from an individual for testing (the sample can be obtained by the individual or, for example, by a medical practitioner), the sample is submitted to a laboratory (or other facility) for testing (e.g., determining the methylation status level at a genomic locus), and then the results of the testing are sent to the patient (which optionally can be done by first sending the results to an intermediary, such as a medical practitioner, who then provides or otherwise conveys the results to the individual and/or acts on the results), thereby forming an integrated loop system for determining an individual's cancer risk (or drug response, etc.). The portions of the system in which the results are transmitted (e.g., between any of a testing facility, a medical practitioner, and/or the individual) can be carried out by way of electronic or signal transmission (e.g., by computer such as via e-mail or the internet, by providing the results on a website or computer network server which can optionally be a secure database, by phone or fax, or by any other wired or wireless transmission methods known in the art).

In certain embodiments, the system is controlled by the individual and/or their medical practitioner in that the individual and/or their medical practitioner requests the test, receives the test results back, and (optionally) acts on the test results to treat the individual.

The various methods described herein, such as determining a subject's risk of having cancer by analyzing the methylation levels of certain genomic DNA loci, can be carried out by automated methods such as by using a computer (or other apparatus/devices such as biomedical devices, laboratory instrumentation, or other apparatus/devices having a computer processor) programmed to carry out any of the methods described herein. For example, computer software (which can be interchangeably referred to herein as a computer program) can analyze the methylation levels of certain genomic DNA loci to determine if a patient has a particular type of cancer, e.g., AML. Accordingly, certain embodiments of the disclosed subject matter provide a computer (or other apparatus/device) programmed to carry out any of the methods described herein.

Kits

In certain embodiments, the presently disclosed subject matter includes kits for the practice of the methods of disclosed subject matter. The kits can include one or more containers containing compositions to practice various methods of this subject matter. The kit can optionally include a container comprising one or more of linkers and/or primers (as described above), and related reagents and buffers. For example, and not by way of limitation, the primers and/or linkers can include the JHpaII 24XXXX and/or the JHpaII 12XXXX primers. The kit can optionally include a container including a methylation-insensitive restriction enzyme, e.g., MspI, and/or a methylation-sensitive restriction enzyme, e.g., HpaII. The kit can optionally include enzymes and related buffers and other reagents for performing the ligation of linkers, and/or amplification of the genomic DNA fragments, e.g., PCR (i.e., for example, DNA polymerase, Taq polymerase, primers, linkers and/or restriction enzymes).

In certain embodiments, the kits can also optionally include appropriate packaging (e.g., opaque containers) or stabilizers (e.g., antioxidants) to prevent degradation of the reagents by light or other adverse conditions.

In certain embodiments, the kits can optionally include instructional materials containing directions or instructions (i.e., protocols) providing for the use of the reagents in performing the disclosed methods. While the instructional materials typically include written or printed materials they are not limited to such. Any medium capable of storing such instructions and communicating them to an end user is contemplated by this subject matter. Such media include, but are not limited to electronic storage media (e.g., magnetic discs, tapes, cartridges, chips), optical media (e.g., CD ROM), and the like. Such media can include addresses to internet sites that provide such instructional materials.

The following Examples are offered to more fully illustrate the disclosure, but are not to be construed as limiting the scope thereof.

Example 1: Validation of DNA Methylation to Predict Outcome in Acute Myeloid Leukemia Using xMELP Introduction A novel assay that simultaneously assesses the DNA methylation status of eighteen prognostically important loci in patients with AML was previously described (15). This methodology of the novel assay was based on the HpaII small fragment Enrichment by Ligation mediated PCR (HELP) assay and depends on molecular techniques-restriction digestion, oligonucleotide ligation and PCR—that are commonplace in a clinical molecular laboratory (16). Unlike HELP, which employs custom-made solid phase oligonucleotide arrays for locus identity and methylation assessment, the novel assay (termed Microsphere HELP or MELP) uses oligonucleotides-coupled fluorescent microspheres and flow cytometric analysis for multiple loci DNA methylation assessment. Similar microsphere-based techniques are commonly performed for multiple-locus mutation assessment of patients with AML in clinical molecular laboratories (17). MELP is a quantitative method for locus-specific assessment of DNA methylation and that methylation levels determined by MELP are virtually identical to those determined by HELP (15). Additionally, a MELP-based DNA methylation classifier using the same prognostic loci previously identified with the HELP assay was able to segregate tumors into subgroups with significantly distinct outcomes. These data suggested that MELP is a robust method of multi-locus DNA methylation quantitation that may be useful for assessing prognosis in patients with AML.

Novel developments have been achieved in both the assay methodology as well as the multivariate classification algorithm used to predict AML prognosis. Specifically, the presently disclosed optimized MELP technique ("xMELP"), shortens the assay time to make it more appropriate for use in the clinical laboratory (18). Additionally, the methylation-based prognostic algorithm is now based on a random forest classifier using a refined 17-locus panel trained from a set of 344 AML samples. With these new alterations, quality control standards were defined for the assay and its performance characteristics were described. Further, the xMELP assay and new classification algorithm strongly predicted overall survival in an independent cohort of 70 primary AML samples. These results indicate that xMELP is suitable for prognostic tumor evaluation in the clinical setting.

Methods and Materials xMELP Assay

The xMELP assay was performed as follows. DNA preparation from 5 million cells was performed with the Qiagen Puregene kit (Qiagen, Valencia, Calif.), following the manufacturer's protocol for DNA extraction from buffy coat samples. The digest and ligation reactions are combined into a single reaction using 500 ng of DNA along with 7.5 µl of previously annealed oligonucleotides (30 D/ml JHpaII 12XXXX and 60 D/µl JHpa24XXXX), 0.5 µl BSA (10 mg/ml, NEB), 0.5 µl ATP (100 mM, pH 7.0, NEB), 5 µl digestions buffer (NEB), 4U MspI or 2U HpaII (NEB) and 2U T4 DNA ligase (Life Technologies). Total reaction volume is 50 µl. Reactions are carried out at 25° C. for 12 hours. Subsequent PCR amplification using JHpaII 24 XXXX primers was performed as described. For most reactions, PCR was performed in 100 mL total volume for 20 cycles. For reactions in which input DNA was serially diluted, PCR with 11 cycles of amplification was performed.

The primers used for xMELP were as follows (nomenclature as previously used with XXXX indicating xMELP primers):

```
                                        (SEQ ID NO: 3)
JHpaII 12XXXX: CGCCTGTTCATG (SEQ ID NO: 4)
JHpaII 24XXXX: CGACGTCGACTATCCATGAACAGG
```

Nucleotides in bold indicate changes in the original MELP primers to prevent redigestion of ligated products. Underlined nucleotides are involved in annealing to genomic DNA. JHpaII24

XXXX was also used for PCR.

For dilution experiments, genomic DNA was diluted with either water to the indicated final amounts or with genomic DNA prepared from peripheral blood of a healthy donor at indicated ratios. Ficoll preparation of bone marrow samples was performed according to standard protocol.

Median fluorescence intensity (MFI) was measured to derive raw abundance values from Luminex beads as previously described (15). $Log_2$(HpaII/MspI) values were scaled by subtracting the mean $log_2$ ratio scores for three loci (MSPI0406S00318682, MSP10406S00890278, MSPI0-406S00653944) that were previously shown to represent an unmethylated baseline within this sample type.

Quantigene 2.0 Hybridization was performed as previously described (15). In particular, sequential hybridization reactions for complexing amplicons onto fluorescent microspheres and for branched DNA signal amplification were performed with the Quantigene 2.0 assay, following the manufacturer's protocol for RNA hybridization (Affymetrix). Specifically, 8 mL PCRs were incubated at room temperature using 5 mL of 2.5 mol/L NaOH, 5 ml of the locus-specific probe mixture, and 5 mL of lysis mixture (the latter two products provided in the Quantigene 2.0 assay) in 68 mL total volume. The reaction was neutralized by addition of 36 mL of 2 mol/L HEPES buffer. This amplicon/probe mixture was added to a 20 mL reaction mix consisting of 0.2 mL of proteinase K, 15 mL of lysis mixture, 2 mL of blocking reagent, and 1 mL of locus specific fluorescent microspheres (all products provided in the Quantigene 2.0 assay). These hybridizations were incubated with shaking at 55° C. overnight. Reactions were placed on a magnet and washed three times with wash buffer (provided in the Quantigene 2.0 assay). The reactions were then sequentially hybridized to pre-amplifier, amplifier, and biotinylated label-probe DNA in 100 mL of the appropriate buffer (provided in the Quantigene 2.0 assay). All hybridizations were performed for 1 hour at 50° C. with shaking. Each hybridization was preceded by magnetic bead capture and three washes. After hybridizations, the reaction was incubated at room temperature with 4 mg/mL streptavidin-phycoerythrin in the appropriate buffer (supplied by the manufacturer). After three washes, the fluorescent microspheres were analyzed by flow cytometry on a FLEXMAP three-dimensional instrument running xPONENT 4.0 software (Luminex Corporation, Austin, Tex.). The entire procedure was performed separately for products derived from MspI-digested, HpaII-digested, or mock-digested DNA. Amount of bound product was determined by phosphatidylethanolamine signal, whereas locus identity was determined by fluorescence signal of each microsphere. Relative methylation was determined by the ratio of phosphatidylethanolamine median fluorescence intensity of each locus in MspI-digested and HpaII-digested samples normalized to the same ratio of known hypomethylated loci.

Tumor Bank

Training data were obtained from a previously published cohort (GEO accession GSE 18700, http://www.ncbi.nlm-.nih.gov/geo/query/acc.cgi?acc=GSE 18700) of 344 AML patients collected by the Dutch-Belgian Hemato-Oncology Cooperative Group (HOVON) for which methylation status had been measured using HELP (6). As previously described (15), a subset of these samples were rerun using MELP and converted the HELP values to MELP-scale values using Deming regression. This 344-sample cohort served as the training set for creating the random forest classifier in this Example.

An independent cohort of 207 AML samples was obtained from patients evaluated at the Perelman School of Medicine, University of Pennsylvania (Philadelphia, Pa.). All subjects provided informed consent for collection under a protocol previously approved the University of Pennsylvania Institutional Review Board. Genomic DNA was isolated, and xMELP was performed on all 207 samples. A subset of this group (n=70) was randomly selected from the set of subjects for whom survival data were available, and this subset was used to validate the outcomes performance.

Locus Selection

Using the original HOVON methylation data, 18 loci have previously been identified as predicting outcome in AML (6), and their use with MELP has been previously described (15). Additionally, the original HOVON data set was randomly repartitioned and supervised principal components were used as previously described to identify an additional 9 candidate loci. Methylation at these 27 loci was simultaneously assayed along with three control loci in a single multiplex experiment for each AML sample (Table 1 and Table 2). A subset of these loci was used in the final classification model (see below under Data analysis and multiplex classification).

Data Analysis and Multiplex Classification

Data analysis was performed using the R statistical software package (R version 3.0.2) in conjunction with the survival (version 2.37-7), MethComp (version 1.22), and scatterplot3d (version 0.3-35) packages (19-22). In order to provide detailed documentation of the analysis procedures, an R script capable of reproducing figures from this manuscript has been included as supplementary data along with associated data files. Random survival forest calculations were performed using the RandomForestSRC package (version 1.4) (23) with 1000 trees. The random forest was trained to predict survival using the HOVON (n=344) HELP data after converting the HELP values to equivalent MELP scale values using Deming regression as previously described (15).

In order to remove uninformative loci from the model, a procedure recently described proposed by Hapfelmeier and Ulm was used (21). This approach utilizes variable importance scores, which reflect the calculated influence of each locus on overall random forest performance. Five random forests were generated using the training data set, and the distribution of the variable importance score was tabulated for each of the 27 candidate loci. For each locus, a control distribution was then generated by randomly permuting the values of that locus across samples while retaining the original values at all other (n=26) loci. After training a random forest on this permuted data set, the variable importance for the selected locus was recorded. This procedure was repeated 50 times for each locus, resulting in a distribution of control importance scores. This distribution represents the expected importance of each locus if it were uninformative, and the control distribution can then be compared to the distribution of importance scores obtained when using the original (nonpermuted) data. To determine which loci contribute significantly to the random forest performance, a 1-tailed T test (actual distribution>control distribution) was used at each locus, with a locus considered "informative" if it showed a Benjamini-Hochberg-corrected P value<0.05.

17 loci passed this threshold and were utilized for the remainder of the work. After identification of the optimal subset of 17 informative loci (Table 1 and Table 2), a final random survival forest was trained. The output of this random forest, which is designated as the methylation score (M-Score), represents the estimated risk associated with a given sample. Thus, a low M-score corresponds to a long predicted survival (good prognosis), and a high M-score corresponds to a shorter predicted survival (poor prognosis).

Perturbation Analysis of Multiplex Classification Score

In order to determine the effect of changing the value of one or more loci on the overall score function, Monte Carlo perturbation approach was utilized. Briefly, random subsets of 1, 2, 3, 5, or 10 loci were selected in order to assess the effect of different numbers of "failed" loci. Random specimens were selected from the 21 repeat samples, and for each random subset of perturbed loci the values of each locus were replaced with a value for the same locus drawn randomly from the full cohort of 208 UPenn samples. In this way, a draw of random values were generated that were biologically plausible but incorrect. This process was repeated 100 times for each number of perturbed loci, and summary results were obtained.

Results

It has been previously shown that the MELP assay can simultaneously assess levels of DNA methylation at multiple loci (15). Briefly, this assay uses a methylation insensitive restriction enzyme (MspI) along with its methylation-sensitive isoschizomer (HpaII) to create two differentially digested DNA aliquots. Ligation of an oligonucleotide linker followed by linker-specific Taq-mediated PCR generates pools of amplicons in which relatively short, easily amplifiable products predominate. Thus, in the HpaII digest, regions of hypomethylated digestable DNA will be selectively amplified and will be relatively over-represented compared to regions of hypermethylation. Amplicons are fluorescently labeled and hybridized to Luminex microspheres, which are then subjected to flow cytometry to quantitate amplicon abundance (determined by amplicon fluorescent signal) at specific loci (determined by Luminex microsphere fluorescence). Differential signals from the MspI and HpaII digests at each locus are used to identify the level of methylation in the original sample DNA. A methylation level is calculated as $\log_2(\text{HpaI/MspII})$, with normalization provided by the average methylation level of three control genomic DNA loci known to be hypomethyated across virtually all AML samples. Notably, this procedure is amenable to multiplexing, and >30 loci were successfully quantitated simultaneously in a single Luminex experiment utilizing on two reaction tubes. Despite the utility of the MELP assay in its original form, experiments indicated that a number of improvements could improve its suitability for implementation in the clinical laboratory.

Development of xMELP

Figure 1B:
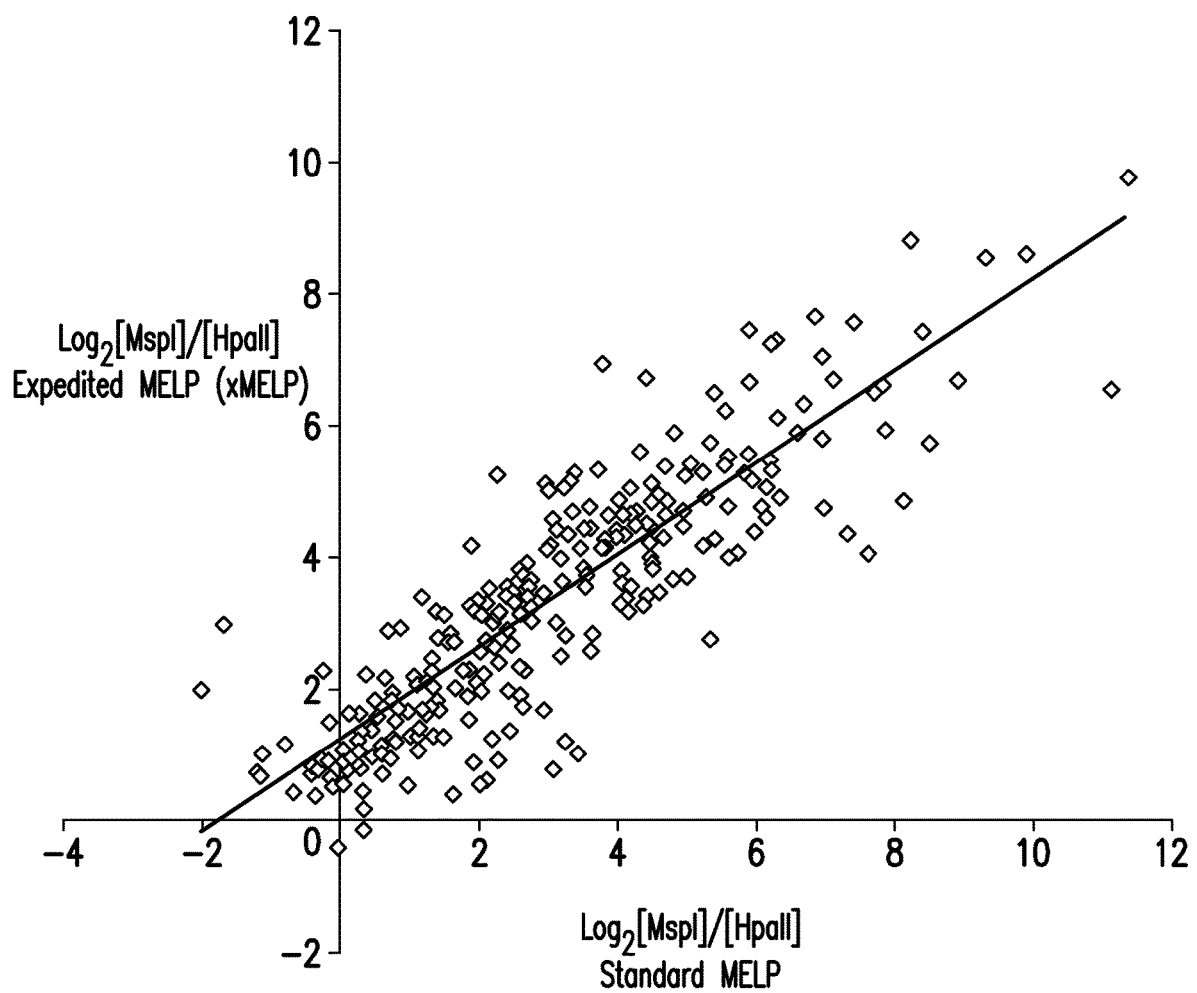

In order to improve the turnaround time for clinical methylation assessment, the original MELP technique was simplified using a single base-pair substitution in the oligonucleotides used for linker ligation. In both the HELP and original MELP assays, ligating the oligonucleotides to genomic DNA fragments recreates a HpaI/MspII site (15, 16). Since MspI is not heat labile, the standard HELP assay requires a phenol chloroform extraction followed by EtOH precipitation after the restriction digest to prevent re-digestion of ligated products. By changing a single base pair in the primers used for ligation (see Materials and Methods), the 5' overhang necessary for genomic DNA annealing was maintained while ensuring that the ligated products no longer contain a HpaI/MspII restriction site. With this subtle alteration, the restriction digestion and ligation of MELP can be combined into a single step, thereby reducing the total time required for performing MELP by a full day and significantly decreasing the amount of sample manipulation (FIG. 1A). It is important to note, that this alteration of the MELP technique (referred to now as expedited MELP or xMELP) does not alter the assessment of methylation status. As shown as in FIG. 1B, there is a nearly uniform correlation between MELP and xMELP at every locus analyzed in ten primary AML samples. Thus, xMELP is a valid surrogate of standard MELP and is the technique used in all subsequent analyses.

Quality Control and Reproducibility for xMELP

Figure 2A:
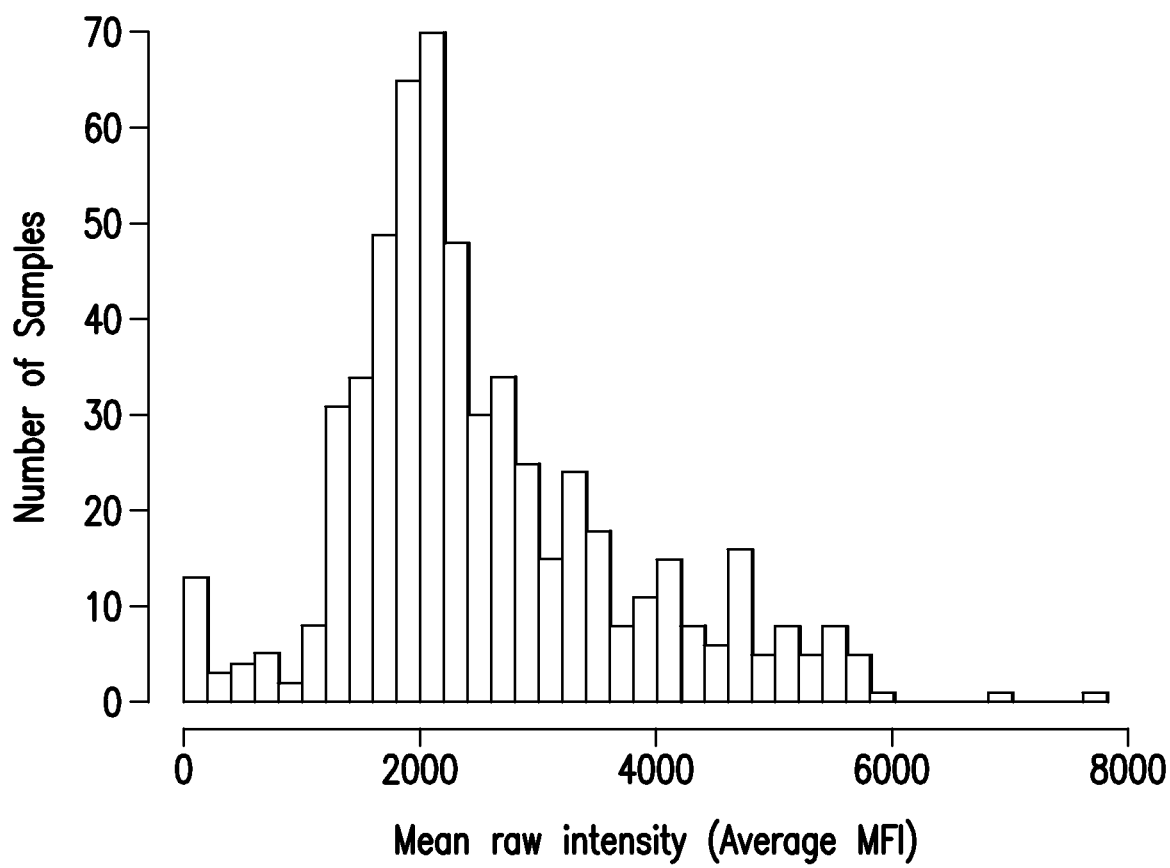
FIG. 2A-C. Quality control of xMELP assay. xMELP was performed on 207 primary AML samples (UPenn cohort). A) After microsphere flow cytometry, mean MFI (median fluorescence intensity) across 31 loci was determined. Distribution of mean MFI is shown. The relatively large number of samples with low MFI indicates assay failure for these samples. B) Comparison of MFI from three control loci and mean MFI for each sample is shown. MFI of the three control loci is plotted. Colors indicate mean MFI (black: $\leq 50$; medium gray: $>50$: $\leq 200$; light gray: $>200$, $\leq 400$; dark gray$>400$, $\leq 800$; open circle: $>800$). C) Enlargement of the group of samples with low MFI of control loci. The dotted box indicates those samples for which the assay likely failed, corresponding to an MFI signal<100 for each of the control loci.
Figure 2B:
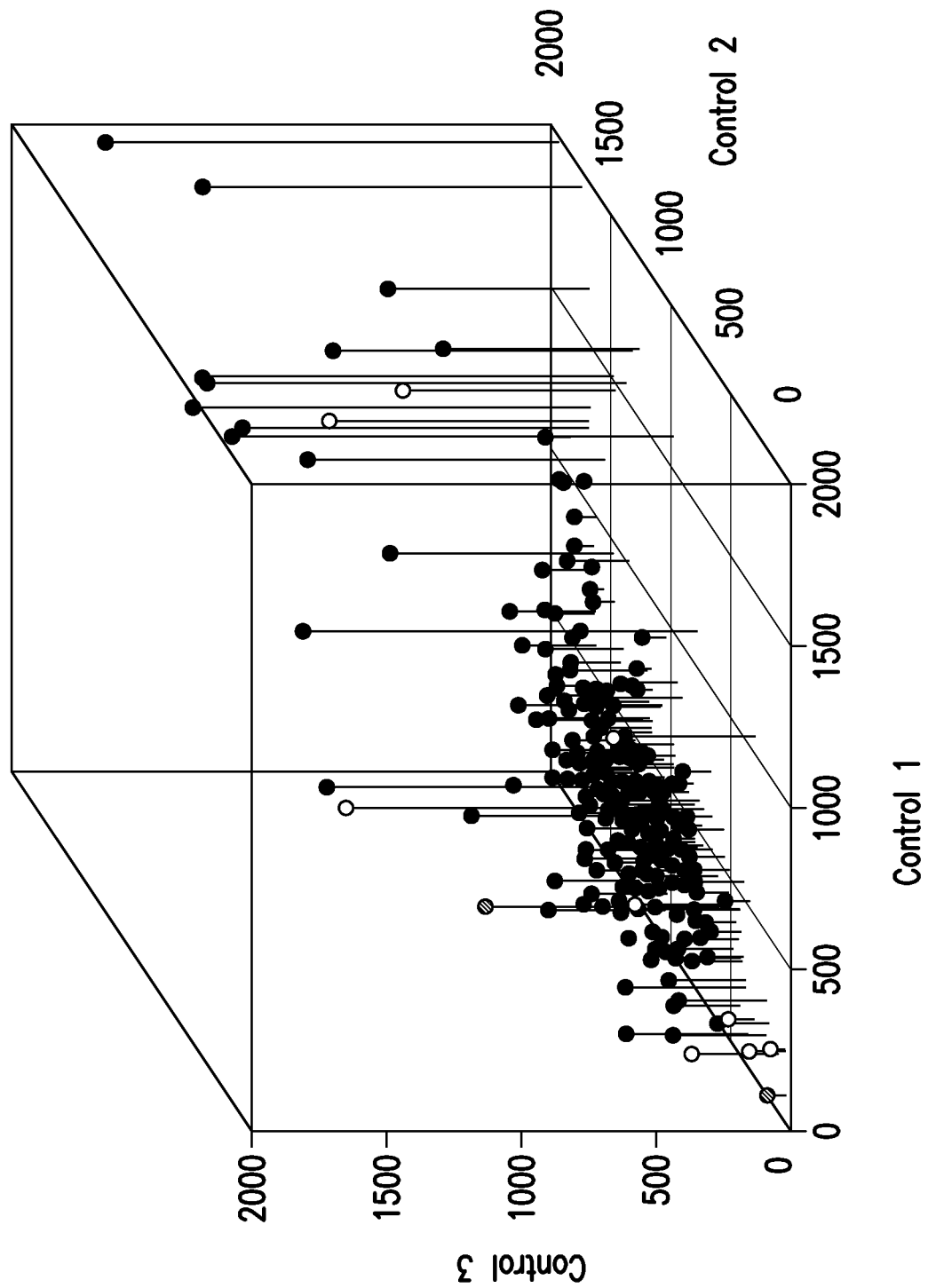
Figure 2C:
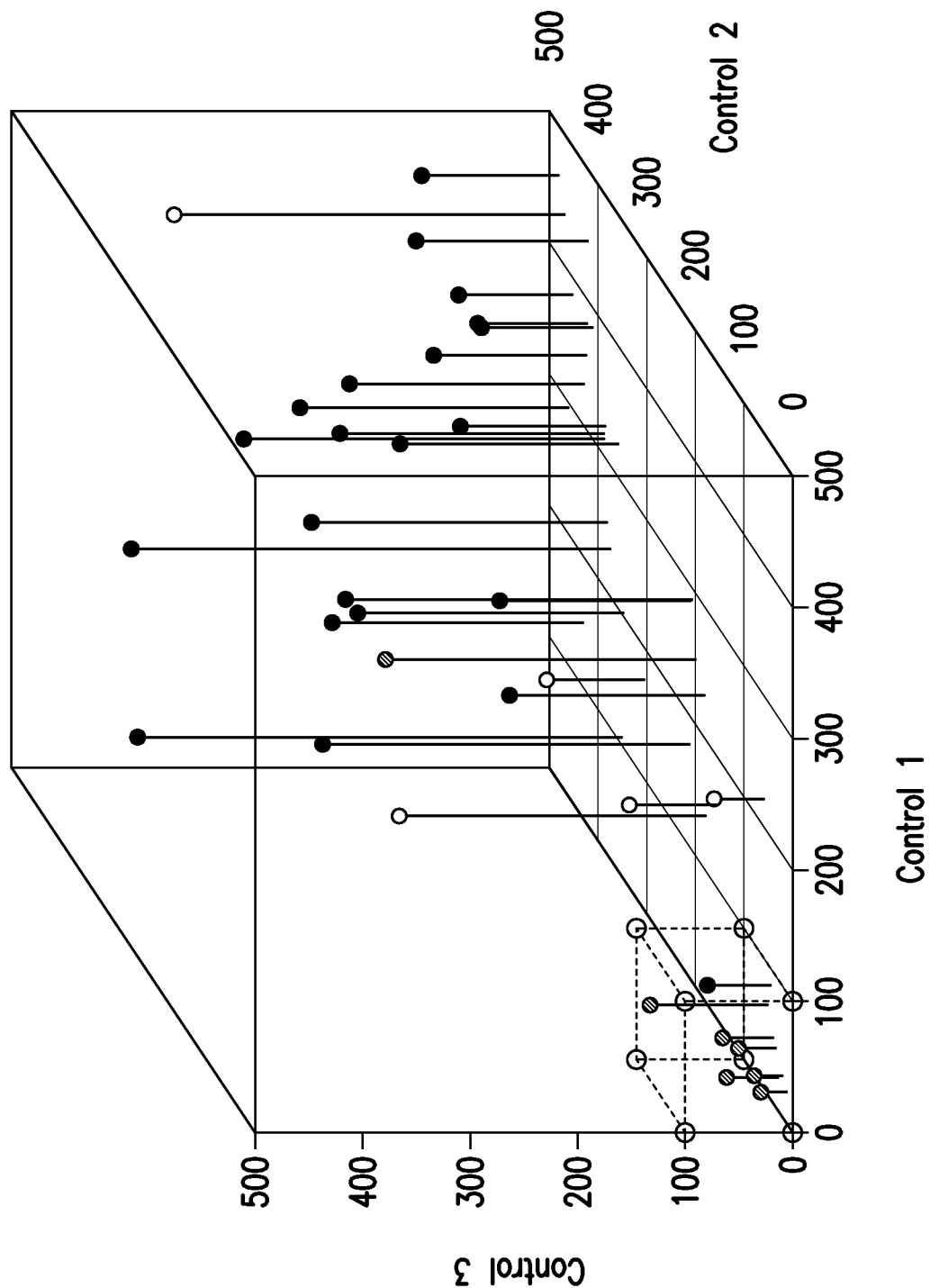

In the context of running both MELP and xMELP, it was noted that occasional samples showed uniform low fluorescence signals across all loci, suggestive of either inadequate DNA quality (low MspI and HpaII signals) or failure of any of the subsequent reactions (low MspI or HpaII signals). To address the need for a uniform quality control metric, the mean individual scores (HpaII or MspI) were determined across all loci as a surrogate for global assay performance (FIG. 2A). The individual HpaII or MspI values obtained at the three unmethylated control loci used to normalize the results were then examined. The low tail of the mean score distribution was associated with control locus values<100 (FIG. 2B, C). As a result, a quality control cutoff of 3/3 control loci<100 (median intensity for Luminex analysis) was established. This cutoff was used in subsequent analyses.

Figure 3:
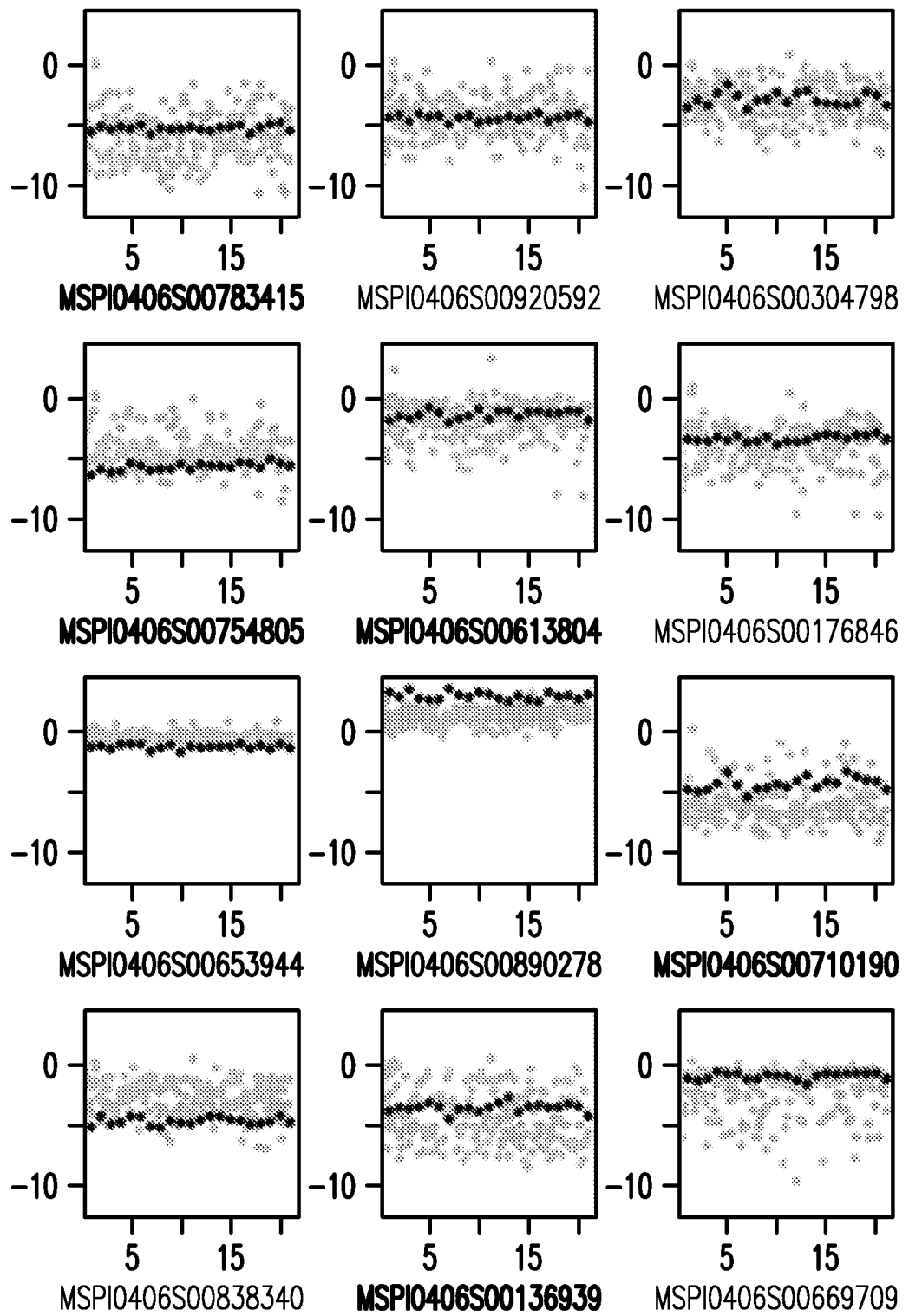
FIG. 3. Variability of xMELP-determined methylation levels. xMELP was performed on the entire primary AML UPenn cohort (n=207) and on 21 aliquots of a single sample. Methylation levels, measured by $\log_2([\text{HpaII}]/[\text{MspI}])$, for each locus were determined and are shown. Black dots indicate 21 replicates of a single sample, while gray dots represent the ratios for all samples in the UPenn cohort in order to illustrate the range of biological variability. Loci included in the final xMELP classifier are in black, loci not in the classifier are in light gray, normalization loci are in gray.
Figure 3:
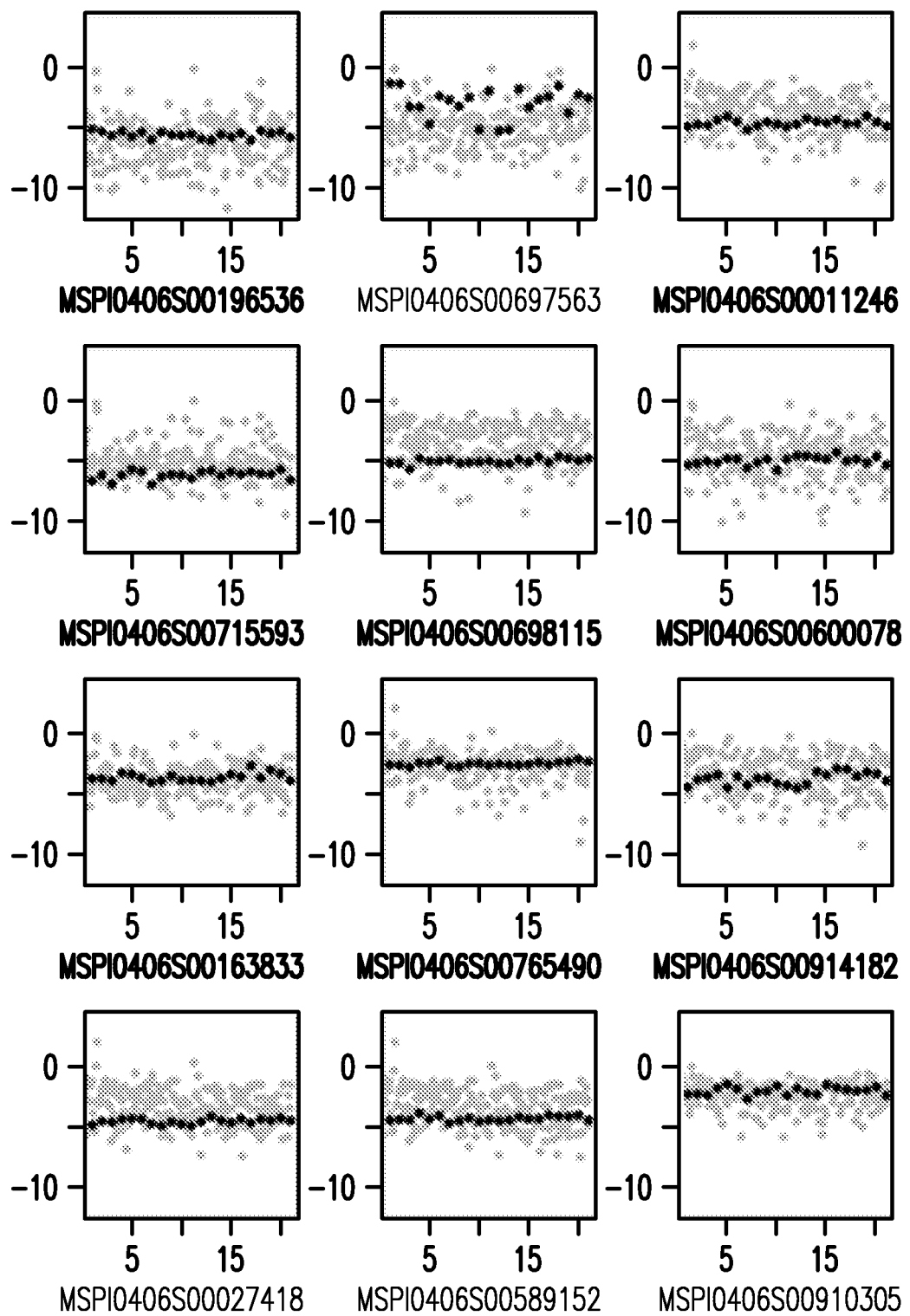
Figure 3:
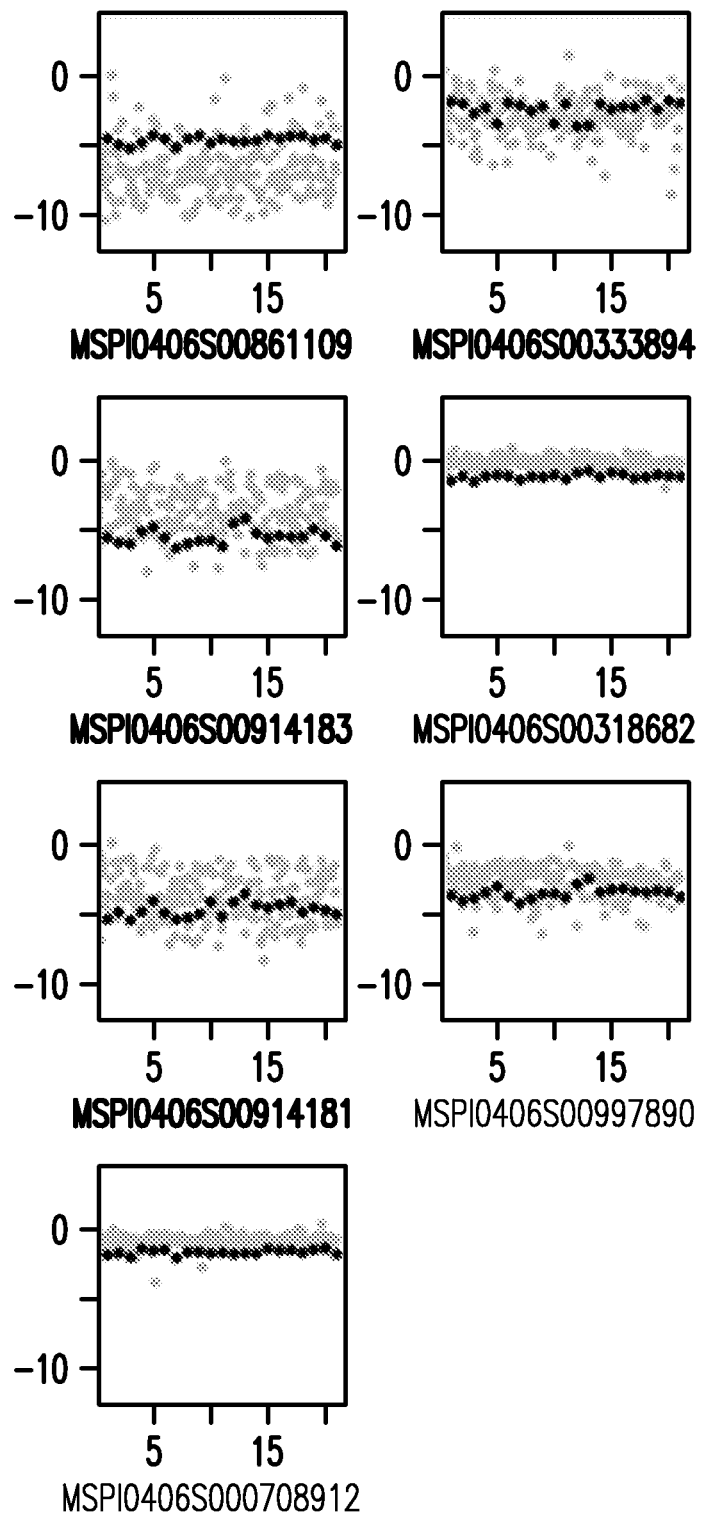

To assess the precision of individual locus measurements with xMELP, 21 replicate frozen cellular aliquots of a diagnostic bone marrow sample were obtained from a single AML patient. DNA was prepared from each aliquot and was subjected the xMELP assay. Loci were selected as a combination of the original group shown to be prognostic for AML (n=18) along with an additional 9 loci that were identified as potential additional prognostic loci (see Materials and Methods). In order to assess both intra and inter-assay reproducibility, groups were run on three separate days (7 independent replicates/day). Results are shown in FIG. 3. Because it is not appropriate to calculate a % CV in the case of $\log_2$-based scores extending below zero, the reproducibility in the control samples were compared with the range of methylation scores measured for these same loci in a cohort of 207 frozen AML specimens collected at the University of Pennsylvania. As shown in FIG. 3, with the exception of one locus (MSP10406S00697563), fluctuations in the (intra- and inter-assay) replicate samples are small (median intra-assay SD=0.29, median inter-assay SD=0.12) and are significantly less that the biological variation seen across all samples (median range=9.4).

Expansion of Candidate Loci for AML Prognosis

Having established QC criteria and reproducibility parameters for individual loci using xMELP, an improved classifier for AML prognosis was next developed. Similar to previous work (15), MELP-correlated HELP values from the HOVON AML data set were used to train this classifier. In the current analysis, however, the entire HOVON data set was used rather a subset for training. Further, in contrast to the previously reported classifiers utilizing supervised principal components analysis, a random forest classifier was utilized in order to exploit the robust properties of ensemble machine learning methods (24). Robust classification results using a random forest classifier were recently obtained to segregate myeloid neoplasms from reactive conditions (25), and a similar approach was utilized for AML survival prediction.

Figure 4A:
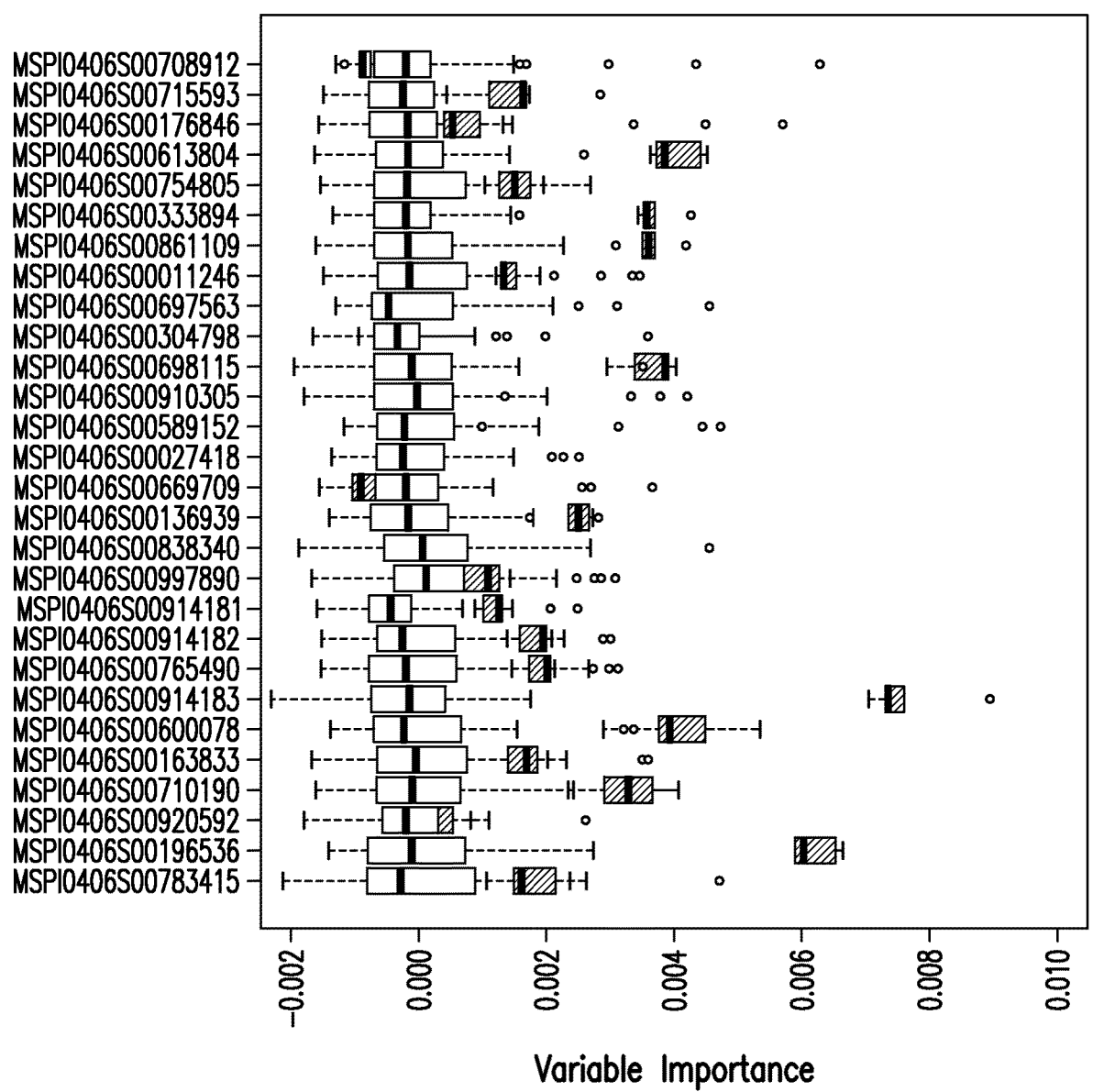
FIG. 4A-C. Variable selection and random survival forest. A) A comparison of variable importance (x axis) is shown for 31 loci. Distribution of importance scores from independently trained random forests on the original data are shown in gray; control distributions derived from perturbation analysis are shown in white. Loci with original>permuted scores (P<0.05) were retained for the final model. B) 17 retained loci from (A). C) Error rate (left) and final variable importance (right) for 17 loci in the final 1000-tree random survival forest classifier.
Figure 4B:
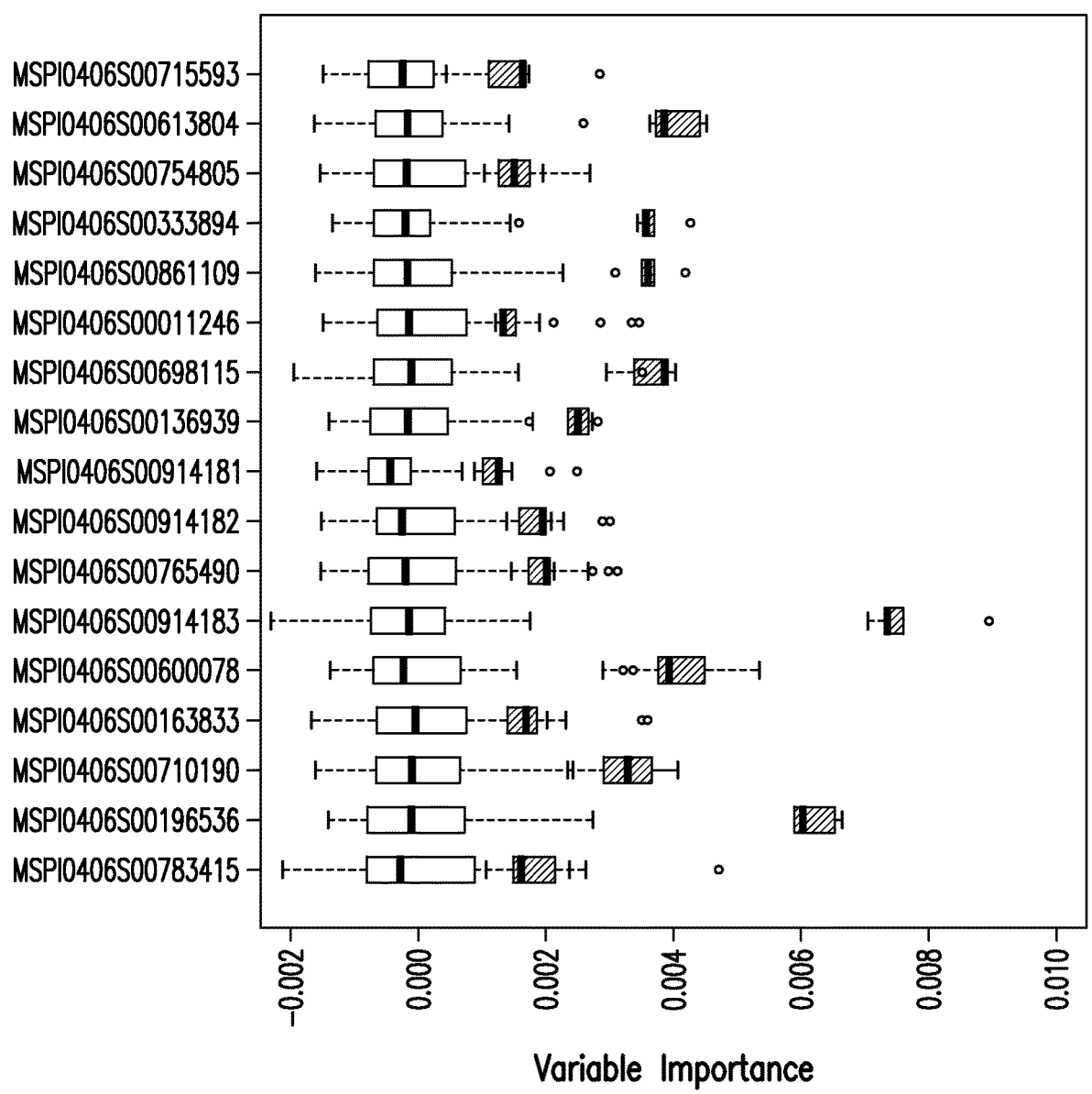
Figure 4C:
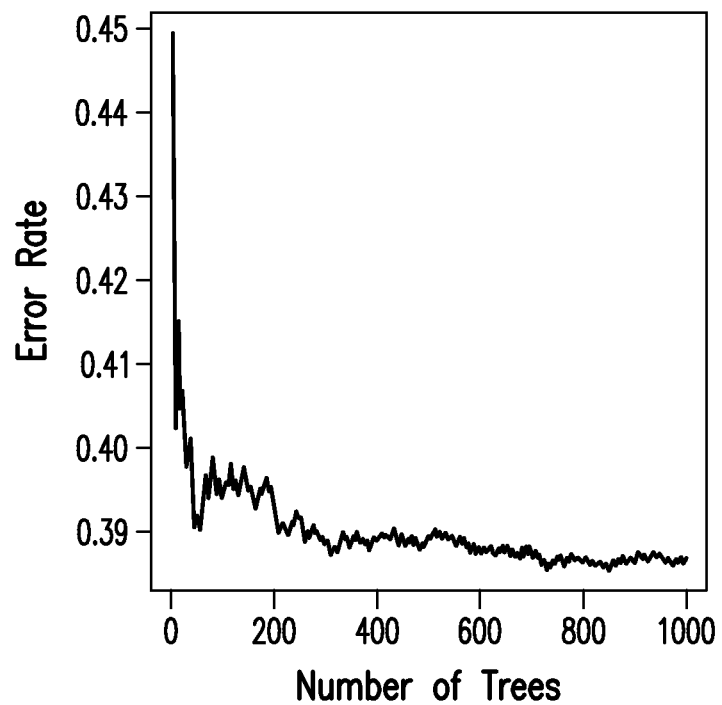
Figure 4C:
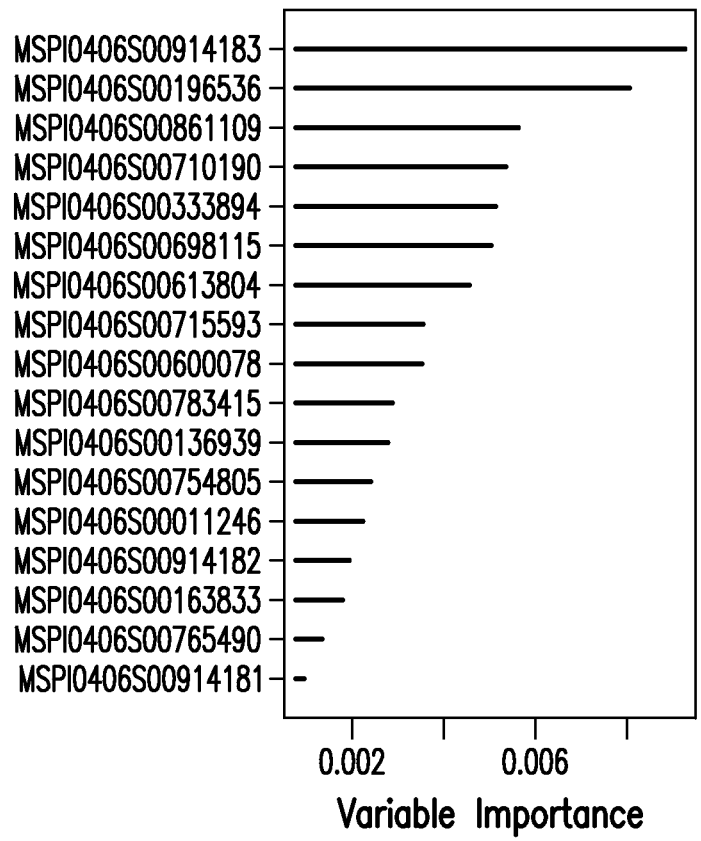

To assess which of the 27 potential loci should be included in the final model, a recently proposed technique (26) was utilized to select an informative subset. For each locus the distribution (n=5) of the variable importance score in the random forest mode was compared with a control distribution (n=50) derived from generating random forests using permuted data for the given locus. Results for each of the 27 loci are shown in FIG. 4A, and 17 loci were identified that have a true importance significantly greater than control importance (corrected P value of <0.05, FIG. 4B). The final random forest classifier was constructed using these 17 loci. Importantly, the locus previously shown to have poor precision characteristics (MSP10406S00697563, FIG. 3) is not included in this model.

Figure 5A:
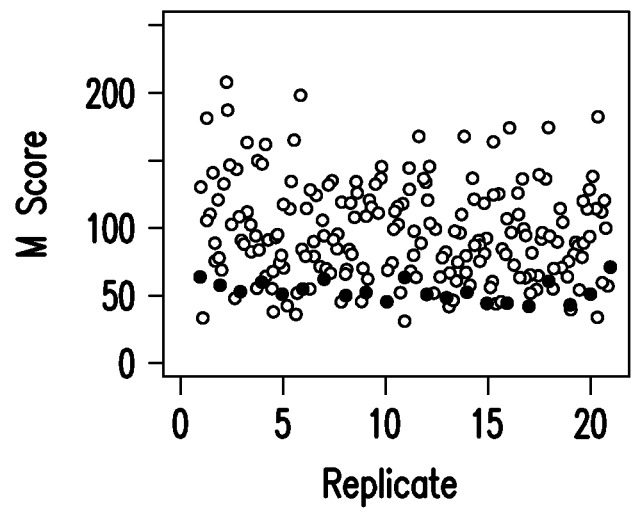
FIG. 5A-E. Variability of the overall methylation score (M-score). A) M-scores for the entire primary AML UPenn cohort (gray dots) and for 21 replicates of a single primary AML sample (black dots) are shown. Variability of M-score in the replicates is minimal compared to variability of M-scores across the entire UPenn cohort. B) M-scores of six duplicate samples. Line of unity is shown. C) Effect of Ficoll centrifugation and freezing on M-scores. DNA from five primary AML bone marrow aspirates was isolated prior to Ficoll centrifugation (fresh no Ficoll), after Ficoll centrifugation (fresh), and after both Ficoll centrifugation and cryopreservation in DMSO containing media (frozen). Comparison of M-scores for these samples is shown along with the line of unity. A single fresh sample failed quality control (FIG. 2), so only four samples are shown for plots that include fresh samples. D) Effect of normal DNA contamination on M-scores. DNA from two primary AML samples was diluted with varying amounts DNA from normal peripheral blood. M-scores for each dilution are indicated (closed and open circles). M-scores of the entire primary AML UPenn cohort (gray dots) are shown as a comparison of the variability across AML samples. E) Robustness analysis of M-score score with random locus perturbation. For reference, the bottom of the figure shows the range of tertiles of M-score seen in 70 patients from the UPenn cohort (see FIG. 6).
Figure 5B:
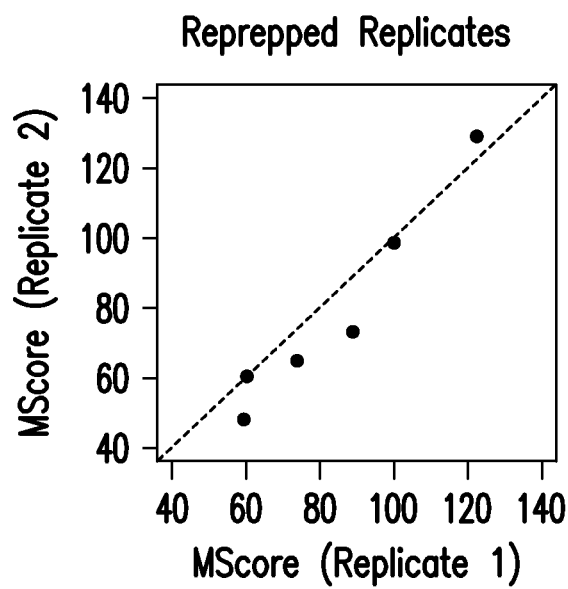

The predictive score generated by the random forest survival classifier is, in essence, a risk score that increases with poorer prognosis (27). To assess the precision of this aggregate prognostic indication, the 21 replicate samples were utilized to generate a risk score using the 17 loci in the final classifier. As shown in FIG. 5A, variation in intra-sample score is small compared to the inter-sample distribution among the 207 UPenn AML samples, (overall precision=14.8% CV; intra-assay precision=13.6% CV; inter-assay precision=7.4% CV). Additionally, six samples were independently processed and analyzed in duplicate, and methylation risk scores for all of the samples were highly reproducible (FIG. 5B).

Figure 5C:
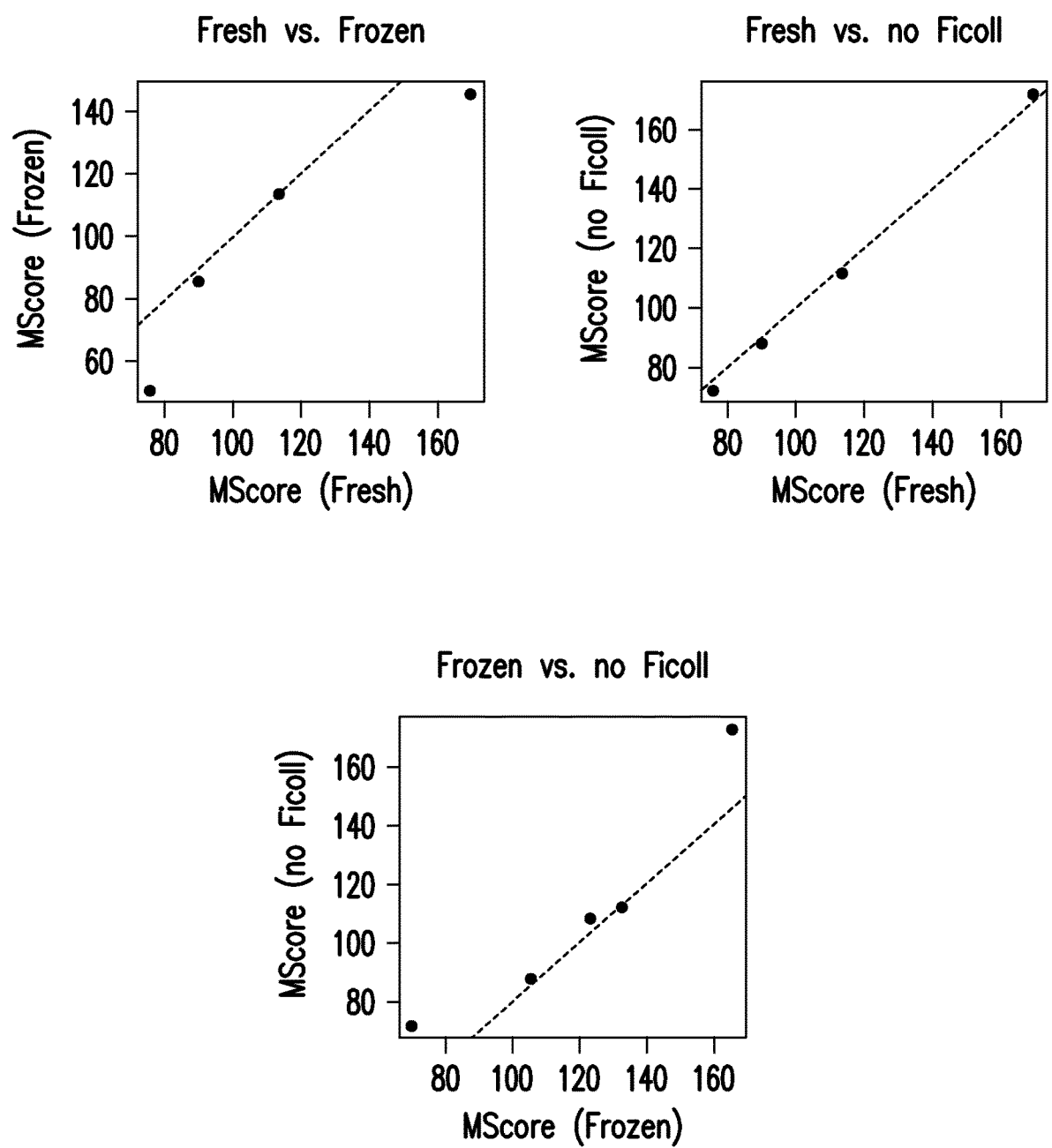

To further determine the effect of preanalytical sample parameters on the methylation risk score for AML, additional characteristics of the assay that are relevant to its use as a clinical test were explored. Since the prognostic results of xMELP are obtained from mononuclear AML blasts that have been enriched by Ficoll gradient centrifugation and are then frozen, and since most clinical specimens are subjected to neither Ficoll enrichment nor freezing prior to processing, the effects that these two procedures would have on xMELP-derived methylation scores were determined. For this analysis, multiple fresh bone marrow samples were obtained from five newly diagnosed AML patients. DNA from these samples was extracted at three points: 1) prior to any manipulation ("fresh no Ficoll"), 2) after Ficoll gradient centrifugation ("fresh"), and 3) after both Ficoll gradient centrifugation and subsequent freezing in standard cryo-preservation media ("frozen"). xMELP analysis was performed and the methylation risk score was obtained using the disclosed random forest classifier. One fresh, Ficoll purified sample was eliminated from consideration due to QC failure. The remaining results are shown in FIG. 5C and demonstrate minimal variation of methylation scores among the three types of cellular manipulations, implying that fresh bone marrow samples that are not Ficoll-gradient enriched for blasts are appropriate for xMELP analysis.

Figure 5D:
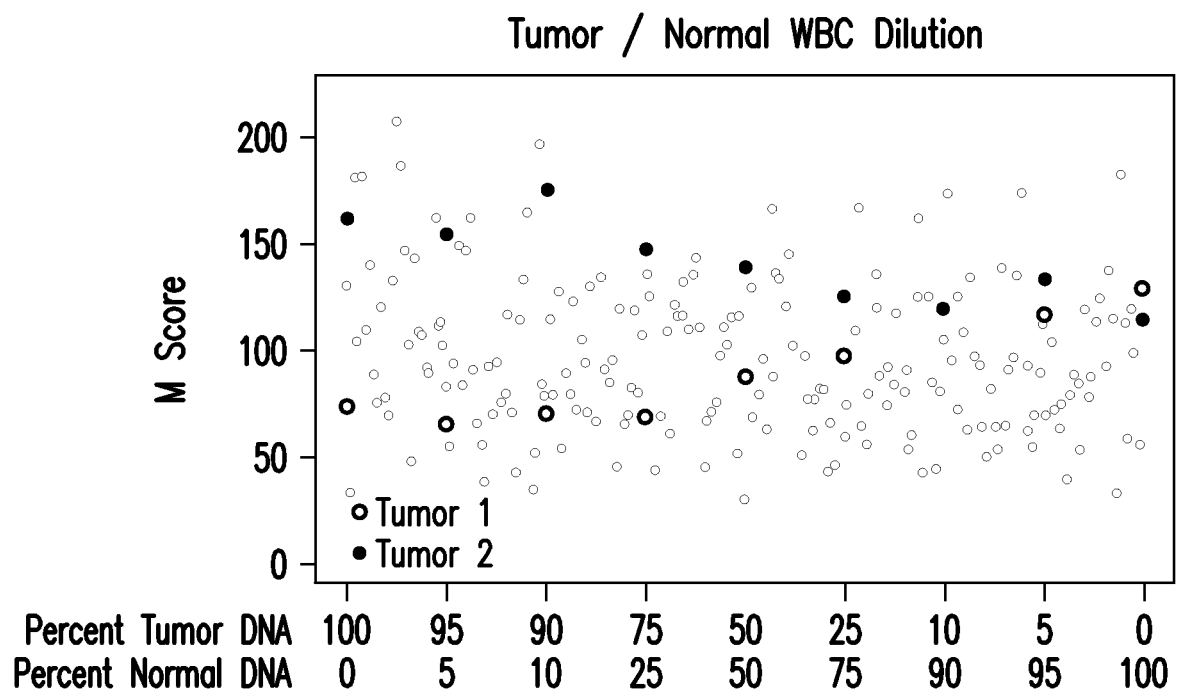

These similar results were somewhat surprising, since it was considered that maturing granulocytes in the unmanipulated sample might significantly alter the methylation score. Therefore, determination of the minimal blast percentage for which xMELP is valid was sought. To this end, varying ratios of genomic DNA from primary AML samples were combined with DNA from normal peripheral blood and performed xMELP on these mixtures. As shown in FIG. 5D, a 75:25 mixture of leukemic:normal DNA retains a similar MELP score to that of the leukemic sample alone, whereas a 50:50 ratio shows a substantial deviation.

Figure 7:
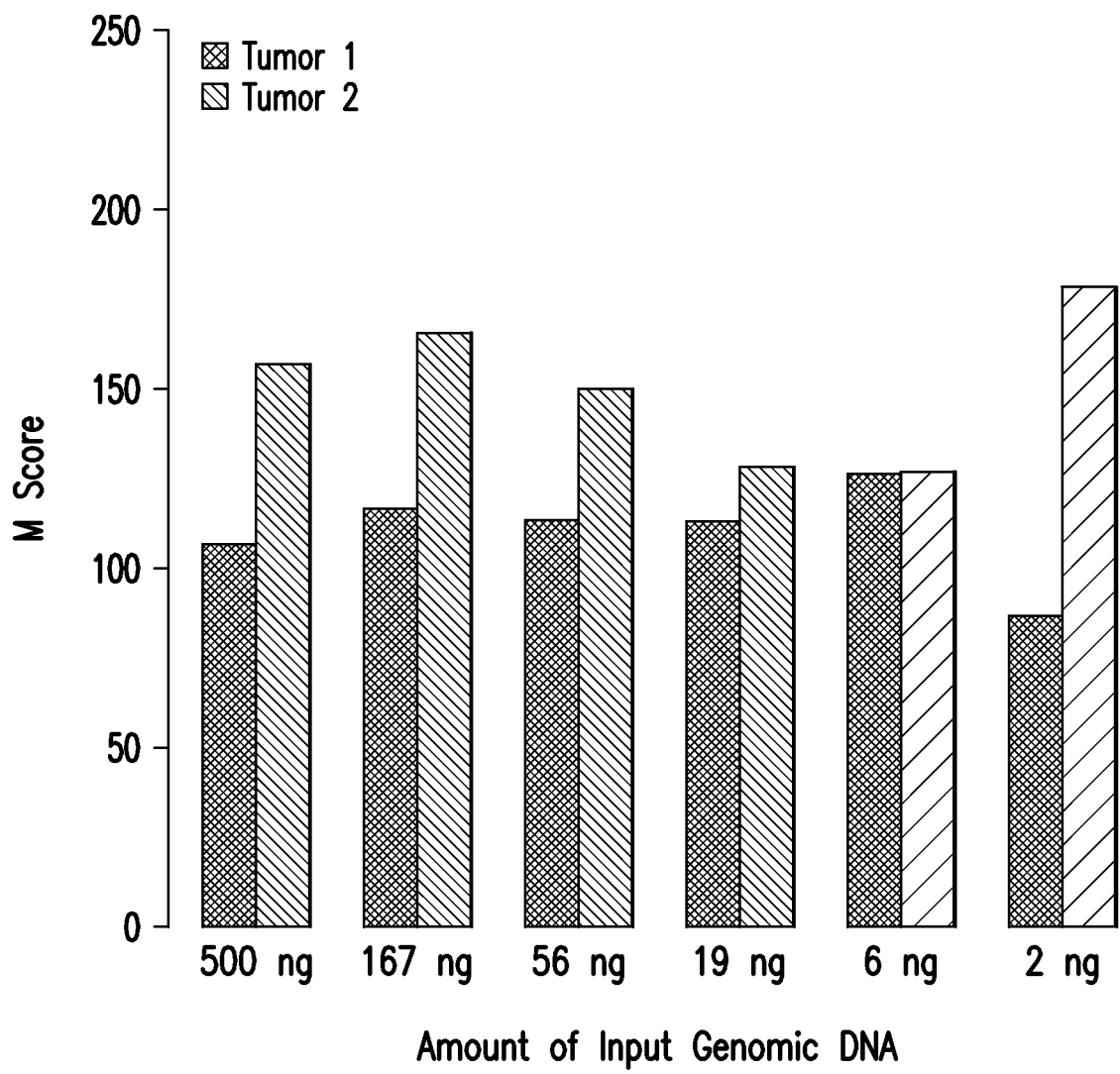
FIG. 7. Effect of input DNA on M-score. Serial dilutions of genomic DNA were subjected to the xMELP assay. M-scores of dilutions are shown. Hatched lines indicate samples that failed quality control.

Since the amount of DNA that can be obtained from a marrow or peripheral blood specimen can be highly variable, the total amount of DNA required for xMELP to yield valid results were also determined. For this analysis, diluted genomic DNA from AML samples were serially and xMELP was performed on the dilutions. Interestingly, all dilutions that pass the quality control criteria established for the assay show similar xMELP scores as the undiluted DNA (FIG. 7). Of note, neither sample passed quality control standards with 2 ng of DNA, so this may be the lower limit of DNA amounts that is useful for xMELP testing.

Figure 5E:
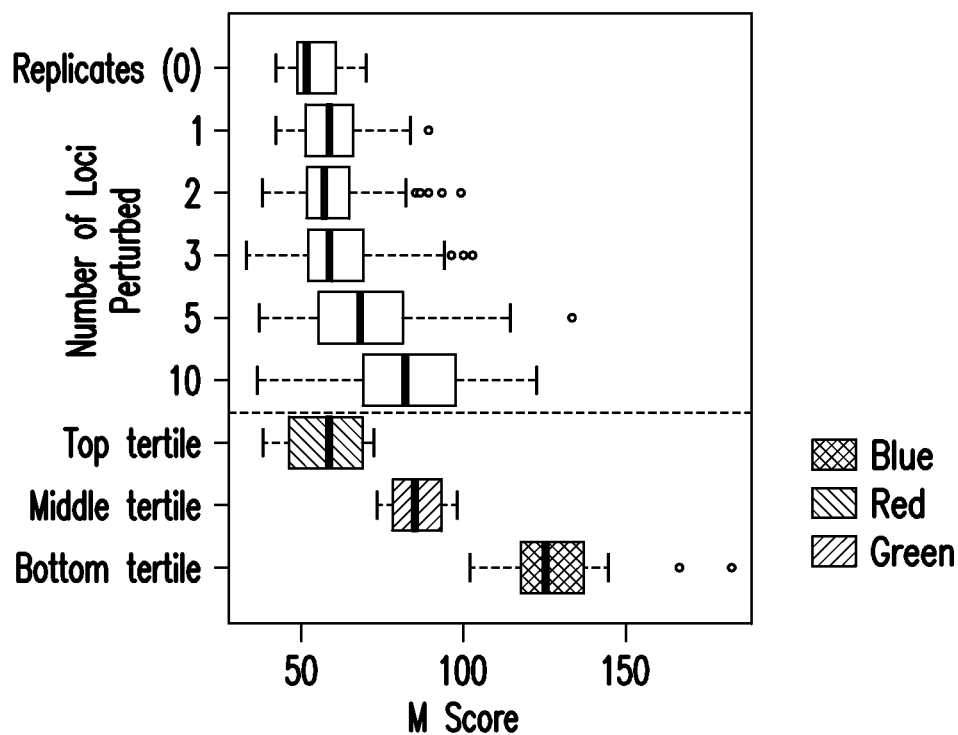

One advantage of predictors based on multiplex measurements is that the aggregate score may be robust even if a subset of individual components is perturbed. To explore the characteristics of the AML classifier, the effect of a simulated "failure" of 1, 2, 3, 5, or 10 components were compared to the inherent score variation observed in the 21 replicates. To assess the effect of values that would be plausible but wrong, a random replicate from the 21 available was selected, selected a random subset of j loci (j=1, 2, 3, 5, 10), and replaced the value at that locus with another value randomly chosen from the cohort of 207 U Penn samples. This process was repeated (n=100) for each value of j, and results were tabulated. Given the fact that the replicate sample has a risk score that is low relative to most samples in the UPenn cohort, this should provide a conservative estimate of the effects of perturbing the assay since it is less likely that multiple perturbations will "offset" each other for the final score. As shown in FIG. 5E, the score distribution shifts higher toward the population mean when the number of perturbed loci (j) is increased. However, the overall score distribution is relatively stable compared with true replicates if only a single locus "fails," suggesting that the multiplex analysis provides some buffer against changes in the methylation risk score due to analytical problems at a single locus.

Validation on an Independent Sample Cohort

Figure 6:
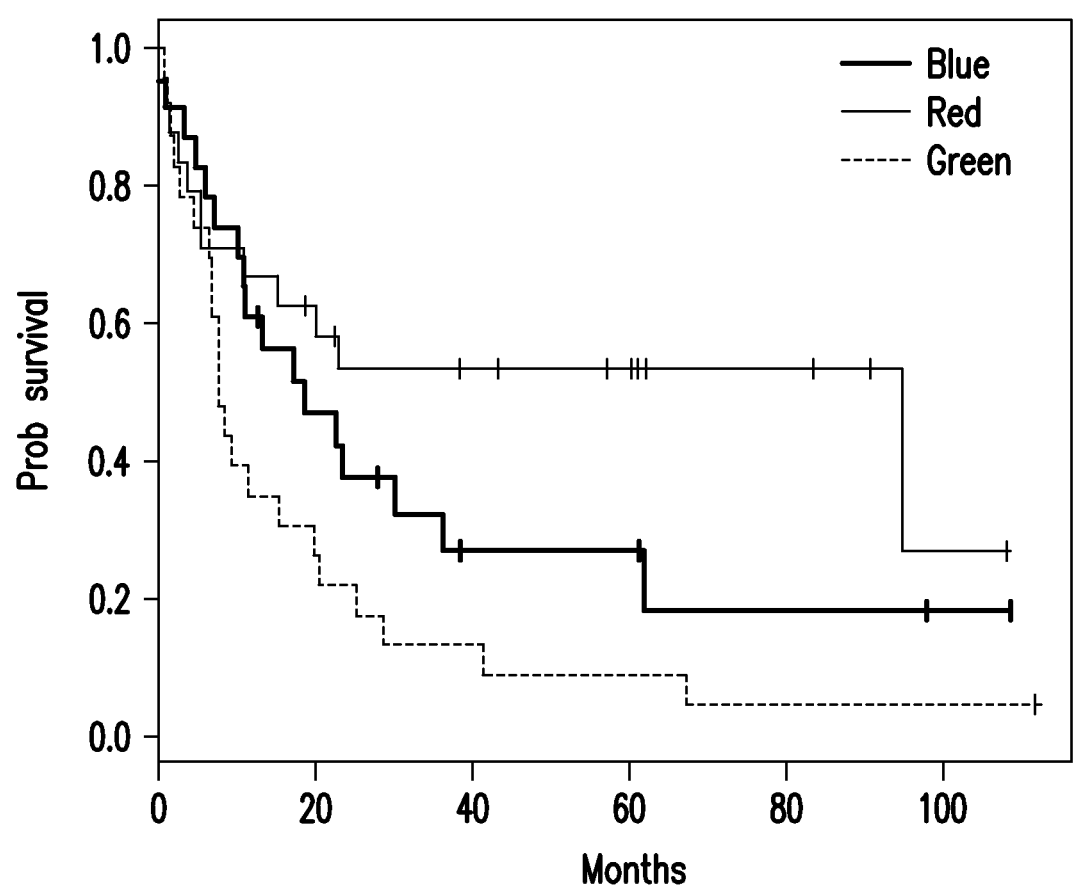
FIG. 6. Outcome analysis based on M-scores. Using the random forest trained on the HOVON data set, M-scores were determined for seventy primary AML samples from the UPenn cohort. Samples were ranked by M-score and divided into tertiles. Overall survival for each tertile is plotted (red, lowest M-score group, n=24; blue, middle M-score group, n=23; green, highest M-score group, n=23; p=0.009, log-rank test).

Having demonstrated that the disclosed assay shows reproducible results and is robust in the presence of defined preanalytical variables, its ability to predict AML survival on a cohort of 70 subjects (subset of the 207 tumors) for which overall survival data was obtained was directly tested. Since the classifier was trained on the HOVON data, this UPenn data set represents an independent cohort from a second institution. xMELP results were used to generate methylation risk scores using the random forest classifier, and sorted results were divided into tertiles. Survival analysis showed a highly significant difference between methylation risk score-based cohorts (FIG. 6, P=0.009), thus demonstrating the clinical validity of this assay. Note that a low methylation risk score correlates with a good prognosis, and a high methylation risk score correlates with poor prognosis. Taken as a whole, these results strongly suggest that the xMELP assay can predict outcomes of patients with AML in two completely independent sets of AML samples (HOVON for training, UPenn for testing) and that MELP may have clinical utility for prognostication of patients with AML.

Discussion

In a previous study, the MELP assay was utilized to assess DNA methylation in select loci and showed that—at the individual locus level—the assay is specific for the loci of interest, linear over a three-log range of signal intensity, as quantitative as methods involving real-time PCR, and capable of faithfully recapitulating levels of DNA methylation determined by the HELP assay and MassArray Epityper Assay (15). In terms of methylation in AML, an overall methylation risk score was demonstrated to significantly predicted outcome in a cohort of primary AML samples. Taken together, these results, coupled with the relatively standard techniques and instrumentation used for MELP, suggested that MELP could be a useful assay for determination of prognostic DNA methylation patterns in AML and perhaps additional diseases.

The previous study has been expanded on by significantly improving the techniques and analysis, clarifying the assay characteristics (including precision), establishing quality control parameters, and demonstrating the predictive potential of xMELP in an independent set of primary AML samples. These results further the argument that MELP can be used for measurement of DNA methylation in a clinical laboratory setting for determination of both prognosis and optimal treatment of patients with AML.

With the development of xMELP, substantial improvements to the assay technique, the loci used and the method of analysis were made. A single base-pair change in the primers used significantly reduces the amount of hands-on work required for the assay and decreases the turnaround time by a full day. The entire MELP assay can now be performed with a turnaround time of two days, well within the optimal temporal window between AML diagnosis and initiation of chemotherapy. The MELP yields virtually identical results regardless of whether leukemic blast enrichment is performed by Ficoll gradient centrifugation; thus, the sample typically received in a clinical lab-unmanipulated bone marrow aspirate is adequate for MELP analysis.

The dilution experiments with normal DNA indicate that a 25% dilution with normal DNA does not significantly alter methylation risk score, so a 75% blast percentage may be taken either as a cutoff for assay validity or for as an indication that the sample should be enriched by Ficoll centrifugation. This criterion, however, may be too stringent since the methylation patterns of non-blast cells may not be identical to that found in normal peripheral blood cells. Similarly, the total amount of DNA used for MELP analysis does not significantly change the MELP risk score across a range of concentrations. Thus, establishing a lower limit of total DNA cannot be based on risk score reproducibility.

Decreasing the amount of source DNA, however, does increase the chances that the assay will fail the quality control requirements that were established. Hence, performing the assay with low amounts of DNA (e.g., <10 ng) may not be cost or time effective, but results from low amounts of DNA may yield valid results provided that they pass the established quality control standards. Of note, however, one sample showed significant deviations from standard xMELP when DNA levels were <50 ng; thus, further work may be required to fully explore the behavior of xMELP at these boundary conditions.

The analysis of the MELP data is somewhat complex and utilizes a random forest classifier to determine the methylation risk score. In the analysis of the MELP data, a number of multiple-variable analytic approaches were tried, including the SuperPC algorithm used in the original HELP and MELP analysis of AML (6, 28), and found that the random forest method yielded robust results. Further, the multiplex classifier, described herein, has the property of retaining its predictive value even if a single locus yields an erroneous value.

Assay precision both at the individual locus level and in terms of overall methylation risk is likely sufficient for clinical use. Compared to inter-sample variation across 207 samples, the intra-sample variability of is minimal at most loci analyzed, including all of the loci that are included in the 17-locus methylation classifier. Formal testing of the methylation risk score variation using 21 replicates of the same sample shows a % CV of ~15% and further testing showed little variation in six samples when tested in duplicate. Additional indications of test reproducibility were obtained from experiments in which DNA from AML patients was diluted with either water or with DNA from normal peripheral blood. Normal blood DNA also showed a similar methylation risk score in replicate sample measurements, again underscoring the reproducibility of the assay. Importantly, when the UPenn AML cohort were divided into prognostic tertiles, 5/6 replicates are found within the same tertile. Although small variations in risk score can change tertile assignment for samples at the borders of the groups, repeat testing of borderline specimens may ameliorate the risk of misclassification. Of course, the random forest survival analysis yields a continuous risk score, so results may be reported quantitatively rather than categorically. Overall, these results indicate a high level of confidence is associated with subgroup classification based on xMELP determined DNA methylation.

Since an AML cohort (UPenn samples) that was entirely independent of the original HOVON AML cohort and was obtained collected from another institution, the full HOVON sample set was used to train a methylation based classifier prior to testing the classifier on the UPenn data set. This scenario is distinct from previous work in which the HOVON dataset was randomly divided into training and test subsets (6, 15). The addition of samples to the training set, along with the re-analysis of HELP data for inclusion of additional informative loci, the elimination of ultimately uninformative loci, and the use of the random forest algorithm furthered the optimization of the xMELP risk score. Importantly, testing the xMELP AML risk score on a subset of the UPenn samples for which outcome data has been obtained clearly shows that an xMELP assay can segregate AML patients with distinct outcomes. Importantly, this validation cohort was collected at a different institution and on a different continent than the training cohort. This analysis is currently being expanded to include the remaining samples in the UPenn cohort and will use the full set to conduct a multivariate analysis to test the independent prognostic power of xMELP-derived DNA methylation patterns.

Further studies will also attempt to develop an integrated, global prognosis classification scheme for AML using all available factors (including DNA methylation) currently known to influence patient prognosis.

Taken together, these studies strongly suggest that xMELP, in conjunction with the analytic methods developed, is a powerful assay for determining outcome in patients with AML. This prognostic power, as well as the reproducibility of xMELP, rapid turnaround time, and simplicity of the assay, demonstrates its suitability for use in clinical molecular diagnostics laboratories as a standard test in patients with AML. Given its general applicability, xMELP also warrants further exploration as a clinical assay (most likely utilizing other loci and bioinformatics classifiers) for other diseases in which DNA methylation patterns strongly influence clinical outcomes.

TABLE 1

| HELP MELP Locus ID | Chromosome | Start | Stop | Classifier |
|---|---|---|---|---|
| MSPI0406S00783415 | chr17 | 2208021 | 2208391 | + |
| MSPI0406S00920592 | chr20 | 32274469 | 32275009 | + |
| MSPI0406S00304798 | chr6 | 3024925 | 3025589 | |
| MSPI0406S00196536 | chr3 | 129274773 | 129275235 | + |
| MSPI0406S00697563 | chr14 | 105860849 | 105861218 | |
| MSPI0406S00011246 | chr1 | 11723172 | 11723834 | + |
| MSPI0406S00861109 | chr19 | 1924052 | 1924259 | + |
| MSPI0406S00333894 | chr6 | 108615428 | 108615973 | + |
| MSPI0406S00754805 | chr16 | 30538940 | 30539797 | + |
| MSPI0406S00613804 | chr12 | 53661106 | 53661621 | + |
| MSPI0406S00176846 | chr3 | 48601900 | 48602237 | |
| MSPI0406S00715593 | chr15 | 65810129 | 65810776 | + |
| MSPI0406S00698115 | chr14 | 106354882 | 106355276 | + |
| MSPI0406S00600078 | chr12 | 6233715 | 6234255 | + |
| MSPI0406S00914183 | chr20 | 11899205 | 11899843 | + |
| MSPI0406S00710190 | chr15 | 50838542 | 50839225 | + |
| MSPI0406S00163833 | chr3 | 8542436 | 8543339 | + |
| MSPI0406S00765490 | chr16 | 68345197 | 68345691 | + |
| MSPI0406S00914182 | chr20 | 11898849 | 11899205 | + |
| MSPI0406S00914181 | chr20 | 11898555 | 11898849 | + |
| MSPI0406S00997890 | chrX | 48795887 | 48797005 | |
| MSPI0406S00838340 | chr18 | 5293969 | 5294770 | |
| MSPI0406S00136939 | chr2 | 158114266 | 158115184 | + |
| MSPI0406S00669709 | chr14 | 24867489 | 24867729 | |
| MSPI0406S00027418 | chr1 | 32739167 | 32739750 | |
| MSPI0406S00589152 | chr11 | 118763110 | 118763426 | |
| MSPI0406S00910305 | chr20 | 814970 | 815202 | |
| MSPI0406S00708912 | chr15 | 45003463 | 45004002 | |
| MSPI0406S00318682 | chr6 | 34856156 | 34857019 | C |
| MSPI0406S00653944 | chr13 | 53028642 | 53029495 | C |
| MSPI0406S00890278 | chr19 | 37958559 | 37958860 | C |

List of loci used in the xMELP assay. HELP/MELP 1 D numbers with corresponding genomic location (hg19 assembly) are indicated. The loci used in the final classifier are shown indicated with (+). The control loci used in the classifier are marked as "C."

TABLE 2

| Locus ID | Chromosome | Start | Stop | Locus Symbol | Gene Card ID |
|---|---|---|---|---|---|
| MSPI0406S00783415 | chr17 | 2208021 | 2208391 | SMG6 | GC17M001963 |
| MSPI0406S00920592 | chr20 | 32274459 | 32275009 | E2F1 | GC20M032263 |
| MSPI0406S00304798 | chr6 | 3024925 | 3025589 | — | |
| MSPI0406S00196536 | chr3 | 129274773 | 129275235 | PLXND1 | GC03M129274 |
| MSPI0406S00697563 | chr14 | 105860849 | 105861218 | BC127913 | |
| MSPI0406S00011246 | chr1 | 11723172 | 11723834 | FBXO6 | GC01P011724 |
| MSPI0406S00861109 | chr19 | 1974052 | 1924259 | — | |
| MSPI0406S00333894 | chr6 | 108615428 | 108615973 | LACE1 | GC06P108616 |
| MSPI0406S00754805 | chr16 | 30538940 | 30539797 | ZNF768 | GC16M030535 |
| MSPI0406S00613804 | chr12 | 53661106 | 53661621 | ESPL1 | GC12P053662 |
| MSPI0406S00176846 | chr3 | 48601900 | 48602237 | UCN2 | GC03M048599 |
| MSPI0406S00715593 | chr15 | 65810129 | 65810776 | DPP8 | GC15M065734 |
| MSPI0406S00698115 | chr14 | 106354882 | 106355276 | KIAA0125 | GC14P106383 |
| MSPI0406S00600078 | chr12 | 6233715 | 6234255 | VWF | GC12M006058 |
| MSPI0406S00914183 | chr20 | 11899205 | 11899843 | BTBD3 | GC20P011866 |
| MSPI0406S00710190 | chr15 | 50838542 | 50839225 | USP50 | GC15M050792 |
| MSPI0406S00163833 | chr3 | 8542436 | 8543339 | LMCD1 | GC03P008518 |
| MSPI0406S00765490 | chr16 | 68345197 | 68345691 | SLC7A6OS/PRMT7 | GC16M068320/GC16P068344 |
| MSPI0406S00914182 | chr20 | 11898849 | 11899205 | BTBD3 | GC20P011866 |
| MSPI0406S00914181 | chr20 | 11898555 | 11898849 | BTBD3 | GC20P011866 |
| MSPI0406S00997890 | chrX | 48795887 | 48797005 | — | |
| MSPI0406S00838340 | chr18 | 5293969 | 5294770 | ZFP161 | GC18M005289 |
| MSPI0406S00136939 | chr2 | 158114266 | 158115184 | GALNT5 | GC02P158079 |
| MSPI0406S00669709 | chr14 | 24867489 | 24867729 | NYNRIN | GC14P024868 |

TABLE 2-continued

| Locus ID | Chromosome | Start | Stop | Locus Symbol | Gene Card ID |
| --- | --- | --- | --- | --- | --- |
| MSPI0406S00027418 | chr1 | 32739167 | 32739750 | LCK | GC01P032716 |
| MSPI0406S00589152 | chr11 | 118763110 | 118763426 | CXCR5 | GC11P118754 |
| MSPI0406S00910305 | chr20 | 814970 | 815202 | FAM110A | GC20P000762 |
| MSPI0406S00708912 | chr15 | 45003463 | 45004002 | B2M | GC15P045003 |
| MSPI0406S00318682 | chr6 | 34856156 | 34857019 | TAF11 | GC06M035734 |
| MSPI0406S00653944 | chr13 | 53028642 | 53029495 | VPS36 | GC13M052986 |
| MSPI0406S00890278 | chr19 | 37958559 | 37958860 | ZNF569 | GC19M037902 |

HELP/MELP ID numbers and their corresponding genomic location (hg19 assembly), locus symbol and gene card ID.

Example 2: Optimization of the xMELP Diagnostic Assay

Introduction

The ability to predict therapeutic response is essential for improving care of patients with acute myeloid leukemia (AML). Established prognostic schemes in AML are based on 1) clinical features and 2) pre-treatment karyotype but incompletely predict outcome. Recent efforts to understand AML variability have focused on the relationship between epigenetic abnormalities—including changes in DNA cytosine methylation—and AML phenotype. DNA methylation patterns differ between leukemic cells and normal progenitor cells, and distinct methylation signatures have been described in AML subgroups (6, 43-44).

While the mechanism by which aberrant methylation contributes to neoplasia remains incompletely understood, epigenetic alterations show significant correlation with patient outcome in several hematologic malignancies, including AML (6, 7, 10, 30-32). Despite the recognized relationship between DNA methylation and AML prognosis, clinical methylation assessment is not routine due to lack of a rapid, reliable assay and a prognostic biomarker that provides validated prognostic information. As described herein, a novel microsphere-based assay for simultaneous assessment of DNA methylation status at multiple prognostic loci was developed using commonplace clinical laboratory techniques (6, 15, 16). This assay—xMELP—is an adaptation of the well-established HpaII Tiny Fragment Enrichment by Ligation Mediated PCR (HELP) assay. Example 1 above describes the technical parameters of xMELP, including precision, locus specificity, analytic sensitivity and turn-around time, which are appropriate for clinical use (15, 33).

In conjunction with a 17-locus xMELP assay, a methylation risk score (M-score) was developed for AML using a random forest classification method, as described in Example 1, to demonstrate the association between the M-score and overall survival (OS) in a cohort of AML patients (33).

Methods and Materials

Study Population and Patient Samples

UPenn Cohort.

183 consecutive patients with de novo AML (34) at the University of Pennsylvania (UPenn) who consented to donation of a diagnostic sample to the Hematologic Malignancies Tissue Bank of the University of Pennsylvania between 2001 and 2012, had adequate quality DNA for analysis, and consented to review of their medical records. Standard molecular (FLT3-ITD and NPM1) and cytogenetic studies were available for 166 samples. Cytogenetic risk was classified according to the Medical Research Council (MRC) criteria (29). FLT3-ITD and NPM1 status was assessed in a CLIA-certified lab and classified as mutant or wildtype. For 136 patients, more extensive molecular information was available from targeted next-generation sequencing. Patient and disease characteristics, treatment, and clinical outcomes were obtained from medical records. Median follow-up was 68.1 months (range, 1.4 to 150.2) among 38 survivors and 10.5 months (range, 0.1 to 95.2) among those (n=128) deceased.

E1900 Cohort.

The validation cohort was comprised of 383 patients who enrolled on Eastern Cooperative Oncology Group (ECOG) Trial 1900 (E1900) between 2002 and 2008 who had available DNA methylation, genetic, and clinical data. Methylation data is publically available (Gene Expression Omnibus repository accession number GSE24505 [http://www.ncbi.nlm.nih.gov/geo]) (6). Patients with indeterminate cytogenetics were analyzed with the intermediate risk patients. Median follow-up was 83.2 months (range, 0.8 to 120.4) among 108 survivors and 11.0 months (range, 0.2 to 77.5) among those (n=275) deceased. Institutional review board approval was obtained from the University of Pennsylvania and the Eastern Cooperative Oncology Group.

Samples, xMELP and the M-Score

DNA extraction and the xMELP assay were performed on UPenn samples as described in Example 1 (See also 15, 33). The M-score of each sample was determined using the random forest classification algorithm previously trained on an independent cohort of 344 AML samples collected by the Dutch-Belgian Hemato-Oncology Cooperative Group (HOVON) (R-scripts for M-score derivation are previously described and publicly available) (as described in Example 1 and reference 33). For ECOG samples (i.e., the E1900 samples), HELP-derived methylation data was transformed to MELP-associated values using previously described regression coefficients (15).

Treatment

UPenn Cohort.

The induction chemotherapy regimen in all cases included an anthracycline and cytarabine. Patients with residual leukemia at Nadir bone marrow assessment were frequently re-treated with an anthracycline-based regimen or high-dose cytarabine at the clinicians' discretion. The primary clinical endpoints were failure to achieve complete remission (CR) within 90 days of induction and OS. OS was time from induction chemotherapy to death from any cause; for patients alive at last follow-up OS times were censored. CR was defined as morphologic leukemic-free state on bone marrow examination after 1 or 2 cycles of induction chemotherapy (with assessment required to be within 90 days of induction chemotherapy) (34).

E1900 Cohort.

The treatment schema and endpoint definitions for the E1900 cohort have been previously described (35). E1900 was a randomized trial of high dose versus standard dose daunorubicin that accrued patients aged≤60 from 2002-2008 (NCT00049517).

Statistical Analysis

Continuous variables were summarized by median and range, and categorical variables by count and relative frequency. Comparisons of M-score between groups of AML patients were assessed by the parametric unpaired two-sample t-test (adjusted using Satterthwaite's method when variances unequal) and ANOVA test (for comparing≥2 groups). The association between M-score and blast percentage was assessed by Pearson's correlation coefficient.

Univariate and multivariable logistic models were used to assess the association of the M-score with response to induction chemotherapy (failure to achieve CR) alone and controlling for covariates including age, sex, white blood cell (WBC) count at diagnosis, cytogenetics and molecular status. Survival distributions for OS were computed using the Kaplan-Meier method with assessment of differences between exposure groups computed using the log-rank test. Univariate and multivariable Cox regression analyses were used to examine the association of M-score and OS controlling for the same covariates. Backward selection was used in multivariable logistic and Cox models to develop the most parsimonious model.

An optimal cut-point for the M-score was determined by identifying the cut-point that maximized the log-rank statistic between "high" and "low" M-score groups. P values were considered significant when<0.05 (two-sided). Analyses were performed using Stata 12.1 (StataCorp LP). The "high" M-score was determined to be greater than 86 and the "low" M-scores were determined to be 86 or lower.

Results

M-Score is not Associated with Patient or Sample Characteristic

In total, 166 patients with de novo AML who underwent induction therapy with anthracycline and cytarabine at the University of Pennsylvania (2001-2012), had available genetic data, and donated a diagnostic sample available for xMELP analysis were analyzed (Table 3). Of the 166 patients, 52 (31%) were ≥60 and 35 (21%) had a WBC count at diagnosis≥100 K/uL (Table 3). The majority of patients had intermediate cytogenetic risk (13% favorable, 71% intermediate, 16% unfavorable) (Table 3). In response to 1 or 2 cycles of induction chemotherapy, 71% achieved CR and 38% were alive 2 years after starting treatment (Table 4).

Figure 12:
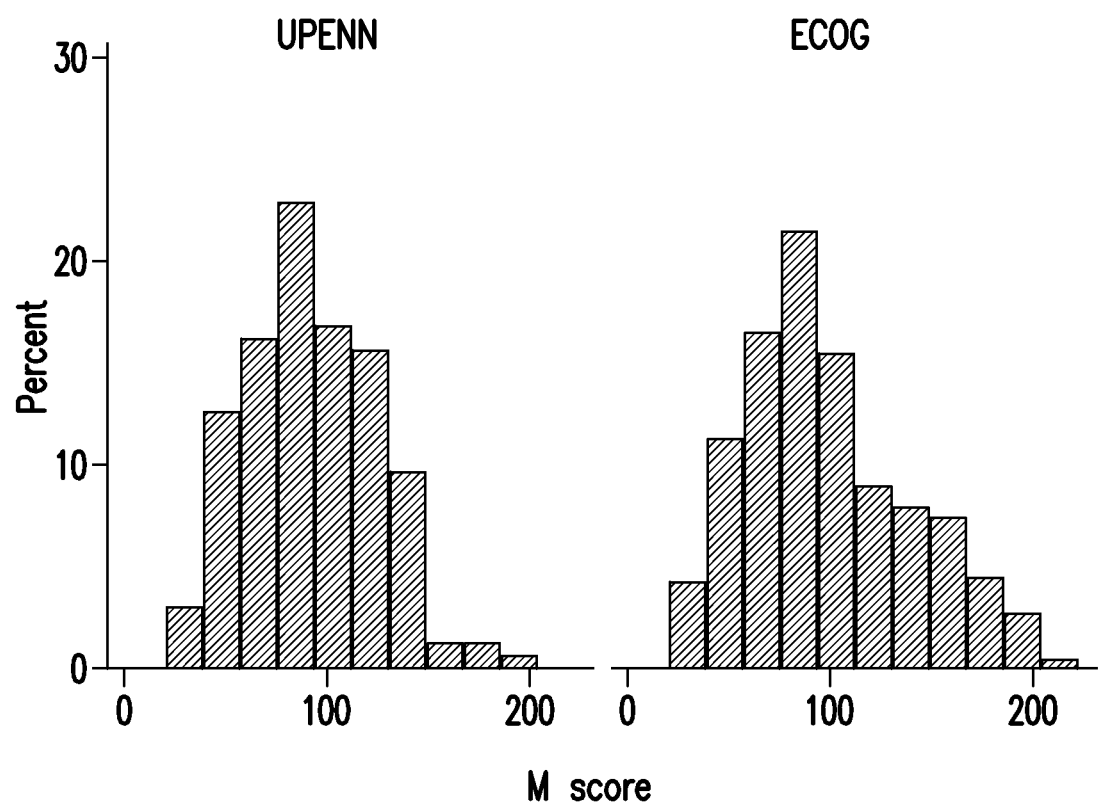
FIG. 12. M-score distribution for the UPenn and E1900 (ECOG) cohorts.

DNA methylation status at 17 previously identified prognostic loci was assessed by xMELP on a diagnostic sample from each patient, and the M-score statistic was calculated using the previously trained algorithm (See Example 1 and reference 33). The mean and median M-score for the UPenn cohort was 92.3 (95% confidence interval [CI], 87.4 to 97.2) and 91.4 (range, 30.8 to 197.3), respectively (FIG. 12). M-score was not significantly associated with patient age or gender (Table 3), specimen type (blood vs. bone marrow vs. pheresis sample, P=0.809) or blast percentage (P=0.415).

M-Score is Significantly Associated with AML Clinical Response

Figure 8:
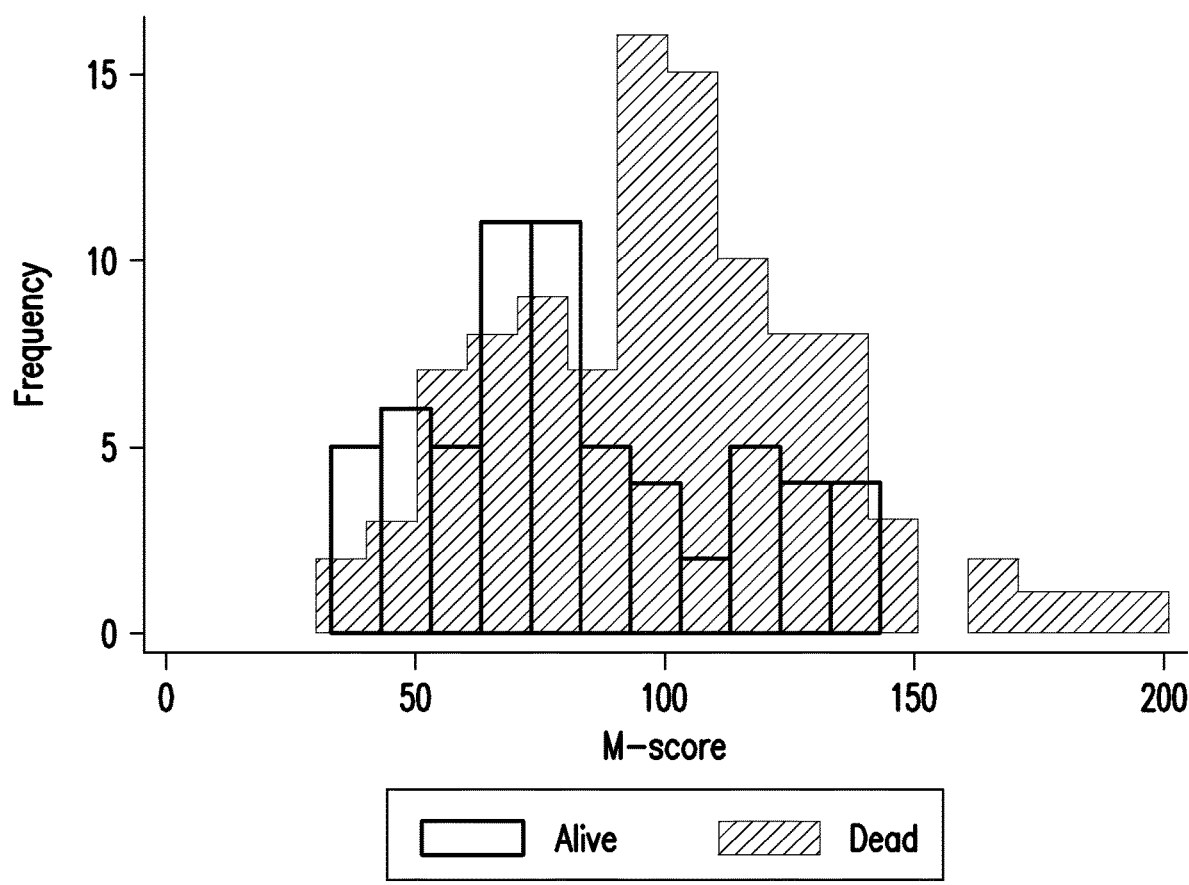
FIG. 8. Distribution of M-score by survival status at 2 years in the UPenn Cohort (n=163, n=3 with unknown survival status at 2 years excluded).

In order to determine the association of M-score with AML clinical response, the relationships between the M-score and both survival and ability to achieve remission were examined. The distribution of M-score by survival status at 2 years is shown in FIG. 8. The mean M-score for surviving patients was significantly lower (81.8) than for deceased patients (99.5) (81.8; 95% CI, 74.3 to 89.2 vs. 99.5; 95% CI 93.2 to 105.8, P=0.0005). Similarly, the mean M-scores were 86.8 versus 105.8 for those who achieved and failed to achieve CR, respectively (86.8; 95% CI, 81.3 to 92.4 vs. 105.8; 95% CI, 96.5 to 115.0, P=0.0005). Additionally, a univariate Cox survival analysis demonstrated that a 10-unit increase in the M-score was associated with a 10% increase in the hazard of death (P<0.0001, Table 5) and a 10-unit increase in the M score was associated with a 10% increase in the odds of failing to achieve CR (Table 6).

M-Score is Associated with OS and Failure to Achieve CR in Multivariable Models

Given the association of genetic characteristics and outcome in AML, the association of M-score with AML genetic characteristics were assessed (Table 3). As shown in Table 3, the M-score differed among the 3 cytogenetic risk groups: the favorable cytogenetics group had a lower mean M-score than both the intermediate and unfavorable groups (P<0.0001 and P=0.001, respectively) but there was no difference in mean M-score between intermediate and unfavorable groups (P=1.0). Patients that had a favorable cytogenetic risk had an average M-score of 66.1; whereas patients that had intermediate cytogenetics had a mean M-score of 95.4 and those with an unfavorable cytogenetic risk had an average M-score of 99.1.

The M-score was not associated with established molecular markers of AML risk (NPM1 and FLT3-ITD, Table 3) but was associated with mutations in DNMT3A and IDH1, two genes involved in regulation of DNA methylation. M-score was not, however, associated with mutation in other methylation regulators including IDH2, TET2, or WT1 (Table 8).

Multivariable analyses were next performed to determine if the M-score was independently associated with OS and CR. In multivariable Cox analysis, higher M-score and older age were associated with increased hazard of death, while NPM1+/FLT3-ITD-status was associated with decreased hazard of death (Table 5). Interestingly, the reduced multivariable model for survival included only age and NPM1+/FLT3-ITD-status in addition to M-score (Table 5). Similarly, in a multivariable logistic analysis, M-score was associated with increased odds of failing to achieve CR. The reduced (parsimonious) multivariable model for failure to achieve CR included M-score, age, and cytogenetics (Table 6). The association between M-score and hazard of death and odds of achieving CR was not significantly different between younger (≤60 years) and older (>60 years) patients.

Additional multivariable Cox and logistic regression analyses including DNMT3A and IDH1 conducted on the subset of patients with extended molecular data (n=136) confirmed that M-score remained significantly associated with survival and achievement of CR (Tables 9 and 10). Notably, NPM1+/FLT3− was the only genetic marker included in both reduced Cox models, suggesting that M-score is more strongly associated with AML outcome than most individual genetic markers.

Risk Classification Using the M-Score

Figure 9:
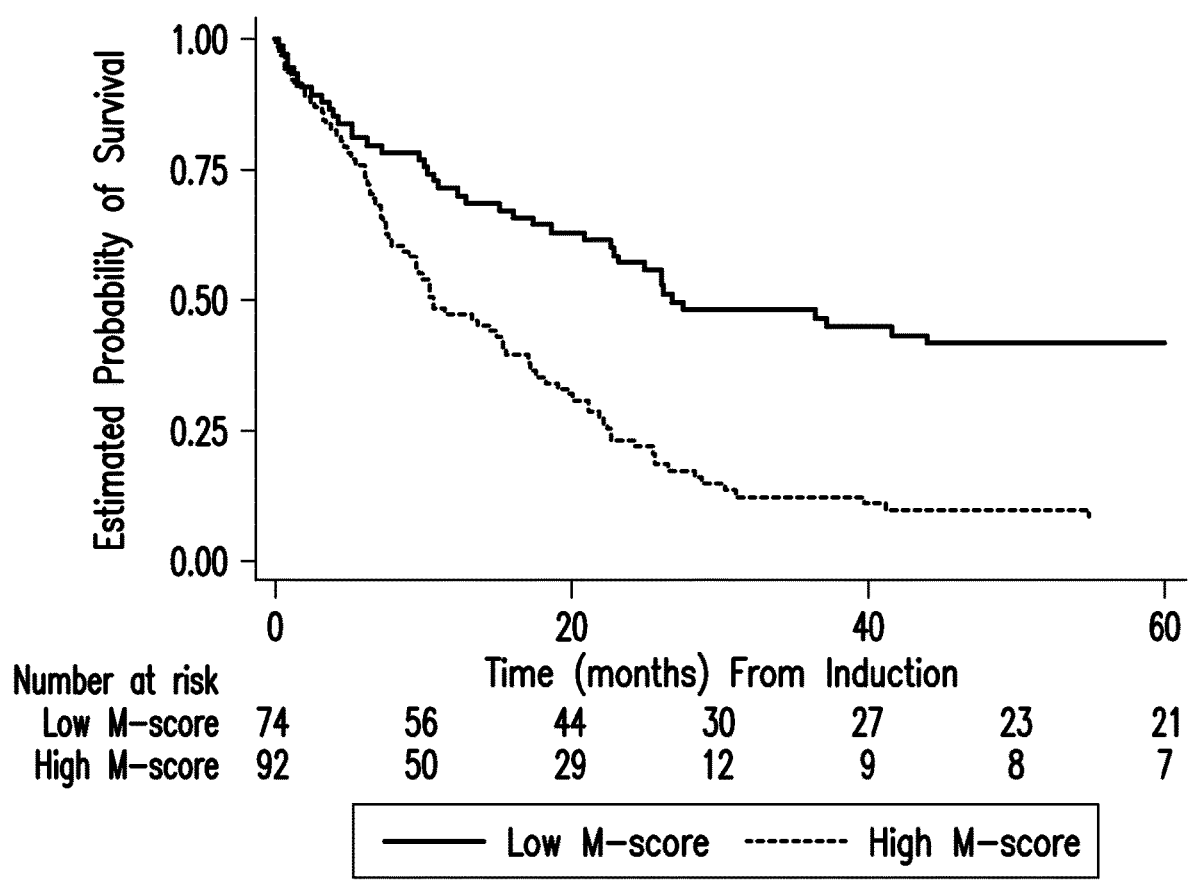
FIG. 9. Kaplan-Meier curves of overall survival in the UPenn cohort. Subgroups are determined by the optimal M-score. Curves for the total cohort (n=166) are shown.
Figure 13:
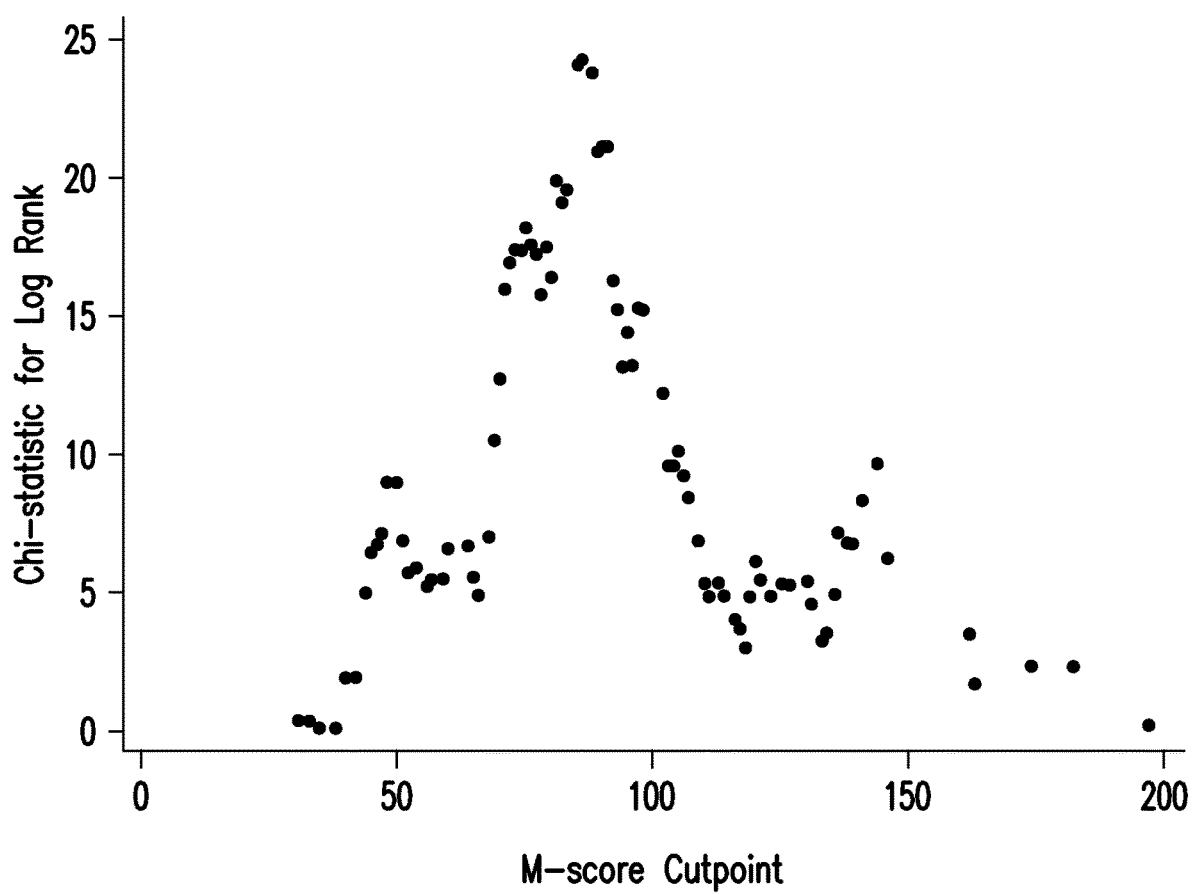
FIG. 13. Chi-statistic by M-score cutpoint in the UPenn cohort (Optimal cutpoint determined to be 86).
Figure 16:
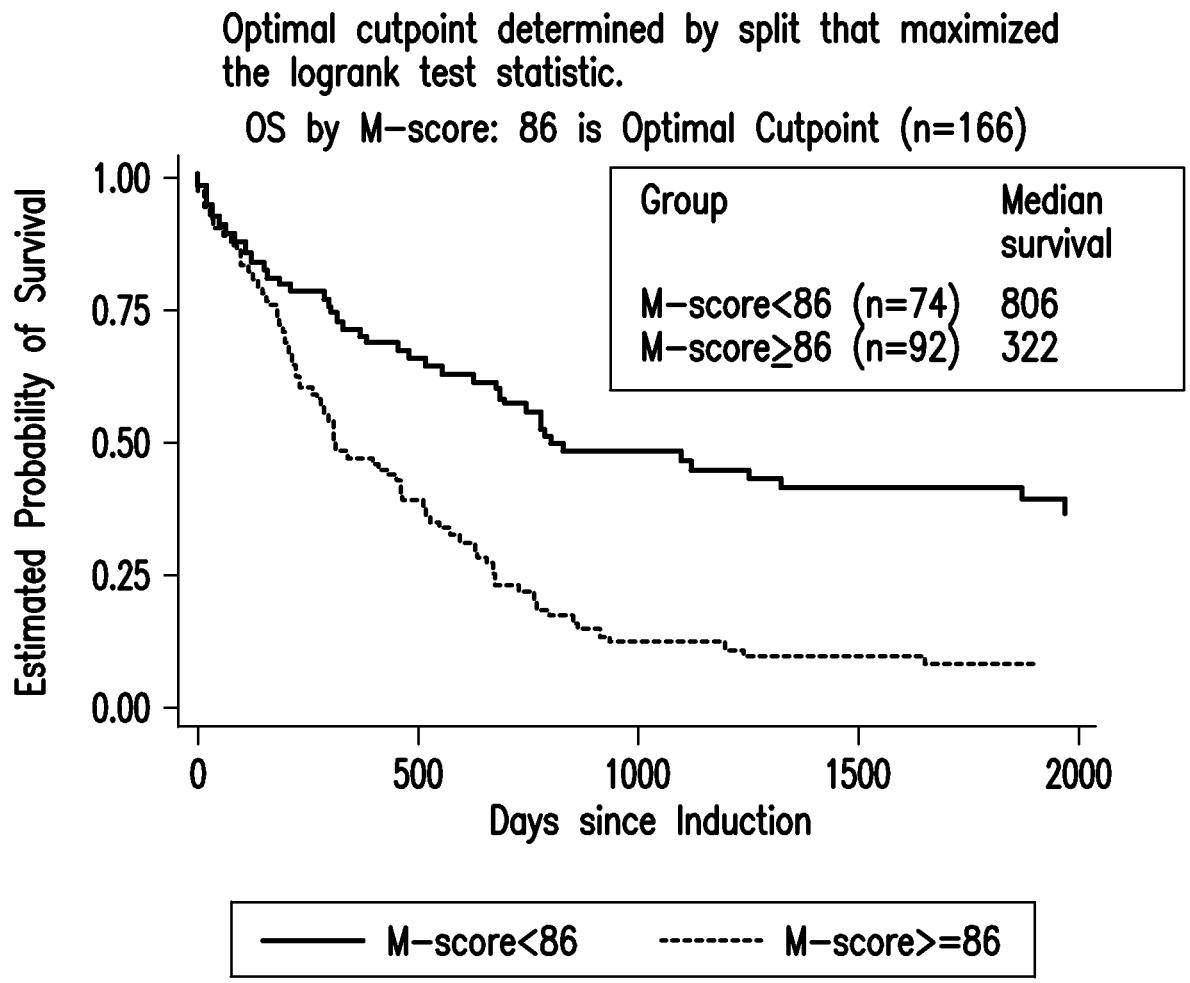
FIG. 16. An exemplary M-score cutpoint according to a non-limiting embodiment of the present disclosure.

After confirming the independent association of M-score with clinical outcome in AML, a risk classifier for clinical application was designed. Based on the maximization of the log-rank statistic, the optimal binary M-score cutpoint was determined to be 86 in the UPenn cohort (FIGS. 13 and 16). Using the optimal cutpoint, a binary M-score classifier was defined. The binary classifier identified two groups in the UPenn cohort—low and high M-score groups. The Kaplan-Meier curves for the low and high M-score groups are shown in FIG. 9 (characteristics of the 2 groups are described in Table 11). A high M-score was associated with an increased hazard of death alone (HR 2.5, P<0.0001) and after adjustment for all other factors (HR 1.9, P=0.003). Median survival for the low and high M-score groups was 26.6 and 10.6 months; 2-year OS was 56% (95% CI, 43.8 to 67.3) and 24% (95% CI, 15.2 to 33.1) (Table 7). The CR rate for low and high M-score group was 84% (95% CI, 75.2 to 92.4) and 61% (95% CI, 50.7 to 71.0; P=0.001), respectively (Table 7).

Figure 10:
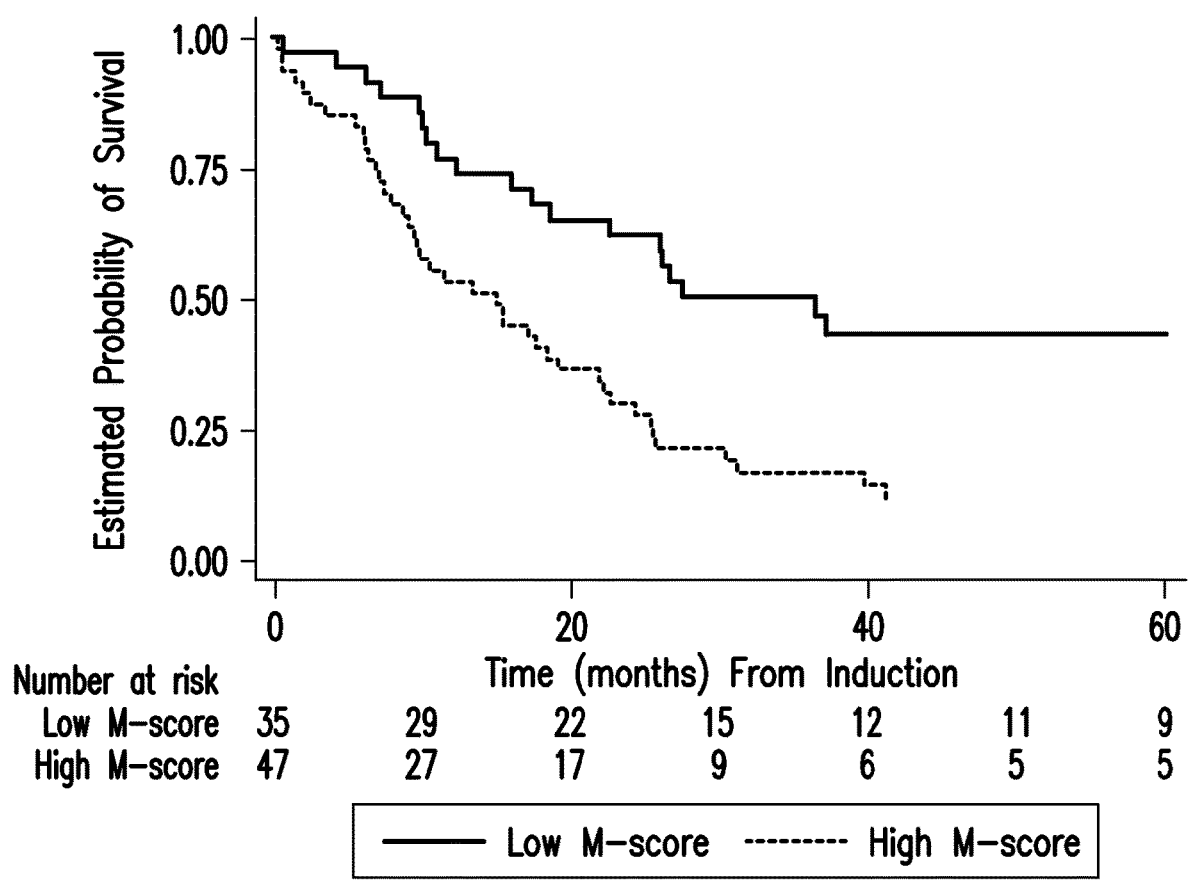
FIG. 10. Kaplan-Meier curves of overall survival in the UPenn cohort. Subgroups are determined by the optimal M-score. Curves for patients≤60 years with intermediate cytogenetics (n=82; log-rank P=0.001) are shown.

AML patients aged≤60 years with intermediate cytogenetics are in particular need of new tools for risk stratification; therefore, the binary M-score classifier was evaluated in this subgroup (described in Table 3). Standard prognostic factors were not different between patients with low and high M-scores within this subgroup (Table 11). The classifier defined groups with significantly different OS (log-rank P=0.001; FIG. 10). Median survival was 36.4 versus 14.9 months in the low and high M-score groups, respectively (Table 7). Additionally, more patients in the low M-score group were alive at 2 years (62% vs. 30%, P=0.004) and achieved CR (91% vs. 70%, P=0.019).

Figure 14:
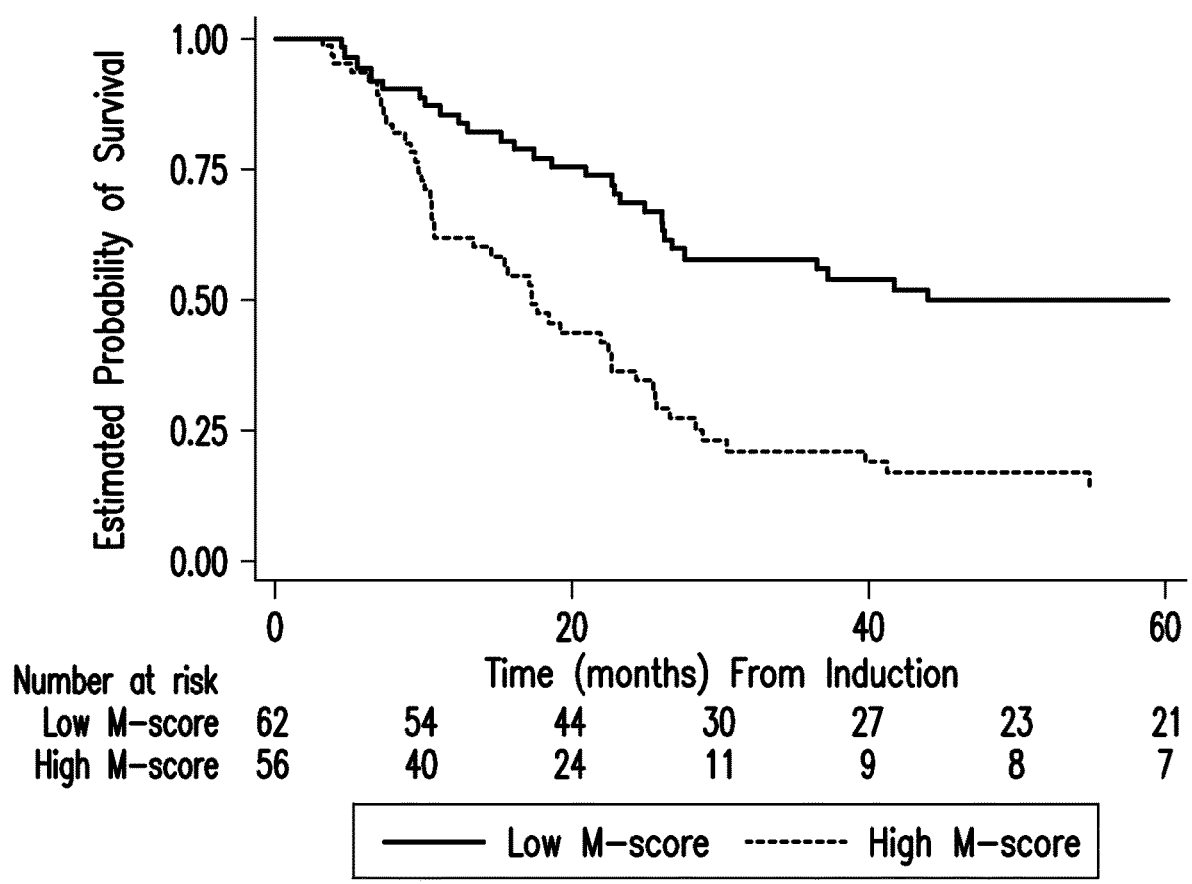
FIG. 14. Kaplan-Meier curves of overall survival in UPenn patients who achieved complete remission (n=118; log-rank P<0.00001).

Finally, to investigate whether the ability of the M-score classifier to define groups with different OS was merely a reflection of achievement of CR, analysis was restricted to the 118 patients who had achieved CR. The M-score classifier continued to identify patients with significantly different OS (log-rank P<0.00001; FIG. 14) with median survival 43.9 versus 17.2 months in low and high-risk groups, respectively (Table 7). In this group, the 2-year OS was 67% in the low M-score group versus 36% in the high M-score group (P=0.001). Additionally, it was noted that patients with high M-score were more likely to need 2 cycles of induction chemotherapy than those with a low M-score to achieve CR (29% vs. 6%, P=0.001).

TABLE 3

UPenn Cohort: M-score by Patient and AML Characteristics.

| | Total Cohort n = 166 | | | | | Age ≤60, Intermediate Cytogenetics (n = 82) | | | | |
|---|---|---|---|---|---|---|---|---|---|---|
| | n | % | M-score (Mean) | 95% CI | P | n | % | M-score (Mean) | 95% CI | P |
| All Subjects | 166 | 100 | 92.3 | 87.4-97.2 | — | 82 | 100 | 94.2 | 87.0-101.5 | — |
| Age (years), diagnosis | | | | | | | | | | |
| ≤60 | 114 | 68.7 | 90.6 | 84.6-96.5 | .297 | — | — | — | — | — |
| >60 | 52 | 31.3 | 96.2 | 87.4-105.0 | | — | — | — | — | — |
| Sex | | | | | | | | | | |
| Male | 98 | 59.0 | 90.8 | 84.2-97.5 | .476 | 46 | 56.1 | 92.1 | 81.9-102.3 | .516 |
| Female | 68 | 41.0 | 94.4 | 87.1-101.8 | | 36 | 43.9 | 96.9 | 86.3-107.5 | |
| WBC (×10⁹/L), diagnosis | | | | | | | | | | |
| <100 | 131 | 78.9 | 935 | 87.7-99.4 | .262 | 59 | 72.0 | 95.4 | 86.3-104.6 | .604 |
| ≥100 | 35 | 21.1 | 87.8 | 79.3-96.2 | | 23 | 28.0 | 91.2 | 79.5-102.9 | |
| Cytogenetic risk group* | | | | | | | | | | |
| Favorable | 21 | 12.7 | 66.1 | 57.0-75.2 | .0002 | — | — | — | — | — |
| Intermediate | 118 | 71.1 | 95.4 | 89.6-101.3 | | — | — | — | — | — |
| Unfavorable | 27 | 16.3 | 99.1 | 86.9-111.3 | | — | — | — | — | — |
| FLT3-ITD | | | | | | | | | | |
| Mutant | 56 | 33.7 | 93.4 | 86.5-100.2 | .742 | 37 | 45.1 | 92.9 | 83.5-102.3 | .744 |
| Wild type | 110 | 66.3 | 91.8 | 85.2-98.4 | | 45 | 54.9 | 95.3 | 84.3-106.3 | |
| NPM1 | | | | | | | | | | |
| Mutant | 58 | 34.9 | 93.3 | 84.0-96.9 | .549 | 38 | 46.3 | 89.5 | 81.1-97.9 | .212 |
| Wildtype | 108 | 65.1 | 90.5 | 86.5-100.1 | | 44 | 53.7 | 98.4 | 86.8-109.9 | |
| NPM1+/FLT3-ITD− | | | | | | | | | | |
| Yes | 25 | 15.1 | 84.3 | 74.9-93.7 | .084 | 17 | 20.7 | 83.1 | 74.1-92.1 | .025 |
| No | 141 | 84.9 | 93.7 | 88.2-99.3 | | 65 | 79.3 | 97.1 | 86.4-105.9 | |

*Medical Research Council criteria (2010)
AML, acute myeloid leukemia;
WBC, white blood cell;
FLT3-ITD, FMS-like kinase 3-internal tandem duplication;
NPM1, nucleophosmin

TABLE 4

AML Treatment and Clinical Outcome for the UPenn Cohort.

| | Total Cohort (n = 166) | | Age ≤60, Intermediate Cytogenetics (n = 82) | |
|---|---|---|---|---|
| | n | % | n | % |
| First Induction | | | | |
| Dauno 45/Ara-C | 51 | 30.7 | 18 | 18.4 |
| Dauno 60/Ara-C | 8 | 4.8 | 0 | 0.0 |
| Dauno 90/Ara-C | 26 | 15.4 | 18 | 22.0 |
| Ida 12/Ara-C | 71 | 42.8 | 46 | 56.1 |
| Mito 10/Ara-C | 9 | 5.4 | 1 | 2.3 |
| Unconfirmed | 2 | 1.2 | 2 | 1.8 |

TABLE 4-continued

AML Treatment and Clinical Outcome for the UPenn Cohort.

|  | Total Cohort (n = 166) | | Age ≤60, Intermediate Cytogenetics (n = 82) | |
|---|---|---|---|---|
|  | n | % | n | % |
| Second Induction | | | | |
| Yes | 45 | 27.1 | 21 | 25.6 |
| Anthracymine Ara-C | 26 | 15.7 | 9 | 11.1 |
| MEC | 11 | 6.6 | 6 | 7.3 |
| High-dose Ara-C | 8 | 4.8 | 6 | 7.3 |
| No | 119 | 71.7 | 59 | 72.0 |
| Unknown | 2 | 1.2 | 2 | 1.8 |
| CR | | | | |
| Yes | 148 | 71.4 | 65 | 79.3 |
| No | 48 | 28.9 | 17 | 20.7 |
| 2-Year OS | | | | |
| Yes | 62 | 38.0 | 35 | 43.2 |
| No | 101 | 52.0 | 46 | 56.8 |

AML, acute myeloid leukemia;
Dauno 45/Ara-C, 3 once daily doses of daunorubicin 45 mg/m² plus 7 daily doses of cytarabine 100 mg/m² by continuous infusion;
Dauno 60/Ara-C, 3 once daily doses of daunorubicin 60 mg/m² plus 7 daily doses of cytarabine 100 mg/m² by continuous infusion;
Dauno 90/Ara-C, 3 once daily doses of daunorubicin 90 mg/m² plus 7 daily doses of cytarabine 100 mg/m² by continuous infusion;
Ida 12/Ara-C, 3 once daily doses of idarubicin 12 mg/m² plus 7 daily doses of cytarabine 100 mg/m² by continuous infusion;
Mito 10/Ara-C; 3 once daily doses of mitoxantrone 10 mg/m² plus 7 daily doses of cytarabine 100 mg/m² by continuous infusion;
MEC, 6 once daily doses of mitoxantrone 6 mg/m², 8 daily doses of etoposide 80 mg/m²; plus 6 daily doses of cytarabine 1 g/m²;
High-dose Ara-C, 1.5 or 3 gm/m² twice daily on days 1, 3, and 5;

TABLE 5

UPenn Cohort: Cox Model for Overall Survival (n = 166, events = 128).

| Parameter | Univariate | | Multi-variable Adj | | Reduced Adj | 95% CI | P |
|---|---|---|---|---|---|---|---|
|  | HR | P | HR | P | HR | CI | P |
| M-score# | 1.1 | <.0001 | 1.1 | .011 | 1.1 | 1.0-1.2 | .002 |
| Age% | 1.3 | <.0001 | 1.3 | .001 | 1.3 | 1.1-1.5 | <.0001 |
| Female | 1.1 | .461 | 1.1 | .579 | — | — | — |
| WBC, diagnosis# | 1.0 | .856 | 1.0 | .210 | — | — | — |
| Cytogenetic Risk* (reference unfavorable) | | | | | | | |
| Intermediate | 0.7 | .085 | 0.7 | .226 | — | — | — |
| Favorable | 0.3 | .002 | 0.5 | .067 | — | — | — |
| FLT3-ITD+ | 1.4 | .099 | 1.1 | .733 | — | — | — |
| NPM1+/FLT3-ITD− | 0.5 | .017 | 0.5 | .031 | 0.5 | 0.3-0.8 | .011 | divided by 10;
%10-year increase;
*Medical Research Council critera (2010)
Hazard ratio, HR;
CI, confidence interval;
WBC, white blood cell;
FLT3-ITD, FMS-like kinase 3-internal tandem duplication;
NPM1, nucleophosmin1

TABLE 6

UPenn Cohort: Logistic Model for Failure to Achieve Complete Remission (n = 166, events = 48).

| Parameter | Univariate OR | P | Multi-variable Adj OR | P | Reduced Adj OR | 95% CI | P |
|---|---|---|---|---|---|---|---|
| M-score# | 1.2 | .001 | 1.1 | .034 | 1.2 | 1.0-1.3 | .012 |
| Age% | 1.5 | .002 | 1.5 | .007 | 1.5 | 1.1-2.0 | .012 |
| Female | 1.2 | .642 | 1.3 | .551 | — | — | — |
| WBC, diagnosis | 1.0 | .798 | 1.0 | .329 | — | — | — |
| Cytogenetic Risk* (reference unfavorable) | | | | | | | |
| Intermediate | 0.4 | .057 | 0.6 | .236 | 0.5 | 0.1-1.1 | .087 |
| Favorable | 0.1 | .008 | 0.1 | .030 | 0.1 | 0.0-1.0 | .047 |
| FLT3-ITD+ | 0.9 | .666 | 0.5 | .168 | — | — | — |
| NPM1+/FL3-ITD− | 0.4 | .131 | 0.3 | .081 | — | — | — | divide by 10;
%10-year increase;
*Medical Research Council criteria (2010)
OR, odds ratio;
CI, confidence interval;
WBC, white blood cell;
FLT3-ITD, FMS-like kinase 3-internal tandem duplication;
NPM1, nucleophosmin1

TABLE 7

UPenn Cohort: Clinical Outcome by High versus Low M-score.

|  | Median OS (months) | 2-Year OS (%) | CR Rate (%) |
|---|---|---|---|
| Total Cohort (n = 166) | | | |
| Low M-score | 26.6 | 56% | 84% |
| High M-score | 10.8 | 24% | 61% |
| Age ≤60 years, Intermediate Cytogenetics (n = 82) | | | |
| Low M-score | 36.4 | 62% | 91% |
| High M-score | 14.9 | 30% | 70% |
| Achieved CR (n = 118) | | | |
| Low M-score | 43.9 | 67% | — |
| High M-score | 17.2 | 38% | — |

OS, overall survival;
CR, complete remission

TABLE 8

Mean M-score by Mutant Status of DNA Methylation Regulatory Genes for UPenn Cohort (n = 136).

|  | n | % | M-score (Mean) | 95% CI | P |
|---|---|---|---|---|---|
| DNMT3A | | | | | |
| Mutant | 42 | 30.1 | 101.5 | 91.1-111.9 | .031 |
| Wildtype | 94 | 69.1 | 66.8 | 81.7-94.9 | |
| TET2 | | | | | |
| Mutant | 19 | 14.0 | 105.3 | 89.9-117.0 | .122 |
| Wildtype | 117 | 86.0 | 90.6 | 84.5-96.7 | |
| IDH2 | | | | | |
| Mutant | 15 | 11.0 | 101.2 | 89.0-113.4 | .275 |
| Wildtype | 121 | 89.0 | 91.3 | 85.2-97.4 | |

TABLE 8-continued

Mean M-score by Mutant Status of DNA Methylation Regulatory Genes for UPenn Cohort (n = 136).

|  | n | % | M-score (Mean) | 95% CI | P |
|---|---|---|---|---|---|
| IDH1 | | | | | |
| Mutant | 11 | 8.9 | 118.7 | 85.7-141.6 | .025 |
| Wildtype | 125 | 91.9 | 90.5 | 84.9-96.1 | |
| WT1 | | | | | |
| Mutant | 8 | 5.9 | 87.2 | 66.1-108.3 | .649 |
| Wildtype | 28 | 94.1 | 92.7 | 88.9-98.6 | |

CI, confidence interval;
DNMT3A, DNA methyltransferase 3A;
TET2, tet methylcytosine dioxygenase 2;
IDH2, isocitrate dehydrogenase 2;
IDH1, isocitrate dehydrogenase 2;
WT1, wilms tumor1.

Validation of the M-Score Classifier in the E1900 Cohort

Validation of the M-score prognostic classifier for OS in the independent E1900 cohort (also referred to herein as ECOG), described in Table 12, was sought. The association of M-score with characteristics of this cohort is described in Tables 12-14. For these patients, the mean and median M-score were similar to the UPenn cohort (98.2 (95% CI, 94.1 to 102.3) and 91.8 (range, 20.0 to 204.6), respectively) (FIG. 12). Also similar to the UPenn cohort, the M-score was associated with survival on multivariable analysis (P<0.0001), while the association with achievement of CR was marginally significant (P=0.076).

Figure 11:
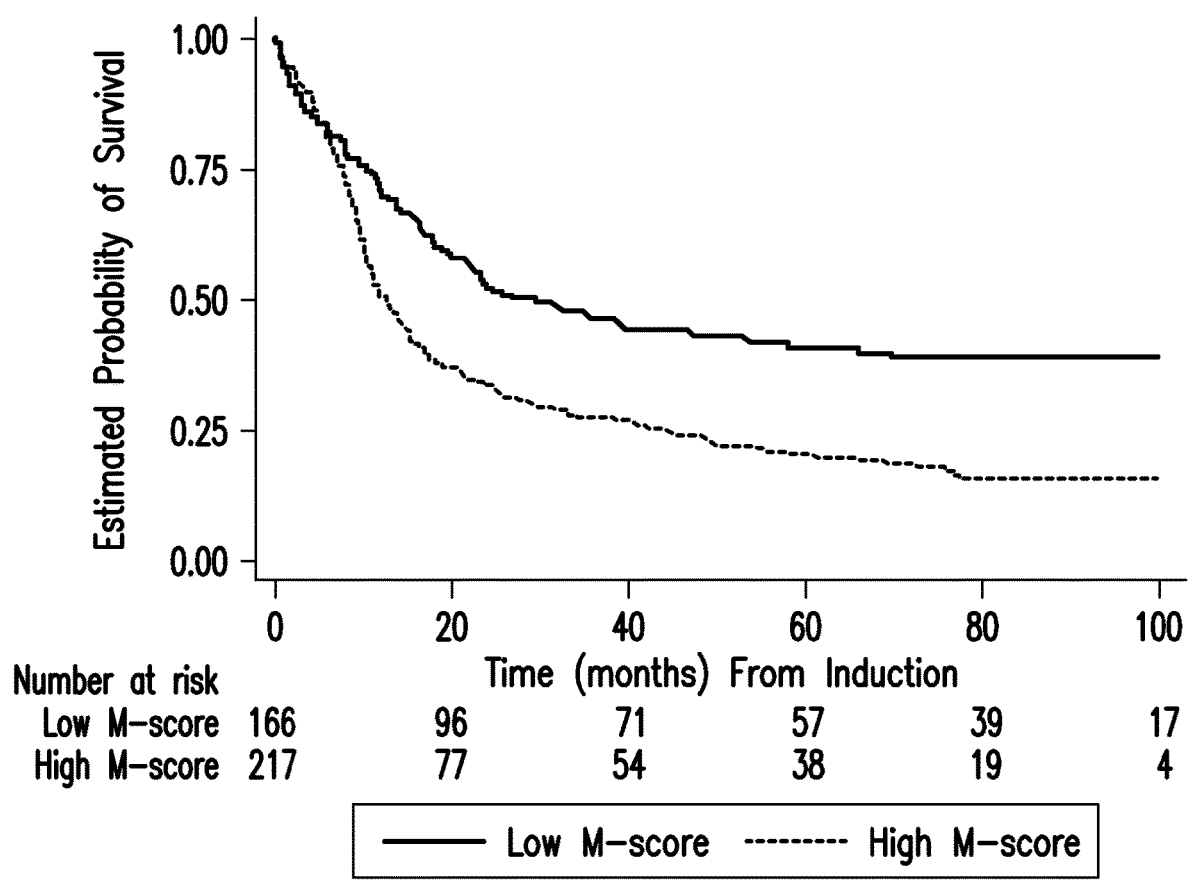
FIG. 11. Kaplan-Meier curves of overall survival in the E1900 cohort. Subgroups are determined by the optimal M-score (n=383; log-rank P<0.00001).

The binary prognostic classifier derived in the UPenn cohort successfully identified E1900 subgroups with different OS (log-rank P<0.00001, FIG. 11). The median OS in patients in the low M-score group was 29.5 months versus 12.6 months for those in the high M-score (FIG. 11). Among patients with intermediate cytogenetics (n=249), OS was also significantly different (log-rank P=0.0003) with median OS of 32.3 months versus 14.1 months in the low and high M-score groups, respectively.

Figure 15:
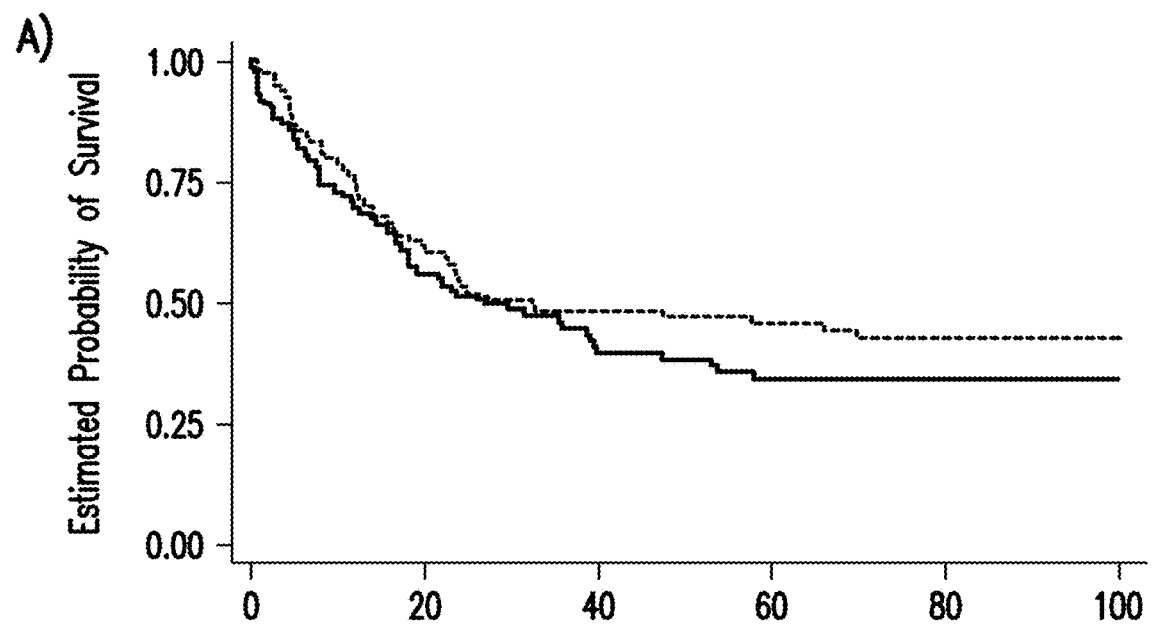
FIG. 15A-B. E1900 Cohort: Kaplan Meier curves of overall survival by daunorubicin dose stratified by low and high M-score. A) Low M-score; n=166, log-rank P=0.328. B) High M-score; n=217, log-rank P=0.001.
Figure 15:
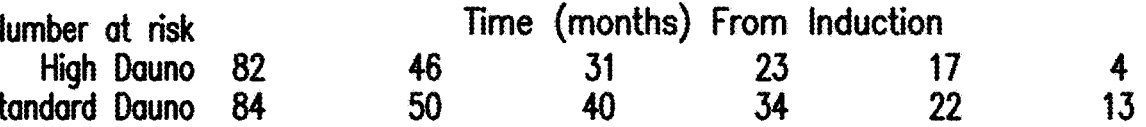
Figure 15:
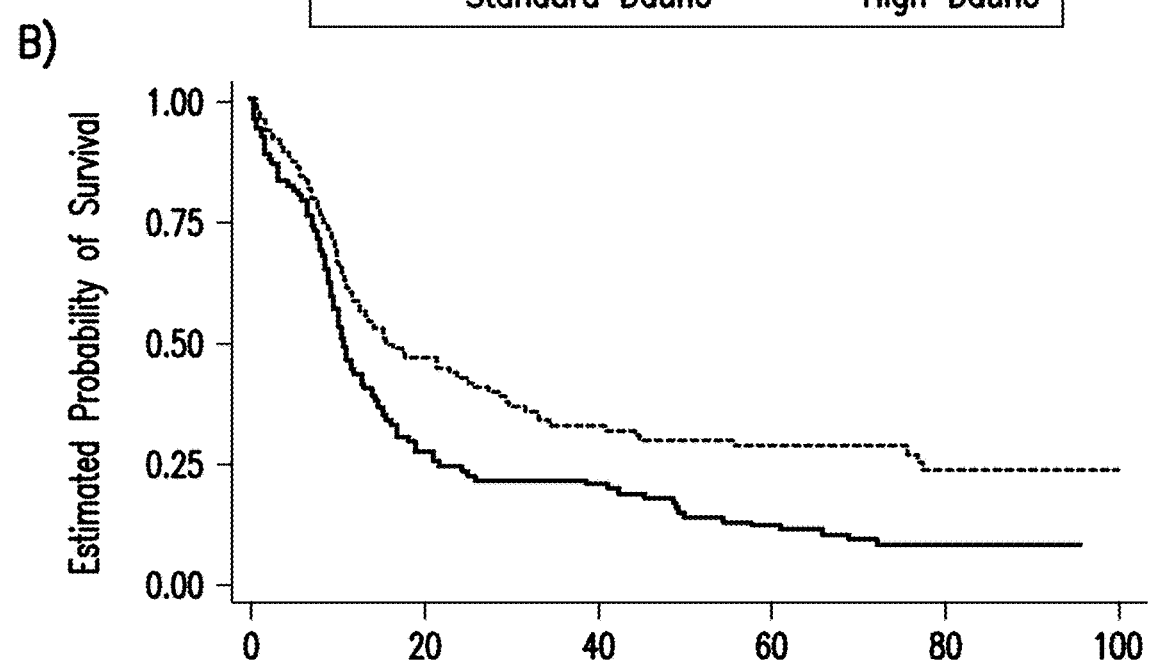
Figure 15:
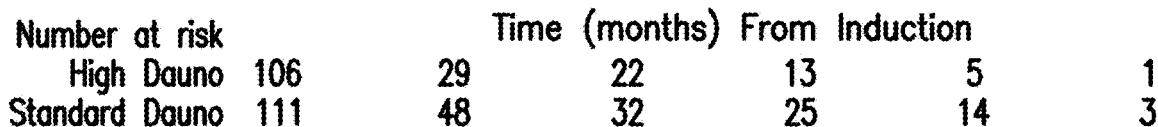

Since a primary objective of E1900 was to assess the impact of daunorubicin dose on AML outcome, the impact of treatment on patients with low and high M-scores was assessed. High-dose daunorubicin was found to be beneficial for patients with high M-scores (log-rank P=0.001) but not for those with low M-scores (P=0.328; FIG. 15).

TABLE 9

UPenn Cohort: Expanded Cox Model for Overall Survival (n = 136, events = 108).

| | Univariate | | Multi-variable | | Reduced | | |
|---|---|---|---|---|---|---|---|
| | | | Adj | | Adj | 95% | |
| Parameter | HR | P | HR | P | HR | CI | P |
| M-score$^\#$ | 1.1 | <.0001 | 1.1 | .002 | 1.1 | 1.1-1.2 | <.0001 |
| Age$^\%$ | 1.3 | <.0001 | 1.3 | .002 | 1.3 | 1.1-1.5 | .004 |
| Female | 1.1 | .503 | 1.0 | .868 | — | — | — |
| WBC, diagnosis$^\#$ | 1.0 | .289 | 1.0 | .150 | 1.03 | 1.00-1.06 | .035 |

TABLE 9-continued

UPenn Cohort: Expanded Cox Model for Overall Survival (n = 136, events = 108).

| | Univariate | | Multi-variable | | Reduced | | |
|---|---|---|---|---|---|---|---|
| | | | Adj | | Adj | 95% | |
| Parameter | HR | P | HR | P | HR | CI | P |
| Cytogenetic Risk (ref unfavorable) | | | | | | | |
| Intermediate | 0.8 | .400 | 9.8 | .414 | — | — | — |
| Favorable | 0.4 | .014 | 0.6 | .256 | — | — | — |
| FLT3-ITD+ | 1.8 | .026 | 1.3 | .351 | — | — | — |
| NPM1+/FLT3-ITD− | 0.5 | .033 | 1.3 | .107 | 0.6 | 0 | .048 |
| DNMT3A | 1.3 | .192 | 1.0 | .897 | — | — | — |
| IDH1 | 1.2 | .536 | 1.3 | .464 | — | — | — |

$^\#$divided by 10;
$^\%$10-year increase;
*Medical Research Council criteria (2010)
HR, hazard ratio;
CI, confidence interval;
WBC, white blood cell;
FLT3-ITD, FMS-like kinase 3-internal tandem duplication;
NPM1, nucleophosmin1;
DNMT3A, DNA methyltransferase 3A;
IDH1, isocitrate dehydrogenase 1

TABLE 10

UPenn Cohort: Expanded Logistic Model for Failure to Achieve Complete Remission (n = 136, events = 38).

| | Univariate | | Multivariable | | Reduced | | |
|---|---|---|---|---|---|---|---|
| Parameter | OR | P | Adj OR | P | Adj OR | 95% OR | P |
| M-score$^\#$ | 1.2 | .001 | 1.2 | .036 | 1.2 | 1.1-1.4 | .002 |
| Age$^\%$ | 1.7 | .002 | 1.8 | .002 | 1.7 | 1.2-2.5 | .003 |
| Female | 0.9 | .886 | 0.7 | .559 | — | — | — |
| WBC, diagnosis$^\#$ | 1.0 | .620 | 1.0 | .412 | — | — | — |
| Cytogenetics | | | | | | | |
| Intermediate | 0.4 | .087 | 0.5 | .180 | — | — | — |
| Favorable | 0.1 | .012 | 0.1 | .030 | — | — | — |
| FLT3-ITD+ | 0.9 | .761 | 0.8 | .663 | — | — | — |
| NPM1+/FLT3-ITD− | 0.4 | .141 | 0.3 | .123 | — | — | — |
| DNMT3A | 0.6 | .260 | 0.4 | .088 | — | — | — |
| IDH1 | 3.5 | .051 | 6,4 | .028 | — | — | — |

$^\#$divided by 10;
$^\%$10-year increase;
*Medical Research Council criteria (2010)
OR, odds ratio;
CI, confidence interval;
WBC, white blood cell;
FLT3-ITD, FMS-like kinase 3-internal tandem duplication;
NPM1, nucleophosmin1;
DNMT3A, DNA methyltransferase 3A;
IDH1, isocitrate dehydrogenase 1

TABLE 11

Patient and Disease Characteristics by Optimal M-score for the UPenn Cohort.

| | Total Cohort | | | Age ≤60 years Intermediate Cytogenetic Risk | | | Achieved CR | | |
|---|---|---|---|---|---|---|---|---|---|
| | Low M-score (n =74) % | High M-score (n = 92) % | P | Low M-score (n = 35) % | High M-score (n = 47) % | P | Low M-score (n = 62) % | High M-score (n = 56) % | P |
| Age | | | | | | | | | |
| ≤60 years | 77.0 | 62.0 | .037 | — | — | — | 82.3 | 66.1 | .044 |
| >60 years | 23.0 | 38.0 | | — | — | — | 17.7 | 33.9 | |
| Sex | | | | | | | | | |
| Male | 62.2 | 56.5 | .463 | 60.0 | 53.2 | .539 | 62.9 | 57.1 | .523 |
| Female | 37.8 | 43.5 | | 40.0 | 46.8 | | 37.1 | 42.9 | |
| WBC (×10⁹/L), diagnosis | | | | | | | | | |
| <100 | 79.7 | 78.3 | .818 | 74.3 | 70.2 | .685 | 82.3 | 75.0 | .335 |
| ≥100 | 20.3 | 21.7 | | 25.7 | 29.8 | | 17.7 | 25.0 | |
| Cytogenetic risk group* | | | | | | | | | |
| Favorable | 25.7 | 2.2 | <.0001 | — | — | — | 29.0 | 3.6 | .001 |
| Intermediate | 60.8 | 79.3 | | — | — | — | 59.7 | 83.9 | |
| Unfavorable | 13.5 | 18.5 | | — | — | — | 11.3 | 12.5 | |
| FLT3-ITD | | | | | | | | | |
| Mutant | 25.7 | 40.2 | .049 | 40.0 | 48.9 | .421 | 72.6 | 57.1 | .079 |
| Wildtype | 74.3 | 59.8 | | 60.0 | 51.1 | | 27.4 | 42.9 | |
| NPM1 | | | | | | | | | |
| Mutant | 32.4 | 37.0 | .543 | 54.3 | 40.4 | .213 | 61.3 | 55.4 | .514 |
| Wildtype | 67.7 | 63.0 | | 45.7 | 59.6 | | 38.7 | 44.6 | |
| NPM1+, FLT3-ITD– | | | | | | | | | |
| Yes | 17.6 | 13.0 | .418 | 28.6 | 14.9 | .131 | 79.0 | 85.7 | .353 |
| No | 82.4 | 87.0 | | 71.4 | 85.1 | | 21.0 | 14.3 | |

*Medical Research Council criteria (2010)
AML, acute myeloid leukemia;
WBC, white blood cell;
FLT3-ITD, FMS-like kinase 3-internal tandem duplication;
NPM1, nucleophosmin1

TABLE 12

E1900 Cohort: M-score by Patient, Disease, and Sample Characteristics (n = 383).

| | n | % | M-score (Mean) | 95% CI | P |
|---|---|---|---|---|---|
| All Subjects | 383 | — | 98.2 | 94.1-102.3 | — |
| Sex | | | | | |
| Male | 201 | 52.5 | 96.3 | 90.8-101.8 | .347 |
| Female | 182 | 47.5 | 100.2 | 94.0-106.5 | |
| WBC (× 10⁹/L), diagnosis | | | | | |
| <100 | 360 | 94.0 | 97.2 | 93.0-101.5 | .06 |
| ≥100 | 23 | 6.0 | 113.6 | 95.9-131.4 | |
| Cytogenetic risk group* | | | | | |
| Favorable | 66 | 17.2 | 65.1 | 59.3-70.9 | <.0001 |
| Intermediate | 254 | 66.3 | 103.4 | 98.3-108.4 | |
| Unfavorable | 63 | 16.5 | 112.0 | 102.1-122.0 | |
| FLT3-ITD | | | | | |
| Mutant | 113 | 29.5 | 111.9 | 87.8-97.2 | <.0001 |
| Wildtype | 270 | 70.5 | 92.5 | 103.9-119.8 | |
| NPM1 | | | | | |
| Mutant | 115 | 30.0 | 107.2 | 99.7-114.8 | .005 |
| Wildtype | 268 | 70.0 | 94.3 | 89.4-99.2 | |
| NPM1+/FLT3-ITD- | | | | | |
| Yes | 66 | 17.2 | 98.0 | 88.8-107.2 | .964 |
| No | 317 | 82.8 | 98.2 | 93.6-102.9 | |
| Induction Treatment | | | | | |
| Standard Dose | 188 | 49.1 | 98.0 | 92.5-104.2 | .946 |
| High Dose | 195 | 50.9 | 98.4 | 92.2-103.9 | |

*Slovak et al. (2000)
CI, confidence interval;
AML, acute myeloid leukemia;
WBC, white blood cell;
FLT3-ITD, FMS-like kinase 3-internal tandem duplication;
NPM1, nucleophosmin1

Discussion

Multivariable models incorporating standard AML prognostic characteristics have only a modest ability to predict clinical outcome, and the addition of molecular markers adds little to these models (40-42). To improve AML prognostication, a clinically applicable assay for multi-locus methylation assessment (xMELP) along with a corresponding statistic (M-score) was developed (15, 33). As shown in this Example, the M-score was associated with CR and OS in both univariate and multivariable models in the UPenn cohort. Without being limited to a particular theory, in this cohort, a reduced model for OS is based solely on the M-score, patient age, and NPM1+/FLT3-ITD-status; other information, including cytogenetics and presence of a FLT3-ITD mutation, provided little additional prognostic value. The association between M-score and recurrent intragenic mutations were also explored in the subgroup of UPenn patients with available extended mutation profiles obtained by next-generation sequencing. Mean M-score was higher in DNMT3A mutant patients and in the small group of IDH1 mutant patients, but multivariable analyses including DNMT3A and IDH1 confirmed the independent association of M-score and clinical outcomes.

Determining the mutational profile in AML will remain important to clinical care, particularly in settings where mutations are able to predict response to targeted agents; however, clinical use of the xMELP assay and associated M-score may decrease the need for comprehensive genetic testing for risk stratification at diagnosis (36-39). The disclosed reduced multivariable models indicate that the M-score has a stronger association with clinical outcome than many established prognostic factors, including cytogenetics and FLT3-ITD status, as well as other genetic lesions now commonly assessed by next-generation sequencing analysis.

Cox regression analyses showed strong association between the M-score and clinical outcomes; however, it is difficult to apply continuous measures of association in clinical practice. The binary M-score classifier, which was validated in multiple clinically important subgroups and an independent cohort, clearly enhances the usefulness of the M-score for practicing clinicians. Additionally, the different responses to daunorubicin seen in M-score defined groups suggests that M-score may correlate with chemoresistance and identify patients that could benefit from high-dose chemotherapy.

It is important to recognize that the loci contributing to the M-score do not account for all sites subject to aberrant methylation in AML. These specific loci in combination represent a marker of prognosis rather than a description of abnormal methylation or an explanatory model of AML biology. The prognostic value of the M-score for patients with AML arising in the setting of prior chemotherapy or myelodysplasia, or those treated with non-intensive regimens including hypomethylating agents, are areas of further research. Additionally, no information regarding the association between M-score and other prognostic markers, including minimal residual disease status was obtained (39).

In summary, the M-score provides valuable information in the clinical setting regarding the likelihood of long-term survival after AML induction. Those patients predicted to have poor outcomes based on M-score may be better served with more intensive post-remission treatment or enrollment on a clinical trial.

TABLE 13

E1900 Cohort: Cox Model for Overall Survival (n = 383, events = 275)

| Parameter | Univariate | | Multivariable | | Reduced | | |
|---|---|---|---|---|---|---|---|
| | HR | P | Adj HR | P | Adj HR | 95% CI | P |
| M-score[#] | 1.1 | <.0001 | 1.1 | <.0001 | 1.1 | 1.05-1.1 | <.0001 |
| Age[%*] | 1.2 | .004 | 1.1 | .015 | 1.1 | 1.03-1.3 | .010 |
| Female | 0.9 | .443 | 0.9 | .287 | — | — | — |
| WBC, diagnosis[#] | 1.1 | <.0001 | 1.05 | .003 | 1.05 | 1.02-1.03 | .001 |
| Cytogenetic Risk (reference unfavorable) | | | | | | | |
| Intermediate | 0.4 | <.0001 | 0.5 | <.0001 | 0.5 | 0.4-0.7 | <.0001 |
| Favorable | 0.3 | <.0001 | 0.4 | <.0001 | 0.4 | 0.2-0.6 | <.0001 |
| FLT3-ITD+ | 1.6 | <.0001 | 1.1 | .383 | — | — | — |
| NPM1+/FLT3-ITD− | 0.5 | <.0001 | 0.5 | <.0001 | 0.4 | 0.3-0.6 | <.0001 |

[#]divided by 10;
[%]10-year increase;
*Slovak et al. (2000)
HR, hazard ratio;
CI, confidence interval;
WBC, white blood cell;
FLT3-ITD, FMS-like kinase 3-internal tandem duplication;
NPM1, nucleophosmin1

TABLE 14

E1900 Cohort: Logistic Model for Failure to Achieve Complete Remission (n = 383, events = 140)

| Parameter | Univariate OR | Univariate P | Multivariable Adj OR | Multivariable Adj P | Reduced Adj OR | Reduced 95% CI | Reduced P |
|---|---|---|---|---|---|---|---|
| M-score[#] | 1.1 | .001 | 1.05 | .076 | — | — | — |
| Age[%] | 1.1 | .127 | 1.1 | .369 | — | — | — |
| Female | 0.8 | .241 | 0.8 | .251 | — | — | — |
| WBC, Diagnosis* | 1.1 | .045 | 1.1 | .066 | — | — | — |
| Cytogenetic Risk (ref unfavorable) | | | | | | | |
| Intermediate | 0.6 | .054 | 0.8 | .508 | 0.7 | 0.4-1.3 | .32 |
| Favorable | 0.2 | <.0001 | 0.3 | .006 | 0.2 | 0.1-0.5 | <.0001 |
| FLT3-ITD+ | 1.6 | .044 | 0.9 | .674 | — | — | — |
| NPM1+/FLT3-ITD− | 0.3 | .001 | 0.3 | .001 | 0.3 | 0.1-0.6 | <.0001 |

[#]divided by 10,
[%]10-year increase,
*Slovak et al. (200)
OR, odds ratio;
CI, confidence interval;
WBC, white blood cell;
FLT3-ITD, FMS-like kinase 3-internal tandem duplication;
NPM1, nucleophosmin1;
WT, wildtype;
ref, reference

REFERENCES

1. Hanahan D, Weinberg R A. Hallmarks of cancer: the next generation. Cell. 2011; 144:646-74.
2. Vogelstein B, Kinzler K W. The multistep nature of cancer. Trends Genet. 1993; 9:138-41.
3. Watson I R, Takahashi K, Futreal P A, Chin L. Emerging patterns of somatic mutations in cancer. Nat Rev Genet 2013; 14 703-18.
4. Baylin S B, Jones P A. A decade of exploring the cancer epigenome-biological and translational implications. Nat Rev Cancer. 2011; 11:726-34.
5. Noushmehr H, Weisenberger O J, Diefes K, Phillips H S, Pujara K, Berman B P, et al. Identification of a CpG island methylator phenotype that defines a distinct subgroup of glioma. Cancer Cell. 2010; 17:510-22.
6. Figueroa M E, Lugthart S, Li Y, Erpelinck-Verschueren C, Deng X, Christos P J, et al. DNA methylation signatures identify biologically distinct subtypes in acute myeloid leukemia. Cancer Cell. 2010; 17:13-27.
7. Bullinger L, Ehrich M, Dohner K, Schlenk R F, Dohner H, Nelson M R, et al. Quantitative DNA methylation predicts survival in adult acute myeloid leukemia. Blood. 2010; 115:636-42.
8. Alvarez S, Suela J, Valencia A, Fernandez A, Wunderlich M, Agirre X, et al. DNA methylation profiles and their relationship with cytogenetic status in adult acute myeloid leukemia. PLoS ONE. 2010; 5:e12197.
9. Borssen M, Palmqvist L, Karrman K, Abrahamsson J, Behrendtz M, Heldrup J, et al. Promoter DNA methylation pattern identifies prognostic subgroups in childhood T-cell acute lymphoblastic leukemia. PLoS ONE. 2013; 8:e65373.
10. Nordlund J, Backlin C L, Wahlberg P, Busche S, Berglund E C, Eloranta M-L, et al. Genome-wide signatures of differential DNA methylation in pediatric acute lymphoblastic leukemia. Genome Bioi. 2013; 14:r105.
11. Sandoval J, Mendez-Gonzalez J, Nadal E, Chen G, Carmona F J, Sayols S, et al. A prognostic DNA methylation signature for stage I non-small-cell lung cancer. J Clin Oncol 2013; 31:4140-7.
12. Wei S H, Balch C, Paik H H, Kim Y-S, Baldwin R L, Liyanarachchi S, et al. Prognostic DNA methylation biomarkers in ovarian cancer. Clin Cancer Res. 2006; 12:2788-94.
13. Sigalotti L, Covre A, Fratta E, Parisi G, Sonego P, Colizzi F, et al. Whole genome methylation profiles as independent markers of survival in stage IIIC melanoma patients. J Trans' Med. 2012; 10:185.
14. Pedersen I S, Krarup H B, Thorlacius-Ussing O, Madsen P H. High recovery of cell free methylated DNA based on a rapid bisulfite-treatment protocol. BMC Mol Bioi. 2012; 13:12.
15. Wertheim G B W, Smith C, Figueroa M E, Kalos M, Bagg A, Carroll M, et al. Microsphere-based multiplex analysis of DNA methylation in acute myeloid Leukemia. J Mol Diagn. 2014; 16:207-15.
16. Figueroa M E, Melnick A, Greally J M. Genome-wide determination of DNA methylation by Hpa II tiny fragment enrichment by ligation-mediated PCR (HELP) for the study of acute leukemias. Methods Mol Bioi. 2009; 538:395-407.
17. King R L, Naghashpour M, Watt C D, Morrissette J J D, Bagg A. A comparative analysis of molecular genetic and conventional cytogenetic detection of diagnostically important translocations in more than 400 cases of acute leukemia, highlighting the frequency of false-negative conventional cytogenetics. Am J Clin Pathol. 2011; 135: 921-8.
18. Bertoli S, Berard E, Huguet F, Huynh A, Tavitian S, Vergez F, et al. Time from diagnosis to intensive chemotherapy initiation does not adversely impact the outcome of patients with acute myeloid leukemia. Blood. 2013; 121:2618-26.
19. R Core Team. R: A Language and Environment for Statistical Computing. R Foundation for Statistical Computing, Vienna, Austria. 2013. <URL: http://www.R-project org/>
20. Therneau T. A Package for Survival Analysis. R package version 2.37-7.2014. <URL: http://CRAN.R-projectorg/package=survival>
21. Carstensen R, Gurrin L, Ekstrom C, Figurski M. MethComp: Functions for analysis of agreement in method comparison studies. R package version 1.22. 2013. <URL: http://CRAN.R-project org/package=MethComp>
22. Ligges U, Machler M. Scatterplot3d—an R Package for Visualizing Multivariate Data. Journal of Statistical Software. 2003; 8(11):1-20.
23. Ishwaran H, Kolalur U B. Random Forests for Survival, Regression and Classification (RF=SRC). R package version 1 A. 2013. <URL: http://CRAN.Rproject org/package=random ForestS RC>
24. Hastie T, Tibshirani R, Friedman J. The Elements of Statistical Learning. Springer; 2009.
25. Raess P W, van de Geijn G-J M, Njo T L, Klop B, Sukhachev D, Wertheim G, et al. Automated screening for myelodysplastic syndromes through analysis of complete blood count and cell population data parameters. Am J Hematol. 2014; 89:369-74.

26. Hapfelmeier A, Ulm K. A new variable selection approach using Random Forests. Computational Statistics & Data Analysis. 2013; 60:50-69.
27. Ishwaran H, Kogalur U B, Blackstone E H. Random survival forests. The Annals of Applied Statistics. 2008; 2(3):841-60.
28. Bair E, Hastie T, Paul D, Tibshirani R. Prediction by Supervised Principal Components. Journal of the American Statistical Association. 2006; 101 (473):119-37.
29. Grimwade D. et al. Refinement of cytogenetic classification in acute myeloid leukemia: determination of prognostic significance of rare recurring chromosomal abnormalities among 5876 younger adult patients treated in the United Kingdom Medical Research Council trials. Blood. 2010; 116(3):354-365.
30. Jiang D, Hong Q, Shen Y, et al. The diagnostic value of DNA methylation in leukemia: a systematic review and meta-analysis. PloS One 2014; 9:e96822.
31. Marcucci G, Yan P, Maharry K, et al. Epigenetics meets genetics in acute myeloid leukemia: clinical impact of a novel seven-gene score. J Clin Oncol 2014; 32:548-56.
32. Deneberg S, Grovdal M, Karimi M, et al. Gene-specific and global methylation patterns predict outcome in patients with acute myeloid leukemia. Leukemia 2010; 24:932-41.
33. Wertheim G B, Smith C, Luskin M, et al. Validation of DNA methylation to predict outcome in acute myeloid leukemia by use of xMELP. Clin Chem 2015; 61:249-58.
34. Cheson B D, Bennett J M, Kopecky K J, et al. Revised recommendations of the International Working Group for Diagnosis, Standardization of Response Criteria, Treatment Outcomes, and Reporting Standards for Therapeutic Trials in Acute Myeloid Leukemia. J Clin Oncol 2003; 21:4642-9.
35. Fernandez H F, Sun Z, Yao X, et al. Anthracycline dose intensification in acute myeloid leukemia. N Engl J Med 2009; 361:1249-59.
36. Man C H, Fung T K, Ho C, et al. Sorafenib treatment of FLT3-ITD(+) acute myeloid leukemia: favorable initial outcome and mechanisms of subsequent nonresponsiveness associated with the emergence of a D835 mutation. Blood 2012; 119:5133-43.
37. Pemmaraju N, Kantarjian H, Andreeff M, Cortes J, Ravandi F. Investigational FMS-like tyrosine kinase 3 inhibitors in treatment of acute myeloid leukemia. Expert Opin Investig Drugs 2014; 23:943-54.
38. Stein E M, Altman J K, Collins R, et al. AG-221, an oral, selective, first-in-class, potent inhibitor of the IDH2 mutant metabolic enzyme, induces durable remissions in a phase 1 study in patients with IDH2 mutation positive advanced hematologic malignancies [abstract]. Blood 2014; 124:abstract 115.
39. Chen X, Xie H, Wood B L, et al. Relation of clinical response and minimal residual disease and their prognostic impact on outcome in acute myeloid leukemia. J Clin Oncol 2015; 33:1258-64.
40. Walter R B, Othus M, Burnett A K, et al. Resistance prediction in AML: analysis of 4601 patients from MRC/NCRI, HOVON/SAKK, SWOG and M D Anderson Cancer Center. Leukemia 2015; 29:312-20.
41. Krug U, Rollig C, Koschmieder A, et al. Complete remission and early death after intensive chemotherapy in patients aged 60 years or older with acute myeloid leukaemia: a web-based application for prediction of outcomes. Lancet 2010; 376:2000-8.
42. Walter R B, Othus M, Paietta E M, et al. Effect of genetic profiling on prediction of therapeutic resistance and survival in adult acute myeloid leukemia [abstract]. Blood 2014; 124:abstract 941.
43. Akalin A, Garrett-Bakelman F E, Kormaksson M, et al. Base-pair resolution DNA methylation sequencing reveals profoundly divergent epigenetic landscapes in acute myeloid leukemia. PLoS Genet 2012; 8:e1002781.
44. Schoofs T, Berdel W E, Muller-Tidow C. Origins of aberrant DNA methylation in acute myeloid leukemia. Leukemia 2014; 28:1-14.

Various publications, patents and patent applications are cited herein, the contents of which are hereby incorporated by reference in their entireties.

What is claimed is:

1. A method for determining the methylation status of one or more genomic DNA loci, wherein the method comprises:
   (a) isolating genomic DNA from one or more cells of a biological sample of a subject;
   (b) digesting a first sample of the genomic DNA with a methylation-insensitive restriction enzyme to form a first sample of genomic DNA fragments, and digesting a second sample of the genomic DNA with a methylation-sensitive restriction enzyme to form a second sample of genomic DNA fragments;
   (c) ligating a nucleic acid linker to the genomic DNA fragments of the first sample and the second sample;
   (d) amplifying the first sample and the second sample of genomic DNA fragments to generate a first sample and a second sample of amplified DNA fragments respectively;
   (e) contacting the amplified DNA fragments of the first sample and the second sample with microspheres, each microsphere having a unique fluorescent label and a genomic DNA locus-specific probe, wherein the amplified DNA fragments hybridize to the probe;
   (f) quantifying the amplified DNA fragments of the first sample and the second samples bound to microspheres by flow cytometry; and
   (g) comparing the amount of hybridized DNA fragments in the second sample to the amount of hybridized DNA fragments in the first sample to determine the methylation status of the genomic DNA locus that corresponds to the locus-specific probe;
   wherein the digesting and ligating are performed in a single reaction, and
   wherein, upon ligation with the nucleic acid linker, the genomic DNA fragments do not have a restriction site for the methylation-sensitive enzyme and the methylation-insensitive enzyme.

2. The method of claim 1, wherein the methylation-insensitive restriction enzyme is MspI.

3. The method of claim 1, wherein the methylation-sensitive restriction enzyme is HpaII.

4. The method of claim 1, wherein the one or more genomic loci are selected from the group consisting of Chr 17: 2208021 to 2208391 (MSPI0406S00783415); Chr 20: 32274469 to 32275009 (MSPI0406S00920592); Chr 6: 3024925 to 3025589 (MSPI0406S00304798); Chr 3: 129274773 to 129275235 (MSPI0406S00196536); Chr 14: 105860849 to 105861218 (MSPI0406S00697563); Chr 1: 11723172 to 11723834 (MSPI0406S00011246); Chr 19: 1924052 to 1924259 (MSPI0406S00861109); Chr 6: 108615428 to 108615973 (MSPI0406S00333894); Chr 16: 30538940 to 30539797 (MSPI0406S00754805); Chr 12: 53661106 to 53661621 (MSPI0406S00613804); Chr 3: 48601900 to 48602237 (MSPI0406S00176846); Chr 15: 65810129 to 65810776 (MSPI0406S00715593); Chr 14: 106354882 to 106355276 (MSPI0406S00698115); Chr 12: 6233715 to 6234255 (MSPI0406S00600078); Chr 20: 11899205 to 11899843 (MSPI0406S00914183); Chr 15: 50838542 to 50839225 (MSPI0406S00710190); Chr 3: 8542436 to 8543339 (MSPI0406S00163833); Chr 16: 68345197 to 68345691 (MSPI0406S00765490); Chr 20: 11898849 to 11899205 (MSPI0406S00914182); Chr 20: 11898555 to 11898849 (MSPI0406S00914181); Chr X: 48795887 to 48797005 (MSPI0406S00997890); Chr 18: 5293969 to 5294770 (MSPI0406S00838340); Chr 2: 158114266 to 158115184 (MSPI0406S00136939); Chr 14: 24867489 to 24867729 (MSPI0406S00669709); Chr 1: 32739167 to 32739750 (MSPI0406S00027418); Chr 11: 118763110 to 118763426 (MSPI0406S00589152); Chr 20: 814970 to 815202 (MSPI0406S00910305); Chr 15: 45003463 to 45004002 (MSPI0406S00708912); Chr 6: 34856156 to 34857019 (MSPI0406S00318682); Chr 13: 53028642 to 53029495 (MSPI0406S00653944); Chr 19: 37958559 to 37958860 (MSPI0406S00890278); and combinations thereof.

5. The method of claim 1, wherein the one or more genomic loci are selected from the group consisting of Chr 17: 2208021 to 2208391 (MSPI0406S00783415), Chr 3: 129274773 to 129275235 (MSPI0406S00196536), Chr 1: 11723172 to 11723834 (MSPI0406S00011246), Chr 19: 1924052 to 1924259 (MSPI0406S00861109), Chr 6: 108615428 to 108615973 (MSPI0406S00333894); Chr 16: 30538940 to 30539797 (MSPI0406S00754805), Chr 12: 53661106 to 53661621 (MSPI0406S00613804), Chr 15: 65810129 to 65810776 (MSPI0406S00715593), Chr 14: 106354882 to 106355276 (MSPI0406S00698115), Chr 12: 6233715 to 6234255 (MSPI0406S00600078), Chr 20:

11899205 to 11899843 (MSPI0406S00914183), Chr 15: 50838542 to 50839225 (MSPI0406S00710190), Chr 3: 8542436 to 8543339 (MSPI0406S00163833), Chr 16: 68345197 to 68345691 (MSPI0406S00765490), Chr 20: 11898849 to 11899205 (MSPI0406S00914182), Chr 20: 11898555 to 11898849 (MSPI0406S00914181), Chr 2: 158114266 to 158115184 (MSPI0406S00136939), and combinations thereof.

* * * * *